US008668910B2

(12) United States Patent
Bouchard et al.

(10) Patent No.: US 8,668,910 B2
(45) Date of Patent: Mar. 11, 2014

(54) ANTIBODIES THAT SPECIFICALLY BIND TO THE EPHA2 RECEPTOR

(75) Inventors: Herve Bouchard, Thiais (FR); Alain Commercon, Vitry-sur-Seine (FR); Claudia Fromond, Fleury en Biere (FR); Vincent Mikol, Charenton-le-Pont (FR); Fabienne Parker, Antony (FR); Ingrid Sassoon, Villejuif (FR); Daniel Tavares, Natick, MA (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/499,459

(22) PCT Filed: Sep. 30, 2010

(86) PCT No.: PCT/IB2010/054422
§ 371 (c)(1), (2), (4) Date: Mar. 30, 2012

(87) PCT Pub. No.: WO2011/039724
PCT Pub. Date: Apr. 7, 2011

(65) Prior Publication Data
US 2012/0201828 A1 Aug. 9, 2012

(30) Foreign Application Priority Data
Oct. 2, 2009 (EP) .................................... 09305938

(51) Int. Cl.
*A61K 39/395* (2006.01)
*C07K 16/18* (2006.01)
*C07K 16/28* (2006.01)

(52) U.S. Cl.
USPC .................. 424/143.1; 424/130.1; 424/133.1; 424/141.1; 424/178.1; 530/387.1; 530/388.1; 530/388.22

(58) Field of Classification Search
None
See application file for complete search history.

(56) References Cited

U.S. PATENT DOCUMENTS

| | | | |
|---|---|---|---|
| 4,256,746 | A | 3/1981 | Miyashita et al. |
| 4,294,757 | A | 10/1981 | Asai |
| 4,307,016 | A | 12/1981 | Asai et al. |
| 4,313,946 | A | 2/1982 | Powell et al. |
| 4,315,929 | A | 2/1982 | Freedman et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,444,887 | A | 4/1984 | Hoffmann et al. |
| 4,450,254 | A | 5/1984 | Isley et al. |
| 4,716,111 | A | 12/1987 | Osband et al. |
| 4,816,397 | A | 3/1989 | Boss et al. |
| 4,816,567 | A | 3/1989 | Cabilly et al. |
| 4,946,778 | A | 8/1990 | Ladner et al. |
| 5,208,020 | A | 5/1993 | Chari et al. |
| 5,223,409 | A | 6/1993 | Ladner et al. |
| 5,258,498 | A | 11/1993 | Huston et al. |
| 5,403,484 | A | 4/1995 | Ladner et al. |
| 5,416,064 | A | 5/1995 | Chari et al. |
| 5,427,908 | A | 6/1995 | Dower et al. |
| 5,475,092 | A | 12/1995 | Chari et al. |
| 5,516,637 | A | 5/1996 | Huang et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,571,698 | A | 11/1996 | Ladner et al. |
| 5,580,717 | A | 12/1996 | Dower et al. |
| 5,585,089 | A | 12/1996 | Queen et al. |
| 5,585,499 | A | 12/1996 | Chari et al. |
| 5,639,641 | A | 6/1997 | Pedersen et al. |
| 5,658,727 | A | 8/1997 | Barbas et al. |
| 5,698,426 | A | 12/1997 | Duse |
| 5,733,743 | A | 3/1998 | Johnson et al. |
| 5,739,277 | A | 4/1998 | Presta et al. |
| 5,750,753 | A | 5/1998 | Kimae et al. |
| 5,780,225 | A | 7/1998 | Wigler et al. |
| 5,807,715 | A | 9/1998 | Morrison et al. |
| 5,814,318 | A | 9/1998 | Lonberg et al. |
| 5,821,047 | A | 10/1998 | Garrard et al. |
| 5,846,545 | A | 12/1998 | Chari et al. |
| 5,969,108 | A | 10/1999 | McCafferty et al. |
| 6,150,584 | A | 11/2000 | Kucherlapati et al. |

(Continued)

FOREIGN PATENT DOCUMENTS

| | | | |
|---|---|---|---|
| EP | 0239400 | A2 | 9/1987 |
| EP | 0307 434 | B2 | 3/1989 |

(Continued)

OTHER PUBLICATIONS

Lee Jeong-Won, et al.: EphA2 Immunoconjugate as Molecularly Targeted Chemotherapy for Ovarian Carcinoma, Journal of the National Cancer Institute, 2009, vol. 101, No. 17, pp. 1193-1205.
Pasquale, E.B.: *EPH Receptor Signalling Casts a Wide Net on Cell Behaviour*, Nature Reviews Mol. Cell Biol. vol. 6, Jun. 2005, pp. 462-475.
Kullander, et al.: Mechanisms and Functions of EPH and EPHRIN signalling, Nature Reviews Mol. Cell Biol. vol. 3, Jul. 2002, pp. 475-486.
Noren, et al.: Eph receptor-ephrin bidirectional signals that target Ras and Rho proteins, Cell Signalling, vol. 16, 2004, pp. 655-666.
Landen, et al.: EphA2 as a target for ovarian cancer therapy, Expert Opinion on Therapeutic Targets, vol., 9, No. 6, 2005, pp. 1179-1187.

(Continued)

*Primary Examiner* — Christine J Saoud
*Assistant Examiner* — Jon M Lockard
(74) *Attorney, Agent, or Firm* — Lathrop & Gage LLP; James H. Velema, Esq.

(57) ABSTRACT

The present disclosure relates to an antibody or an epitope-binding fragment thereof that specifically binds to an EphA2 receptor. It further relates to a conjugate comprising a cytotoxic agent which is covalently bound to the antibody and a method for preparing such a conjugate.

25 Claims, 22 Drawing Sheets

(56) References Cited

U.S. PATENT DOCUMENTS

Figure 2:
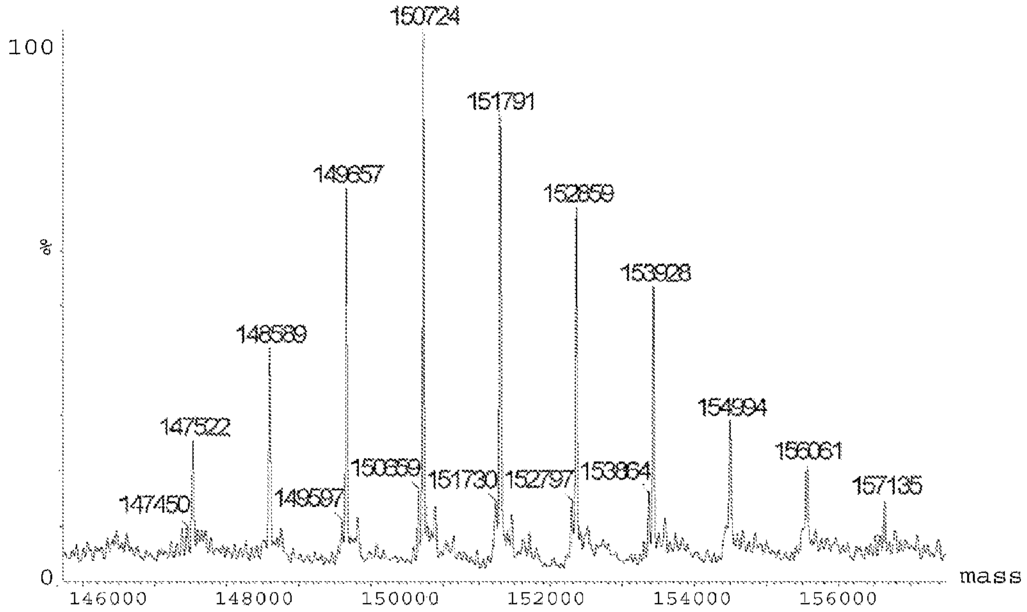

| | | | |
|---|---|---|---|
| 6,333,410 B1 | 12/2001 | Chari et al. | |
| 6,340,701 B1 | 1/2002 | Chari et al. | |
| 6,372,738 B2 | 4/2002 | Chari et al. | |
| 6,420,140 B1 | 7/2002 | Hori et al. | |
| 6,441,163 B1 | 8/2002 | Chari et al. | |
| 6,458,592 B1 | 10/2002 | Jakobovits et al. | |
| 6,534,660 B1 | 3/2003 | Yongxin et al. | |
| 6,586,618 B1 | 7/2003 | Zhao et al. | |
| 6,630,579 B2 | 10/2003 | Chari et al. | |
| 6,716,821 B2 | 4/2004 | Zhao et al. | |
| 6,756,397 B2 | 6/2004 | Zhao et al. | |
| 7,101,976 B1 | 9/2006 | Kilpatrick et al. | |
| 7,276,497 B2 | 10/2007 | Chari et al. | |
| 8,460,667 B2 * | 6/2013 | Blanc et al. | 424/143.1 |
| 2003/0055226 A1 | 3/2003 | Chari et al. | |
| 2003/0195365 A1 | 10/2003 | Zhao et al. | |

FOREIGN PATENT DOCUMENTS

| | | | |
|---|---|---|---|
| EP | 0332424 | A2 | 9/1989 |
| EP | 0338745 | A1 | 10/1989 |
| EP | 0 519 596 | A1 | 12/1992 |
| EP | 0 592 106 | A1 | 4/1994 |
| EP | 0629 240 | B1 | 12/1994 |
| EP | 1 331 266 | A1 | 3/2003 |
| EP | 1 498 490 | A1 | 1/2005 |
| EP | 1 498 491 | A1 | 1/2005 |
| EP | 1 676 910 | A1 | 7/2006 |
| EP | 1 792 987 | A1 | 6/2007 |
| EP | 1832577 | A1 | 9/2007 |
| EP | 1 272 527 | B1 | 12/2008 |
| FR | 1516743 | | 2/1968 |
| WO | WO89/09622 | A1 | 10/1989 |
| WO | WO90/02809 | A1 | 3/1990 |
| WO | WO 91/09967 | A1 | 7/1991 |
| WO | WO91/10737 | A1 | 7/1991 |
| WO | WO91/10741 | A1 | 7/1991 |
| WO | WO92/01047 | A1 | 1/1992 |
| WO | WO92/18619 | A1 | 10/1992 |
| WO | WO92/22324 | A1 | 12/1992 |
| WO | WO92/22653 | A1 | 12/1992 |
| WO | WO93/11236 | A1 | 6/1993 |
| WO | WO93/21319 | A1 | 10/1993 |
| WO | WO95/15982 | A2 | 6/1995 |
| WO | WO95/20401 | A1 | 8/1995 |
| WO | WO96/33735 | A1 | 10/1996 |
| WO | WO96/34096 | A1 | 10/1996 |
| WO | WO98/16654 | A1 | 4/1998 |
| WO | WO98/24893 | A2 | 6/1998 |
| WO | WO98/46645 | A1 | 10/1998 |
| WO | WO98/50433 | A2 | 11/1998 |
| WO | WO99/54342 | A1 | 10/1999 |
| WO | WO00/12507 | A1 | 3/2000 |
| WO | WO 01/12172 | A1 | 2/2001 |
| WO | WO00/12508 | A2 | 3/2002 |
| WO | WO03/074679 | A2 | 9/2003 |
| WO | WO 03/094859 | A2 | 11/2003 |
| WO | WO 2004/014292 | A2 | 2/2004 |
| WO | WO2004/029207 | A2 | 4/2004 |
| WO | WO 2004/092343 | A2 | 10/2004 |
| WO | WO2004/099249 | A2 | 11/2004 |
| WO | WO 2004/101764 | A2 | 11/2004 |
| WO | WO2005/085260 | A1 | 3/2005 |
| WO | WO2005/040170 | A1 | 5/2005 |
| WO | WO2006/019447 | A1 | 2/2006 |
| WO | WO 2006/023403 | A2 | 3/2006 |
| WO | WO2006/047350 | A2 | 5/2006 |
| WO | WO 2006/047637 | A1 | 5/2006 |
| WO | WO 2006/084226 | A2 | 8/2006 |
| WO | WO2006/105338 | A2 | 10/2006 |
| WO | WO 2007/030642 | A2 | 3/2007 |
| WO | WO2007/041635 | A2 | 4/2007 |
| WO | WO2007/085930 | A1 | 8/2007 |
| WO | WO2008/010101 | A1 | 1/2008 |
| WO | WO 2009/032661 | A1 | 3/2009 |

OTHER PUBLICATIONS

Zelinski, et al.: EphA2 Overexpression Causes Tumorigenesis of Mammary Epithelial Cells, Cancer Research, vol. 61, Mar. 1, 2001, pp. 2301-2306.

Ogawa et al.: The ephrin-A1 ligand and its receptor, EphA2, are expressed during tumor neovascularization, Oncogene, vol. 19, pp. 6043-6052 (2000).

Cheng, et al.: Blockade of EphA Receptor Tyrosine Kinase Activation Inhibits Vascular Endothelial Cell Growth Factor-Induced Angiogenesis, Mol. Cancer Res. vol. 1, Nov. 2002, pp. 2-11.

Cheng et al.: Inhibition of VEGF-Dependent Multistage Carcinogenesis by Soluble EphA Receptors, Neoplasia, vol. 5, No. 5, Sep.-Oct. 2003, pp. 445-456.

Dobrzanski et al.: Antiangiogenic and Antitumor Efficacy of EphA2 Receptor Antagonist, Cancer Research, vol. 64, Feb. 1, 2004, pp. 910-919.

Fang et al.: A kinase-dependent role for EphA2 receptor in promoting tumor growth and metastasis, Oncogene, vol. 24, 2005 pp. 7859-7868.

Dodge-Zantek: E-Cadherin Regulates the Function of the EphA2 Receptor Tyrosine Kinase, Cell Growth & Differentiation, vol. 10, Sep. 1999, pp. 629-638.

Padlan E.A.: A Possible Procedure for Reducing the Immunogenicity of Antibody Variable Domains While Preserving Their Ligand-Binding Properties, Molecular Immunology, vol. 28, No. 4/5, 1991, pp. 489-498.

Studnicka et al.: Human-engineered monoclonal antibodies retain full specific binding actvity by preserving non-CDR complementarity-modulating resdues, Protein Engineering, vol. 7, No. 6, 1994, pp. 805-814.

Roguska et al.: Humanization of murine monoclonal antibodies through variable domain resurfacing, PNAS, vol. 91, Feb. 1994, pp. 969-973.

Brinkmann et al.: Phage display of disulfide-stabilized Fv fragments, Journal of Immunological Methods, vol. 182, 1995, pp. 41-50.

Ames et al.: Conversion of murine Fabs isolated from a combinatorial phage display library to full length immunoglobulins, Journal of Immunological Methods, vol. 184, 1995, pp. 177-186.

Kettleborough et al.: Isolation of tumor cell-specific single-chain Fv from immunized mice using phage-antibody libraries and the reconstruction of whole antibodies from these antibody fragments, Eur. J. Immunol. vol. 24, 1994, pp. 952-958.

Persic et al.: An integrated vector system for the eukaryotic expression of antibodies or their fragments after selection from phage display libraries, Gene, vol. 187, 1997, pp. 9-18.

Burton et al.: Human Antibodies from Combinatorial Libraries, Advances in Immunology, vol. 57, pp. 191-280 (1994).

Mullinax et al.: Expression of a Heterodimeric Fab Antibody Protein in One Cloning Step, BioTechniques, vol. 12, No. 6, 1992, pp. 864-869.

Sawai et al.: Direct Production of the Fab Fragment Derived From the Sperm Immobilizing Antibody Using Polymerase Chain Reaction and cDNA Expression Vectors, AJRI vol. 34, 1995, pp. 26-34.

Better et al.: *Escherichia coli* Secretion of an Active Chimeric Antibody Fragment, Science, May 20, 1988, pp. 1041-1043.

Huston et al.: Protein Engineering of Single-Chain Fv Analogs and Fusion Proteins, Methods in Enzymology, vol. 203, 1991, pp. 46-88.

Shu et al.: Secretion of a single-gene-encoded immunoglobulin from myeloma cells, PNAS, vol. 90, Sept 1993, pp. 7995-7999.

Skerra et al.: Assembly of a Functional Immunoglobulin Fv Fragment in *Escherichia coli*, Science, vol. 240, 1988, pp. 1038-1040.

Pearson et al.: Improved tools for biological sequence comparison, PNAS, vol. 85, Apr. 1988.

Morrison et al.: Transfectomas Provide Novel Chimeric Antibodies, Science, vol. 229, 1985, pp. 1202-1207.

Oi et al.: Chimeric Antibodies, BioTechniques, vol. 4, No. 3, 1986, pp. 214-221.

(56) References Cited

OTHER PUBLICATIONS

Gillies et al.: High-level expression of chimeric antibodies using adapted cDNA variable region cassettes, J. of Immunological Methods, vol. 125, 1989, pp. 191-202.
Winter et al.: Man-made antibodies, Nature, vol. 349, Jan. 24, 1991, pp. 293-299.
Hudson, P.J.: Recombinant antibody constucts in cancer therapy, Current Opinion in Immunology, vol. 11, 1999, pp. 548-557.
Yang et al.: CDR Walking Mutagenesis for the Affinity Maturation of a Potent Human Ant-HIV-1 Antibody into the Picomolar Range, J. of Molecular Biology, vol. 254, 1995, pp. 392-403.
Rader et al.: A phage display approach for rapid antibody humanization: Designed combinatorial V gene libraries, PNAS, vol. 95, Jul. 1998, pp. 8910-8915.
Vaughan et al.: Human antibodies by design, Nature Biotechnology, vol. 16, Jun. 1998, pp. 535-539.
Adey et al.: Preparation of Second-Generation Phage Libraries, Phage Display of Peptides and Proteins, 1996, pp. 277-291.
Gram et al.: In vitro selection and affinity maturation of antibodies from a naïve combinatorial immunoglobulin library, PNAS, vol. 89, Apr. 1992, pp. 3576-3580.
Boder et al.: Directed evolution of antibody fragments with monovalent femtomolar antigen-binding affinity, PNAS, vol. 97, No. 20, Sep. 26, 2000, pp. 10701-10705.
Davies et al.: Affinity improvement of single antibody VH domains: residues in all three hypervariable regions affect antigen binding, Immunotechnology, vol. 2, 1996, pp. 169-179.
Thompson et al.: Affinity Maturation of a High-affinity Human Monoclonal Antibody Against the Third Hypervariable Loop of Human Immunodeficiency Virus: Use of Phage Display to Improve Affinity and Broaden Strain Activity, J. of Molecular Biology, vol. 256, 1996, pp. 77-88.
Short et al.: Complementary Combining Site Contact Residue Mutations of the Anti-digoxin Fab 26-10 Permit High Affinity Wild-type Binding, J. of Biol. Chem., vol. 277, No. 19, May 10, 2002, pp. 16365-16370.
Furukawa et al.: A Role of the Third Complementarity-determining Region in the Affinity Maturation of an Antibody, J. of Biol. Chem., vol. 276, No. 29, Jul. 20, 2001, pp. 27622-27628.
Thornton et al.: Prediction of progress at last, Nature, vol. 354, Nov. 14, 1991, pp. 105-106.
Shields et al.: High Resolution Mapping of the Binding Site on Human IgG1 for Fc gamma RI, Fc gamma RII, Fc gamma RIII, and FcRn and Design of IgG1 Variants with Improved Binding to the Fc gamma R, J. of Biol. Chem., vol. 276, No. 9, Mar. 2, 2001, pp. 6591-6604.
Junghans: Finally! The Brambell Receptor (FcRB), Immunological Research, vol. 16, No. 1, 1997, pp. 29-57.
Ghetie et al.: Multiple Roles for the Major Histocompatibility Complex Class I—Related Receptor FcRn, Annual Rev. Immunol., vol. 18, 2000, pp. 739-766.
Boyd et al.: The Effect of the Removal of Sialic Acid, Galactose and Total Carbohydrate on the Functional Activity of Campath-1H, Molecular Immunology, vol. 32, No. 17/18, 1995, pp. 1311-1318.
Raju et al: Glycoengineering of Therapeutic Glycoproteins: In Vitro Galactosylation and Sialylation of Glycoproteins with Terminal N-Acetylglucosamine and Galactose Residues, Biochemistry, vol. 40, 2001, pp. 8868-8876.
Zhang et al.: A New Strategy for the Synthesis of Glycoproteins, Science, vol. 303, Jan. 16, 2004, pp. 371-373.
Sears et al.: Toward Automated Synthesis of Oligosaccharides and Glycoproteins, Science vol. 291, Mar. 23, 2001, pp. 2344-2350.
Wacker, et al: N-Linked Glycosylation in Campylobacter jejuni and its Functional Transfer into *E. coli*, Science, vol. 298, Nov. 29, 2002, pp. 1790-1793.
Davis, B.G.: Synthesis of Glycoproteins, Chem. Rev. vol. 102, 2002, pp. 579-601.
Hang, et al.: Chemoselective Approaches to Glycoprotein Assembly, Acc. Chem. Res. vol. 34, No. 9, 2001 pp. 727-736.
Lazar, et al.: Engineered antibody Fc variants with enhanced effector function, PNAS, vol. 103, No. 11, Mar. 14, 2006, pp. 4005-4010.
Okazaki, et al.: Fucose Depletion from Human IgG1 Oligosaccharide Enhances Binding Enthalpy and Association Rate Between IgG1 and Fc gamma RIIIa, J. Mol. Biol., vol. 336, 2004, pp. 1239-1249
Shinkawa, et al.: The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity, J. of Biol. Chem., vol. 278, No. 5, Jan. 31, 2003, pp. 3466-3473.
Ferrara, et al.: The Carbohydrate at Fc gamma RIIIa Asn-162, J. of Biol. Chem, vol. 281, No. 8, Feb. 24, 2006, pp. 5032-5036
Ferrara, et al.: Modulation of Therapeutic Antibody Effector Functions by Glycosylation Engineering: Influence of Golgi Enzyme Localization Domain and Co-Expression of Heterologous Beta1, 4-N-acetylglucosaminyltransferase III and Golgi alpha-mannosidase II, Biotechnology and Bioengineering, vol. 93, No. 5, Apr. 5, 2006, pp. 851-861.
Koumenis, et al.: Modulating pharmacokinetics of an anti-interleukin-8 F(ab')2 by amine-specific PEGylation with preserved bioactivity, International Journal of Pharmaceutics, vol. 198, 2000, pp. 83-95.
Parham, P.: On the Fragmentation of Monoclonal IgG1, IgG2a, and IgG2b From BALB/c Mice, J. of Immunology, vol. 131, No. 6, Dec. 1983, pp. 2895-2902.
Nisonoff, et al.: Separation of Univalent Fragments from the Bivalent Rabbit Antibody Molecule by Reduction of Disulfide Bonds, Archives of Biochemistry and Biophysics, vol. 89, 1960, pp. 230-244.
Wang, et al.: Fractionation of monoclonal antibody aggregates using membrane chromatography, J. of Membrane Science, vol. 318, 2008, pp. 311-316.
Cromwell, et al.: Protein Aggregation and Bioprocessing, AAPS Journal, vol. 8, No. 3, 2006, pp. E572-E579.
Litzén, et al.: Separation and Quantification of Monoclonal Antibody Aggregates by Asymmetrical Flow Field-Flow Fractionation and Comparison to Gel Permeation Chromatography, Analytical Biochemistry, vol. 212, 1993, pp. 469-480.
Tozuka, Z.: Studies on Tomaymycin, II Total Syntheses of the Antitumor Antibiotics E- And Z-Tomaymycins, J. Antibiotics, vol. 36, 1983, pp. 276-282.
Carlsson, et al.: Protein Thiolation and Reversible Protein—Protein Conjugation, Biochem. J., vol. 173, 1978, pp. 723-737.
Liu, et al.: Eradication of large colon tumor xenografts by targeted delivery of maytansinoids, PNAS, vol. 93, 1996, pp. 8618-8623.
Goldmacher, et al.: Antibody-Complement-Mediated Cytotoxicity is Enhanced by Ribosome-Inactivating Proteins, J. Immunol. vol. 135, No. 6, Dec. 1985, pp. 3648-3651.
Goldmacher, et al.: Evidence That Pinocytosis in Lymphoid Cells Has a Low Capacity, J. Cell Biol., vol. 102, Apr. 1986, pp. 1312-1319.
Reynolds, et al.: The Chemistry, Mechanism of Action and Biological Properties of CC-1065, A Potent Antitumor Antibiotic, J. Antibiotics, vol. XXXIX 1986, pp. 319-334.
Warpehoski, et al.: Stereoelectronic Factors Influencing the Biological Activity and DNA Interaction of Synthetic Antitumor Agents Modeled on CC-1065, J. Med. Chem., vol. 31, 1988, pp. 590-603.
Boger, et al.: Synthesis of N-(tert-Butyloxycarbonyl)-CBI, CBI, CBI-CDPI1 and CBI-CDPI2: Enhanced Functional Analogues of CC-1065 Incorporating the 1,2,9,9a-Tetrahydrocycloproa[c]benz[e]indol-4-one (CBI) Left-Hand Subunit, J. Org. Chem., vol. 55, 1990, pp. 5823-5832.
Boger, et al.: Synthesis and Preliminary Evaluation of (+)-CBI-Indole2: An Enhanced Functional Analog of (+)- CC-1065, Bioorganic & Medicinal Chemistry Letters, vol. 1, No. 2, 1991, pp. 115-120.
Foster, et al.: Phase I trial of Adozelesin using the treatment schedule of daily x5 every 3 weeks, Investigational New Drugs vol. 13, 1996, pp. 321-326.

(56) References Cited

OTHER PUBLICATIONS

Wolff, et al.: Phase I Clinical and Pharmocokinetic Study of Carzelesin (U-80244) Given Daily for Five Consecutive Days Clinical Cancer Research, vol. 2, Oct. 1996, pp. 1717-1723.

Chari, et al.: Enhancement of the Selectivity and Antitumor Efficacy of a CC-1065 Analogue through Immunoconjugate Formation, Cancer Research, vol. 55, Sep. 15, 1995, pp. 4079-4084.

Sanofi, et al.: Antibodies That Specifically Bind to the Epha2 Receptor, International Search Report for WO2011/039724A1.

Mori, et al.: Total Syntheses of Prothracarcin and Tomaymycin by Use of Palladium Catalyzed Carbonvlation, Tetrahedron, vol. 42, 1986, pp. 3793-3806.

* cited by examiner

Fig. 1A

SEQ ID NO: 1

AYYMH

SEQ ID NO: 2

LVNPYNGFSSYNQKFQG

SEQ ID NO: 3

EFYGYRYFDV

SEQ ID NO: 4

KSSQSLIHSDGRTYLN

SEQ ID NO: 5

LVSRLDS

SEQ ID NO: 6

WQGSHFPRT

SEQ ID NO: 7

GAGGTCCAGCTGCAACAGTCTGGACCTGAGCTGGTGAAGCCTGGGGCTTCAG
TGAAGATTTCCTGCAAGGCTTCTGGTTACTCATTCACTGCCTACTACATGCACT
GGGTGAAGCAAAGTCATGTAAAGAGTCTTGAGTGGATTGGACTTGTTAATCCT
TACAATGGTTTTAGTAGCTACAACCAGAATTTCGAGGACAAGGCCAGCTTGAC
TGTAGATAGATTCTCCAGCACCGCCTACATGGAACTCCACAGCCTGACATCTG
AGGACTCTGCAGTCTATTACTGTGCAAGAGAATTCTACGGCTACCGGTACTTC
GATGTCTGGGGCGCAGGGACCGCGGTCACCGTCTCCTCA

Fig. 1B

SEQ ID NO: 9

GATGTTGTGATGACCCAGACTCCACTCACTTTGTCGGTTACCATTGGACAA
CCAGCCTCCATCTCTTGCAAGTCAAGTCAGAGCCTCATACATAGTGATGGA
AGAACATATTTGAATTGGTTGTTACAGAGGCCAGGCCAGTCTCCAAAGCGC
CTAATTTATCTGGTGTCTAGACTGGACTCTGGAGTCCCTGACAGGTTCACT
GGCAGTGGATCAGGGACAGATTTCACACTGAAAATCAGCAGAGTGGAGGC
TGAGGATTTGGGAGTTTATTATTGCTGGCAAGGTTCACATTTTCCTCGGAC
GTTCGGTGGAGGCACCAAGCTGGAAATCAAACGG

SEQ ID NO:11

CAGGTGCAACTGGTGCAATCCGGTGCCGAGGTCGTCAAACCCGGAGCATC
TGTGAAGATATCCTGTAAGGCCTCCGGCTACACTTTTACAGCCTACTATAT
GCATTGGGTTAAACAGAGTCCCGTGCAGTCCCTGGAATGGATCGGCTTGG
TGAACCCTTATAACGGATTCTCAAGTTACAATCAAAAGTTTCAGGGCAAGG
CTTCCCTGACTGTAGACAGATCTAGTTCCACAGCCTACATGGAGCTCCATT
CACTGACATCAGAAGACAGCGCCGTATACTATTGCGCACGTGAGTTCTACG
GCTATAGATACTTTGACGTCTGGGGCCAAGGCACAGCCGTCACAGTGAGC
TCT

SEQ ID NO:13

GACGTCGTGATGACACAAACCCCTCTGTCCCTGAGCGTCACTCTGGGACA
ACCCGCTTCCATTAGCTGCAAATCATCACAATCTCTCATCCACTCAGACGG
CCGTACGTACCTCAATTGGCTGCTGCAGAGACCAGGACAGTCCCCTAAAA
GGCTTATCTACCTGGTCTCTCGTTTGGACTCTGGTGTACCAGACCGGTTTA
CTGGTTCCGGGGCCGGAACCGATTTCACTCTGAAGATTTCCAGGGTGGAA
GCTGAAGATCTCGGAGTGTATTATTGCTGGCAGGGCAGCCATTTCCCCCG
TACTTTTGGTGGGGGTACCAAATTGGAAATTAAG

Fig. 1C

SEQ ID NO: 15 atgggatggtcttgcatcatcctgtttctcgtggctactgccaccggagtgcacagtgacgtcgtgatgacacaaaccc
ctctgtccctgagcgtcactctgggacaacccgcttccattagctgcaaatcatcacaatctctcatccactcagacgg
ccgtacgtacctcaattggctgctgcagagaccaggacagtcccctaaaaggcttatctacctggtctctcgtttggac
tctggtgtaccagaccggtttactggttccggggccggaaccgatttcactctgaagatttccagggtggaagctgaa
gatctcggagtgtattattgctggcagggcagccatttcccccgtacttttggtgggggtaccaaattggaaattaagc
gtacggtggctgcaccatctgtcttcatcttcccgccatctgatgagcagttgaaatctggaactgcctctgttgtgtgcct
gctgaataacttctatcccagagaggccaaagtacagtggaaggtggataacgccctccaatcgggtaactccca
ggagagtgtcacagagcaggacagcaaggacagcacctacagcctcagcagcaccctgacgctgagcaaagc
agactacgagaaacacaaagtctacgcctgcgaagtcacccatcagggcctgagctcgcccgtcacaaagagct
tcaacaggggagagtgttag

SEQ ID NO: 17 atgggatggtcctgtattattctgtttctcgtggctacagccacaggcgttcatagtcaggtgcaactggtgcaatccggt
gccgaggtcgtcaaacccggagcatctgtgaagatatcctgtaaggcctccggctacacttttacagcctactatatg
cattgggttaaacagagtcccgtgcagtccctggaatggatcggcttggtgaacccttataacggattctcaagttaca
atcaaaagtttcagggcaaggcttccctgactgtagacagatctagttccacagcctacatggagctccattcactga
catcagaagacagcgccgtatactattgcgcacgtgagttctacggctatagatactttgacgtctggggccaaggc
acagccgtcacagtgagctctgcttccactaagggcccatcggtcttccccctggcaccctcctccaagagcacctct
gggggcacagcggcccctgggctgcctggtcaaggactacttccccgaaccggtgacggtgtcgtggaactcaggc
gccctgaccagcggcgtgcacaccttcccggctgtcctacagtcctcaggactctactccctcagcagcgtggtgac
cgtgccctccagcagcttgggcacccagacctacatctgcaacgtgaatcacaagcccagcaacaccaaggtgg
acaagaaagttgagcccaaatcttgtgacaaaactcacacatgcccaccgtgcccagcacctgaactcctggggg
gaccgtcagtcttcctcttccccccaaaacccaaggacaccctcatgatctcccggacccctgaggtcacatgcgtg
gtggtggacgtgagccacgaagaccctgaggtcaagttcaactggtacgtggacggcgtggaggtgcataatgcc
aagacaaagccgcgggaggagcagtacaacagcacgtaccgtgtggtcagcgtcctcaccgtcctgcaccagg
actggctgaatggcaaggagtacaagtgcaaggtctccaacaaagccctcccagcccccatcgagaaaaccatc
tccaaagccaaagggcagccccgagaaccacaggtgtacaccctgcccccatcccgggatgagctgaccaaga
accaggtcagcctgacctgcctggtcaaaggcttctatcccagcgacatcgccgtggagtgggagagcaatgggc
agccggagaacaactacaagaccacgcctcccgtgctggactccgacggctccttcttcctctacagcaagctcac
cgtggacaagagcaggtggcagcaggggaacgtcttctcatgctccgtgatgcatgaggctctgcacaaccacta
cacgcagaagagcctctccctgtctccgggttga

Fig. 11

SEQ ID NO: 19

QGKEVVLLDF AAAGGELGWL THPYGKGWDL MQNTMNDMPT YMYSVCNVMS
GDQDNWLRTN WVYRGEAERI FIELKFTVRD CNSFPGGASS CKETFNLYYA
ESDLDYGTNF QKRLFTKIDT IAPDEITVSS DFEARHVKLN VEERSVGPLT
RKGFYLAFQD IGACVALLSV RVYYKKCPEL LQGLAHFPET IAGSDAPSLA
TVAGTCVDHA VVPPGGEEPR MHCAVDGEWL VPIGQCLCQA GYEKVEDACQ
ACSPGFFKFE ASESPCLECP EHTLPSPEGA TSCECEEGFF RAPQDPASMP
CTRPPSAPHY LTAVGMGAKV ELRWTPPQDS GGREDIVYSV TCEQCWPESG
ECGPCEASVR YSEPPHGLTR TSVTVSDLEP HMNYTFTVEA RNGVSGLVTS
RSFRTASVSI NQTEPPKVRL EGRSTTSLSV SWSIPPPQQS RVWKYEVTYR
KKGDSNSYNV RRTEGFSVTL DDLAPDTTYL VQVQALTQEG QGAGSKVHEF
QTLSPEGSGN

ANTIBODIES THAT SPECIFICALLY BIND TO THE EPHA2 RECEPTOR

The present invention relates to an antibody or an epitope-binding fragment thereof that specifically binds to an EphA2 receptor.

It further relates to a conjugate comprising a cytotoxic agent that is covalently bound to the antibody and a method for preparing such a conjugate.

BACKGROUND OF THE INVENTION

Cancer is a disease characterized by uncontrolled proliferation, resulting from aberrant signal transduction. The most dangerous forms of cancer are malignant cells which have the ability to spread, either by direct growth into adjacent tissue through invasion, or by implantation into distant sites by metastasis. Metastatic cells have acquired the ability to break away from the primary tumor, translocate to distant sites through the bloodstream or lymphatic system, and colonize distant and foreign microenvironments.

It is now clear that the Eph molecules are involved in disease states such as cancer. Eph receptors are a unique family of receptor tyrosine kinases (RTK), the largest in the genome, consisting of fourteen receptors, divided into two groups A and B, that interact with eight membrane-bound ephrin ligands (Pasquale, E. B. et al., 2005, *Nature Reviews Mol. Cell. Biol.,* 6: 462-475). Binding of Eph receptors to their ligands induces receptor clustering, activation of kinase activity, and subsequent trans-phosphorylation of the cytoplasmic domains on tyrosine residues, creating docking sites for a number of signaling proteins (Kullander, K. and Klein, R., 2002, *Nature Reviews Mol. Cell. Biol.,* 3: 475-486; Noren, N. K. and Pasquale, E. B., 2004, *Cell signal.,* 16: 655-666).

Overexpression of the EphA2 receptor has been reported in cancers of the ovary, breast, prostate, lung, colon, oesophagus, renal cell, cervix, and melanoma. EphA2 was suggested to be a positive regulator of cell growth and survival in malignant cells (Landen, C. N. et al., 2005, *Expert. Opin. Ther. Targets,* 9 (6): 1179-1187). A role for EphA2 in cancer has also been described, since EphA2 overexpression alone is sufficient to transform mammary epithelial cells into a malignant phenotype (Zelinski et al., 2001, *Cancer Res.,* 61: 2301-2306), and increases spontaneous metastasis to distant sites (Landen, C. N. et al., 2005, *Expert. Opin. Ther. Targets,* 9 (6): 1179-1187). Furthermore, increasing evidence suggests that EphA2 is involved in tumor angiogenesis (Ogawa et al., 2000, *Oncogene,* 19: 6043-6052; Cheng et al. 2002, *Mol. Cancer. Res.,* 1: 2-11; Cheng et al., 2003, *Neoplasia,* 5 (5): 445-456; Dobrzanski et al., 2004, *Cancer Res.,* 64: 910-919).

Phosphorylation of EphA2 has been shown to be linked to its abundance. Tyrosine phosphorylated EphA2 is rapidly internalized and fated for degradation, whereas unphosphorylated EphA2 demonstrates reduced turnover and therefore accumulates at the cell surface. It is currently thought that this kind of model might contribute to the high frequency of EphA2 overexpression in cancer (Landen, C. N. et al., 2005, *Expert. Opin. Ther. Targets,* 9 (6): 1179-1187). However, reality may be more complex, since recent data seem to indicate a role for EphA2 kinase-dependent and -independent functions in tumor progression (Fang W. B., 2005, *Oncogene,* 24: 7859-7868).

Agonistic antibodies have been developed which promote EphA2 tyrosine phosphorylation and internalization, ultimately resulting in inhibition of tumor cell growth (Dodge-Zantek et al., 1999, *Cell Growth & Differ.,* 10: 629-638; WO 01/12172, WO 03/094859, WO 2004/014292, WO 2004/101764, WO 2006/023403, WO 2006/047637, WO 2007/030642).

Application WO 2006/084226 discloses antibodies which neither increase nor decrease EphA2 kinase activity but are capable of impeding tumor cell proliferation. However, there is no indication therein that these antibodies prevent ephrinA1 binding to the receptor and inhibit ephrinA1-induced EphA2 phosphorylation. The use of antagonistic antibodies has been proposed in WO 2004/092343, but no actual antibody was disclosed therein. Antibodies recognizing EphA2 which are genuine antagonists have been described in WO 2008/010101, as well as humanized variants and conjugates thereof. These antibodies and derivatives thereof inhibit EphA2 kinase-dependent tumor cell growth.

Nevertheless, there is still a need for novel and efficacious medicaments which can be used in cancer therapy.

SUMMARY OF THE INVENTION

It is an object of the invention to provide new agents that specifically bind to class A Eph receptor family members, such as EphA2, and inhibit the cellular activity of the receptor by antagonizing the receptor. Thus, the present invention includes antibodies or fragments thereof that recognize the EphA2 receptor, preferably human, and function as antagonists of said receptor. These antibodies are devoid of any agonist activity.

In one embodiment, the antibody or an epitope-binding fragment thereof of the present invention comprises at least one heavy chain and at least one light chain, said heavy chain comprising three sequential complementarity-determining regions having amino acid sequences represented by SEQ ID NOS: 1, 2, and 3, and said light chain comprising three sequential complementarity-determining regions having amino acid sequences represented by SEQ ID NOS: 4, 5, and 6. In a preferred embodiment, said antibody or epitope-binding fragment thereof is a humanized or resurfaced. In an even more preferred embodiment, the heavy chain of said antibody or epitope-binding fragment thereof comprises an amino acid sequence consisting of SEQ ID NO: 12, and the light chain of said antibody or epitope-binding fragment thereof comprises an amino acid sequence consisting of SEQ ID NO: 14.

In a further embodiment the heavy chain of said antibody has an amino acid sequence SEQ ID NO: 18, and the light chain of said antibody has an amino acid sequence SEQ ID NO: 16.

In another embodiment, the said antibody or epitope-binding fragment thereof is conjugated to a cytotoxic agent. It is therefore an aspect of this invention to provide a conjugate of an antibody of the present invention or an epitope-binding fragment thereof, wherein said conjugate comprises a bound cytotoxic agent chosen between: the compound of formula (XIII):

(XIII)
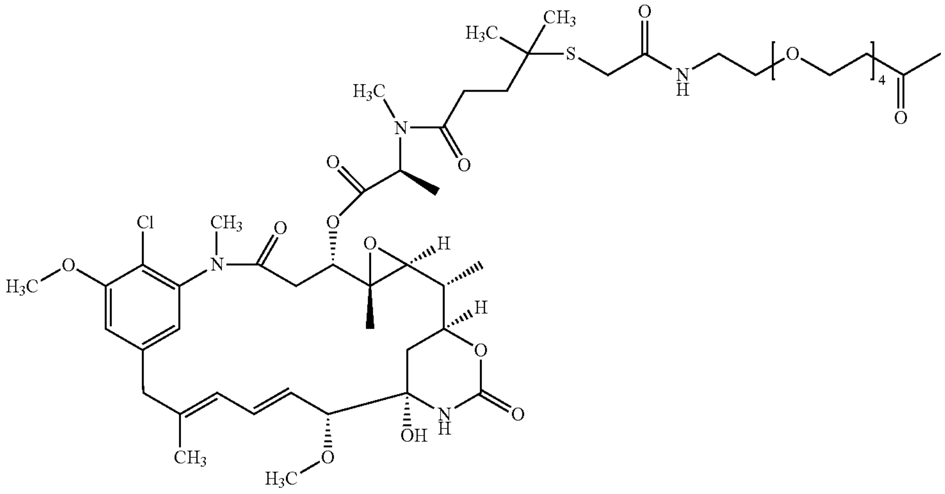
the compound of formula (XIV):
(XIV)
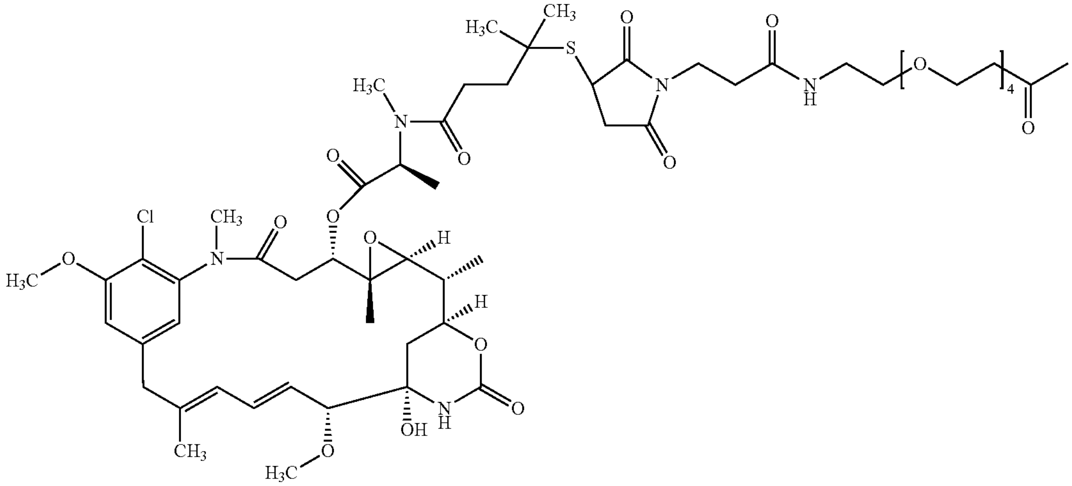
the compound of formula (XXIV):
(XXIV)
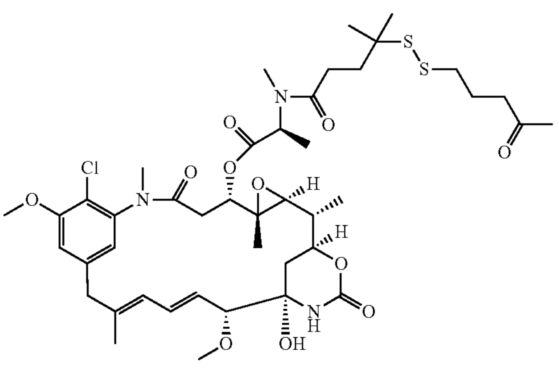

the compound of formula (XXV):
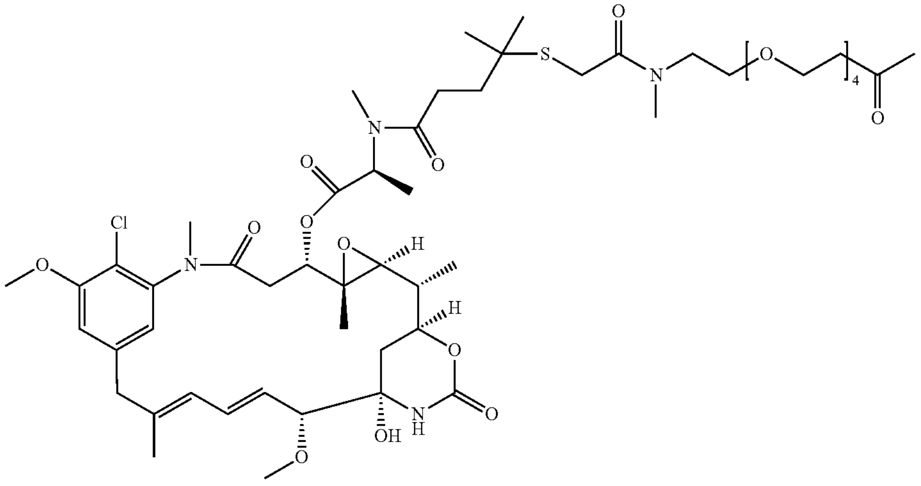
(XXV)
the compound of formula (XXVI):
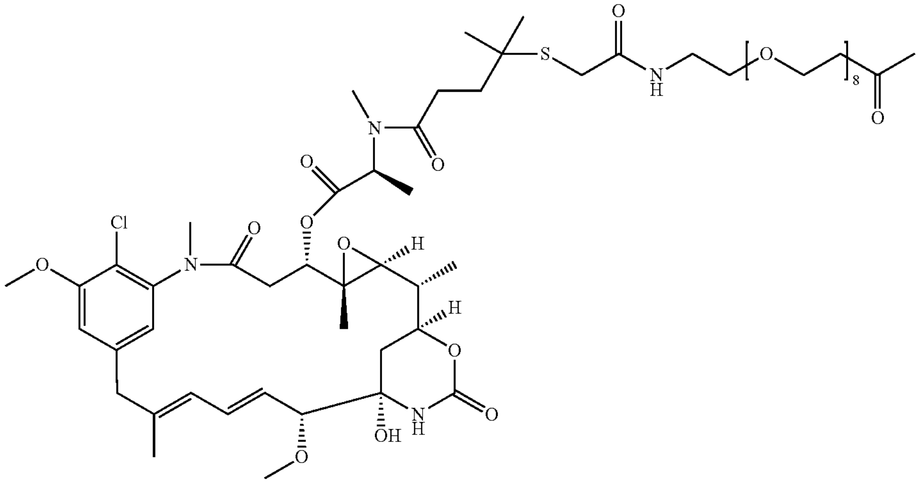
(XXVI)
and
the compound of formula (XXVII):
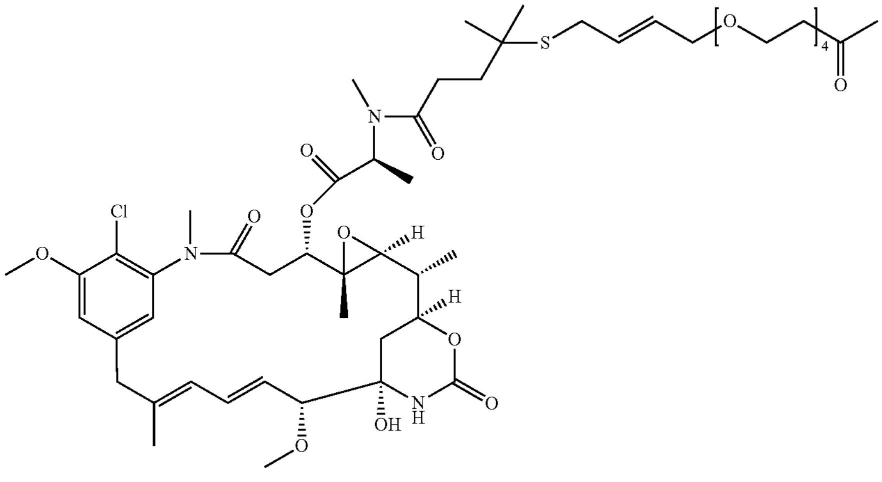
(XXVII)

In a preferred embodiment, the conjugate comprises the compound of formula (XIII) as the cytotoxic agent. In a further preferred embodiment, the number of maytansinoid molecules bound per antibody molecule (DAR) in said conjugate is comprised between 4 and 7 maytansinoid molecules/antibody molecule, said DAR being determined by measuring spectrophotometrically the ratio of the absorbance at 252 nm and 280 nm.

In another aspect, it is provided a method for preparing a conjugate which comprises the steps of:

(i) bringing into contact an optionally-buffered aqueous solution of a cell-binding agent with a solution of a cytotoxic compound;

(ii) then optionally separating the conjugate which was formed in (i) from the unreacted reagents and any aggregate which may be present in the solution;

wherein the cell-binding agent is an antibody according to claims 1-3, and a cytotoxic agent chosen between:

the compound of formula (XVII):

(XVII)

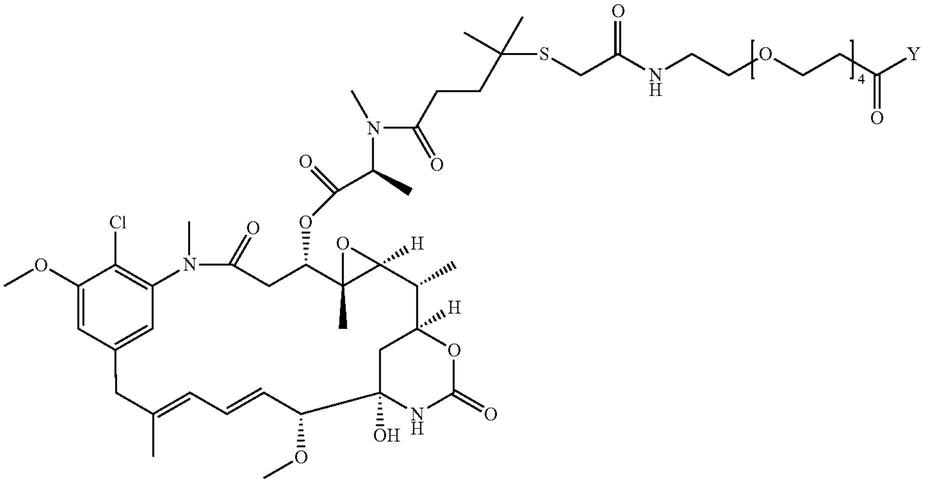

wherein Y is N-succinimidyloxy, N-sulfosuccinimidyloxy, N-phthalimidyloxy, N-sulfophthalimidyloxy, 2-nitrophenyloxy, 4-nitrophenyloxy, 2,4-dinitrophenyloxy, 3-sulfonyl-4-nitrophenyloxy, 3-carboxy-4-nitrophenyloxy, imidazolyl, or halogen atom; and the compound of formula (XVIII):

(XVIII)

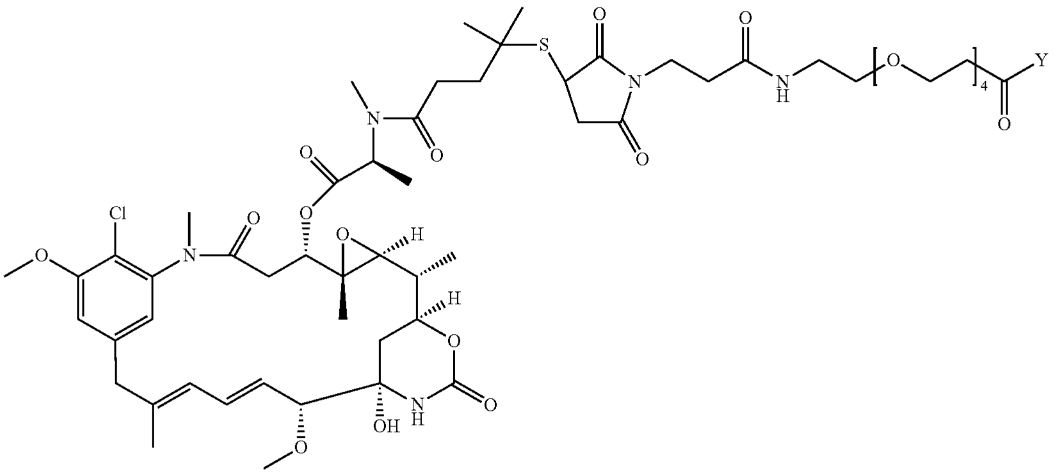

wherein Y is N-succinimidyloxy, N-sulfosuccinimidyloxy, N-phthalimidyloxy, N-sulfophthalimidyloxy, 2-nitrophenyloxy, 4-nitrophenyloxy, 2,4-dinitrophenyloxy, 3-sulfonyl-4-nitrophenyloxy, 3-carboxy-4-nitrophenyloxy, imidazolyl, or halogen atom.

Conjugates obtainable by said method are comprised within the scope of this invention. In particular, such conjugate have a structure chosen between the structures of the formula (XV):

jugated to a cytotoxic agent, shows more potency and is more selective at killing tumor cells expressing EphA2 than the conjugates of the prior art. In addition, the conjugates of the present invention display advantageous pharmacokinetic properties over the conjugates of the prior art, such as a slower clearance, a better exposure, and an increased stability of the conjugate in vivo. Such properties would be particularly useful, along with the high cytotoxic efficacy and selectivity, for developing a medicament which is both safe and efficacious.

(XV)

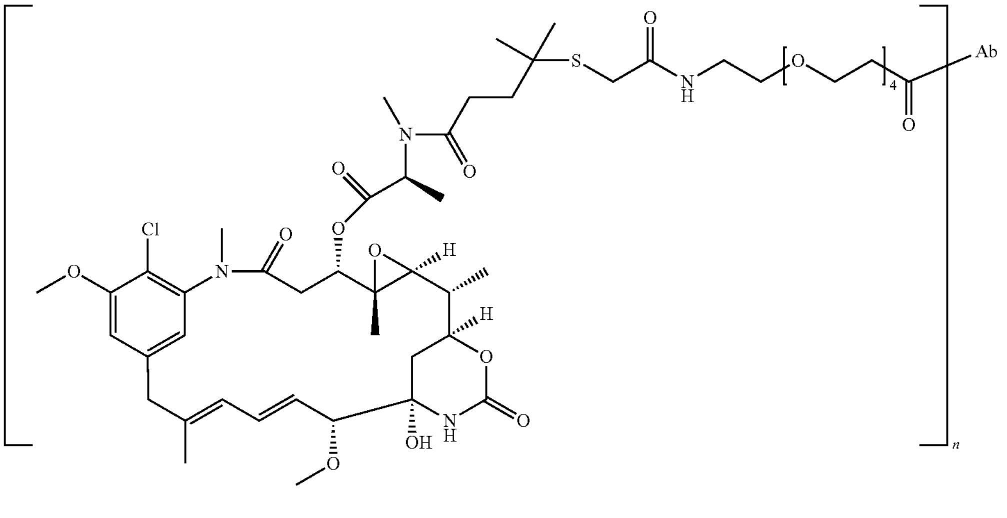

and of the formula (XVI):

(XVI)

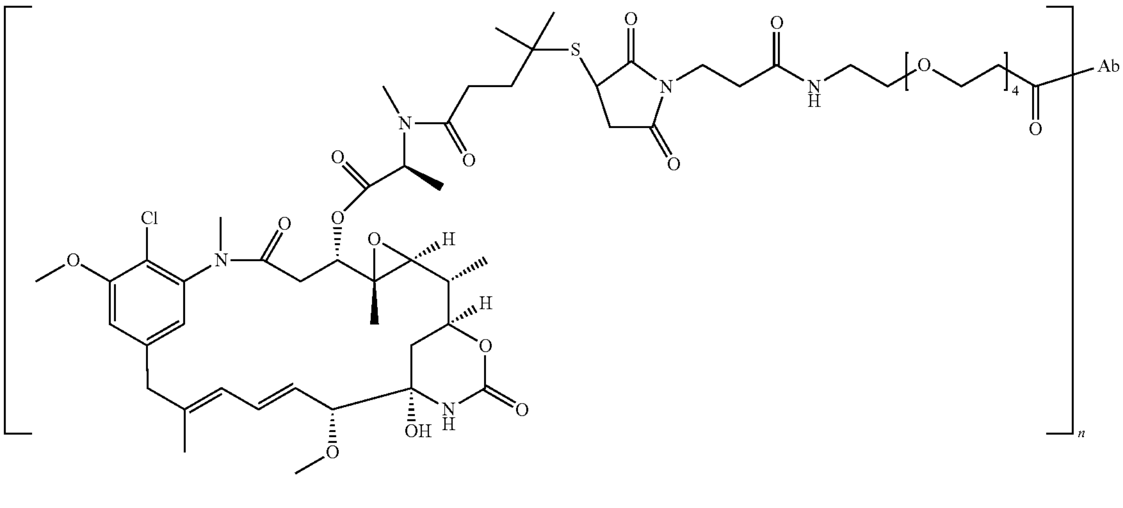

wherein Ab is an antibody according to the present invention and n is an integer comprised between 1 and 15. In a preferred embodiment, n is comprised between 4 and 7. In another preferred embodiment, the conjugate of the invention has the structure of the formula (XV).

The affinity of the antibody of the invention or epitope-binding fragment thereof for the antigen is not affected by the conjugation process; on the other hand, conjugation of a cytotoxic agent to antibodies of the prior art results in a decreased affinity for EphA2. The said antibody or epitope-binding fragment thereof of the present invention, when con- Therefore, the invention encompasses a pharmaceutical composition containing an antibody of the invention or epitope-binding fragment thereof, or a conjugate thereof, and a pharmaceutically acceptable carrier or excipient. The antibodies of the invention or epitope-binding fragments thereof, or conjugates thereof, can be used as a medicament. In particular, they can be used to make a medicament to treat cancer. In a preferred embodiment, the said cancer is chosen between carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma, rhabdomyosarcoma and osteosarcoma; other tumors, including melanoma, seminoma, teratocarcinoma, thyroid follicular cancer, xeroderma pigmentosum, keratoactanthoma; tumors of the central and peripheral nervous system, including astrocytoma, neuroblastoma, glioma, and schwannomas.

FIGURE LEGENDS

FIG. 1: Sequences of the CDR, the $V_H$ and the $V_L$ of mu2H11R35R74, and of the $V_H$ and the $V_L$ of hu2H11R35R74.

FIG. 2: HRMS spectrum of hu2H11R35R74-PEG4-NHAc-DM4 using method C (example 1a.1.)

Figure 3:
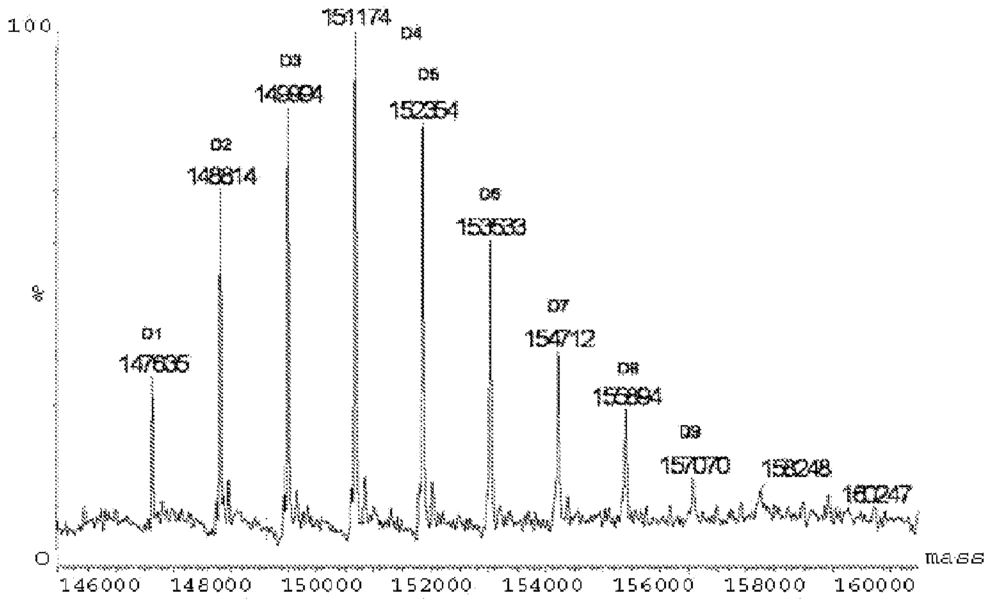

FIG. 3: HRMS spectrum of hu2H11R35R74-PEG4-Mal-DM4 using method C (example 1b.1.)

Figure 4:
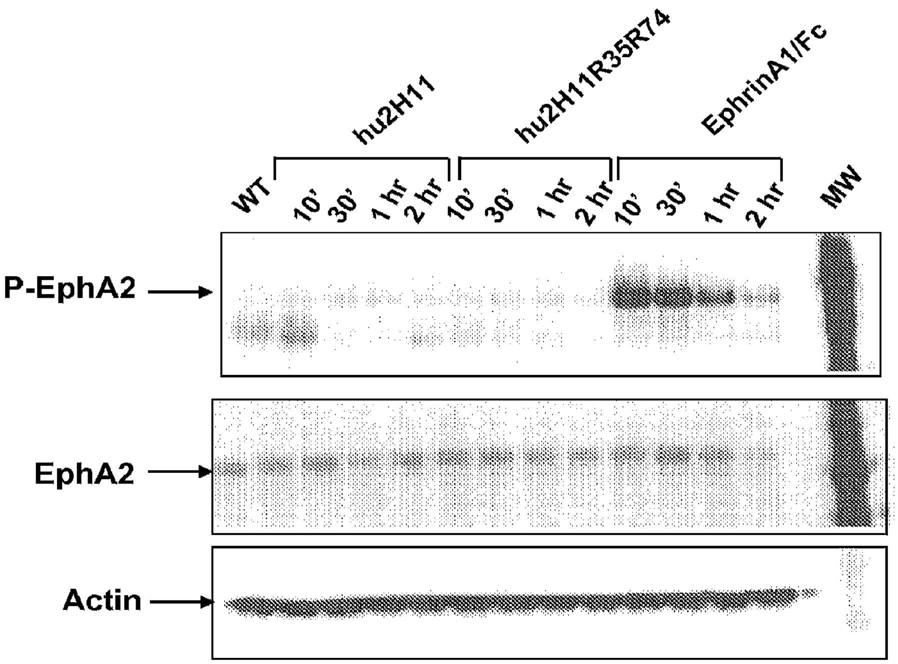

FIG. 4: Kinetics analysis of the phosphorylation of EphA2 in MDA-MB-231 cells. WT: wild type untreated cells; MW: molecular weight marker; P-EphA2: phosphorylated Epha2

Figure 5A:
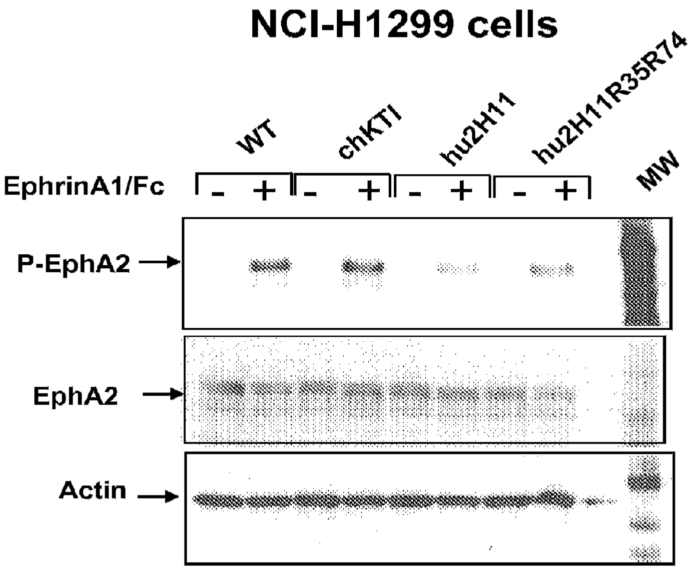
Figure 5B:
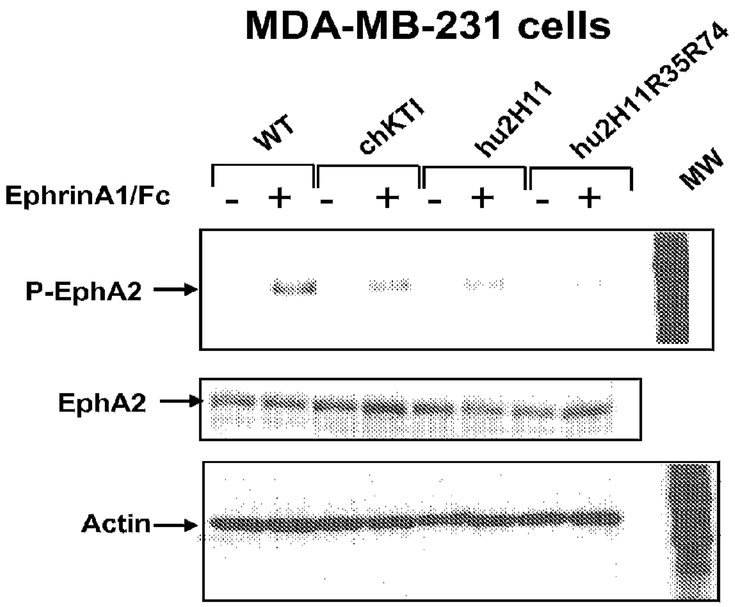

FIGS. 5A and 5B: Inhibition of the phosphorylation of EphA2 after induction by EphrinA1/Fc respectively on NCI-H1299 cells (5A) and MDA-MB-231 cells (5B); WT: wild type untreated cells; MW: molecular weight marker; P-EphA2: phosphorylated EphA2.

Figure 6:
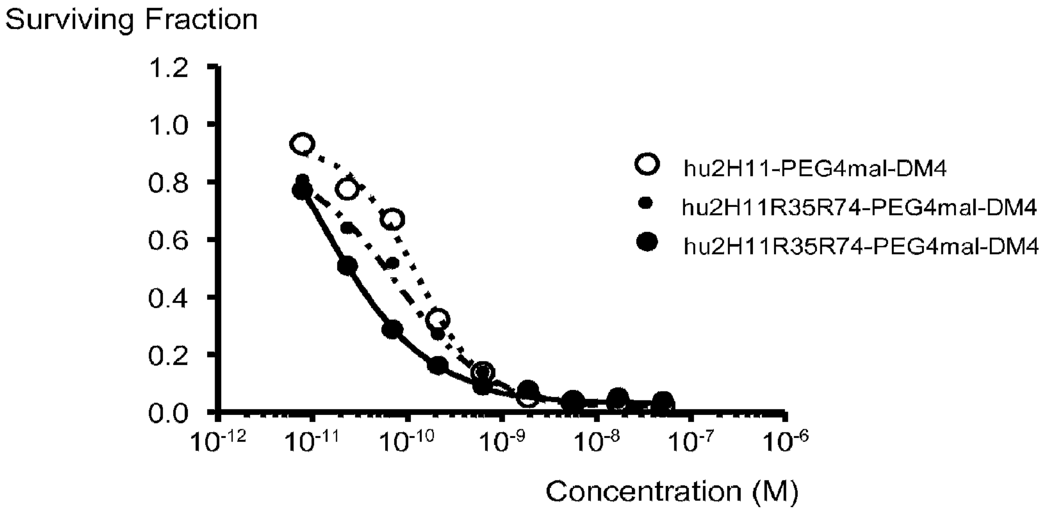

FIG. 6: Cytotoxic activity of hu2H11R35R74-PEG4-Mal-DM4 (small filled circles: DAR=6.7; large filled circles: DAR=7.0) as compared to hu2H11-PEG4-Mal-DM4.

Figure 7:
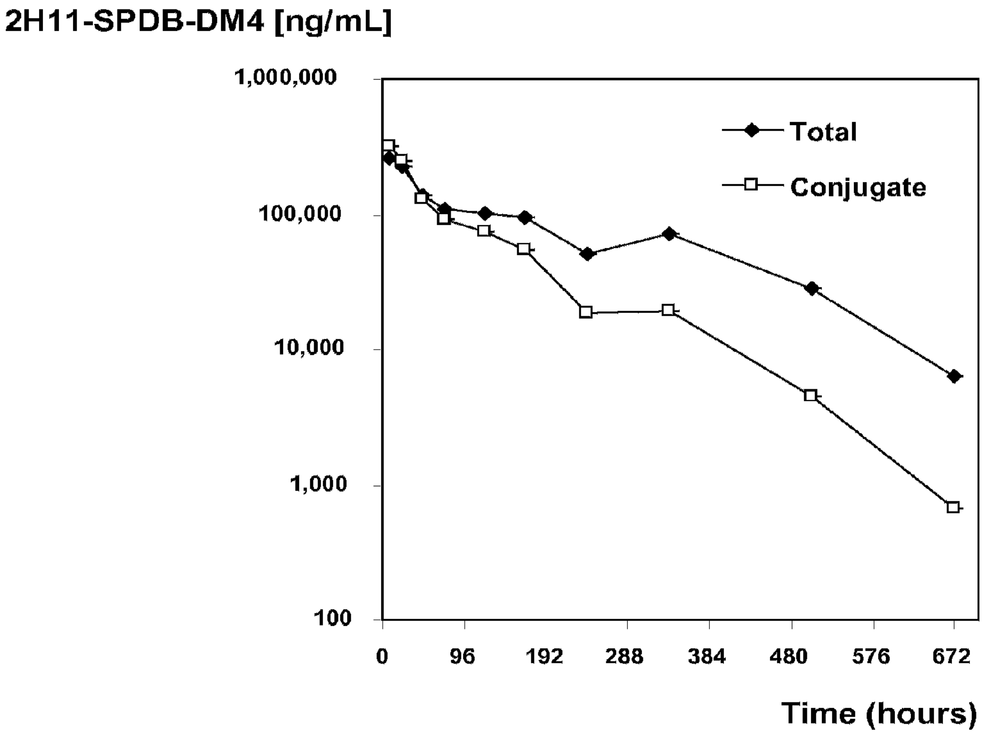

FIG. 7: Time plot (semi-logarithmic scale) representation of the mean plasma concentrations (n=2) of hu2H11-SPDB-DM4 after a single dose intravenous administration of 20 mg/kg of immunoconjugate in HGS to male CD-1 mice. The total concentration of human IgG (filled diamonds) and the conjugate fraction (open squares) are shown.

Figure 8:
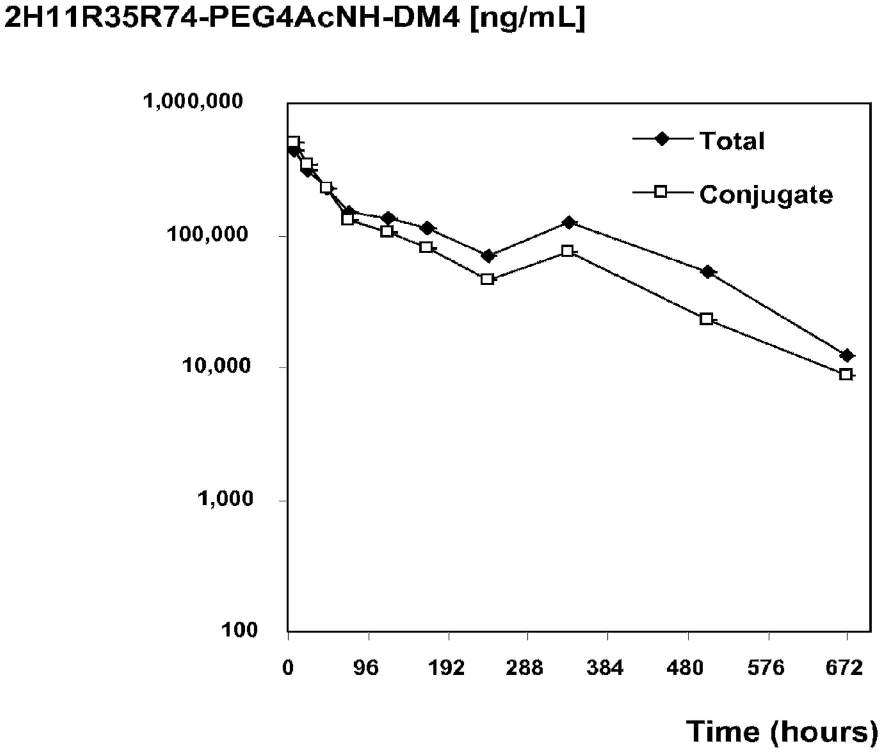

FIG. 8: Time plot (semi-logarithmic scale) representation of the mean plasma concentrations (n=2) of hu2H11R35R74-PEG4-NHAc-DM4 after a single dose intravenous administration of 20 mg/kg of immunoconjugate in HGS to male CD-1 mice. The total concentration of human IgG (filled diamonds) and the conjugate fraction (open squares) are shown.

Figure 9A:
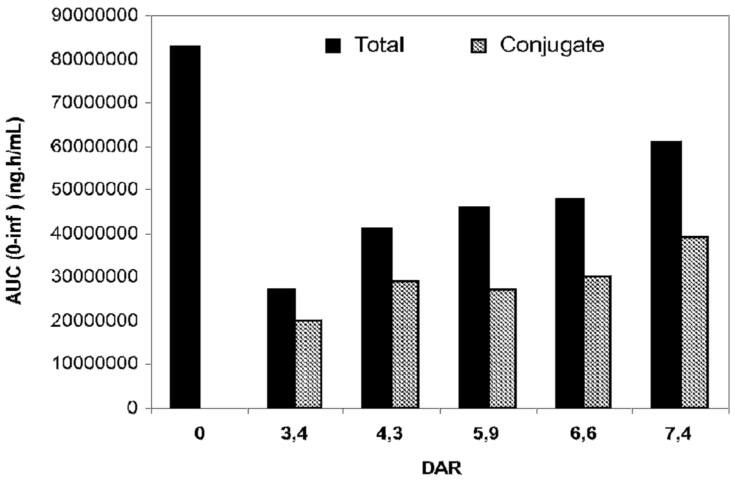
Figure 9B:
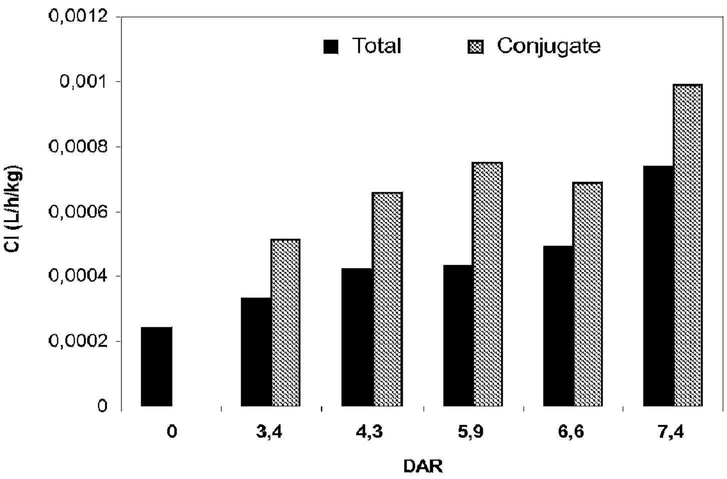

FIGS. 9A and 9B: PK parameters for hu2H11R35R74-PEG4-NHAc-DM4 at various DARs, Bar graph representation of the exposure to (AUC(0-inf); FIG. 9A) and clearance (Cl; FIG. 9B) of several ADCs as a function of the DAR after a single dose intravenous administration of 20 mg/kg of immunoconjugate in HGS to male CD-1 mice (n=4).

Figure 10:
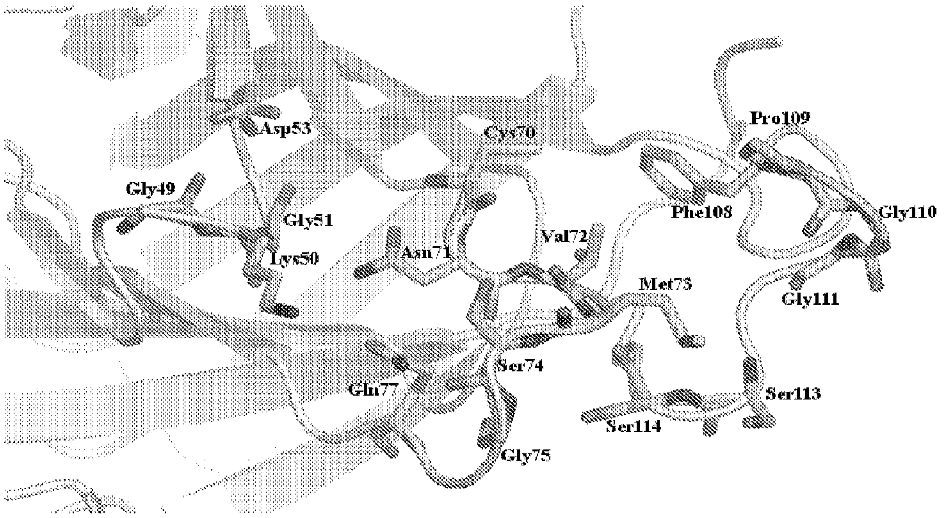

FIG. 10: illustrates the mapping of EphA2 epitope for Fab2H11.

FIG. 11: is the sequence of EphA2 wherein residues in dark grey are part of the epitope; residues in light grey are not visible in the crystal structures.

Figure 12A:
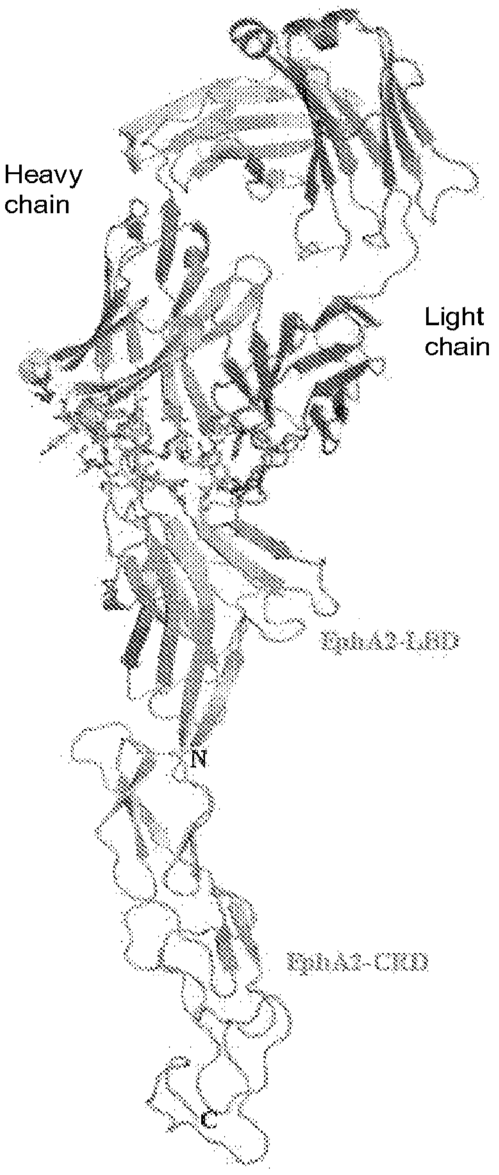
Figure 12B:
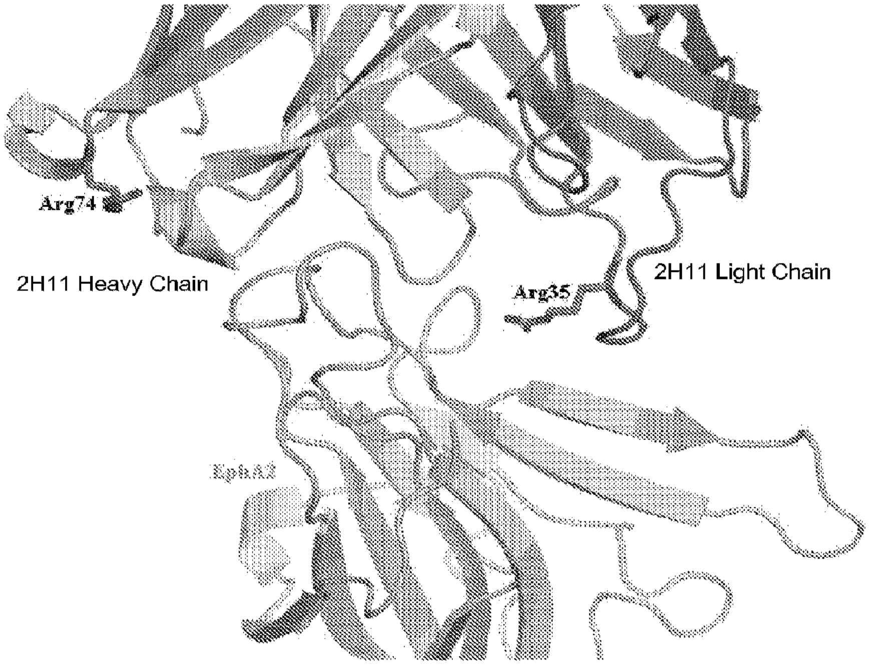

FIG. 12 A: represents the overall structure of the complex and FIG. 12B is a magnification of the part with the two Fab mutations.

Figure 13:
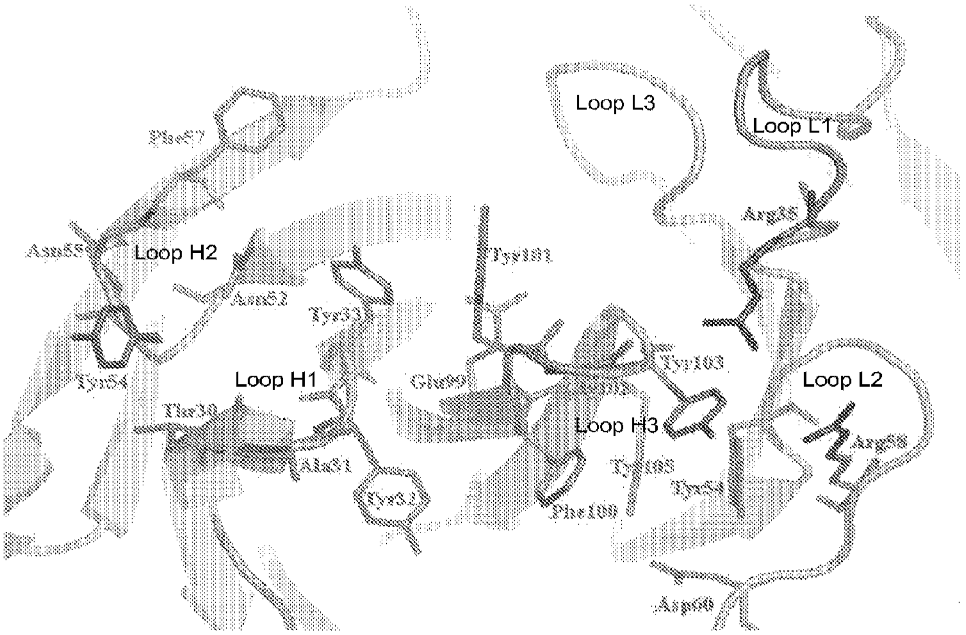

FIG. 13: is a represents the structure of the paratope.

Figure 14:
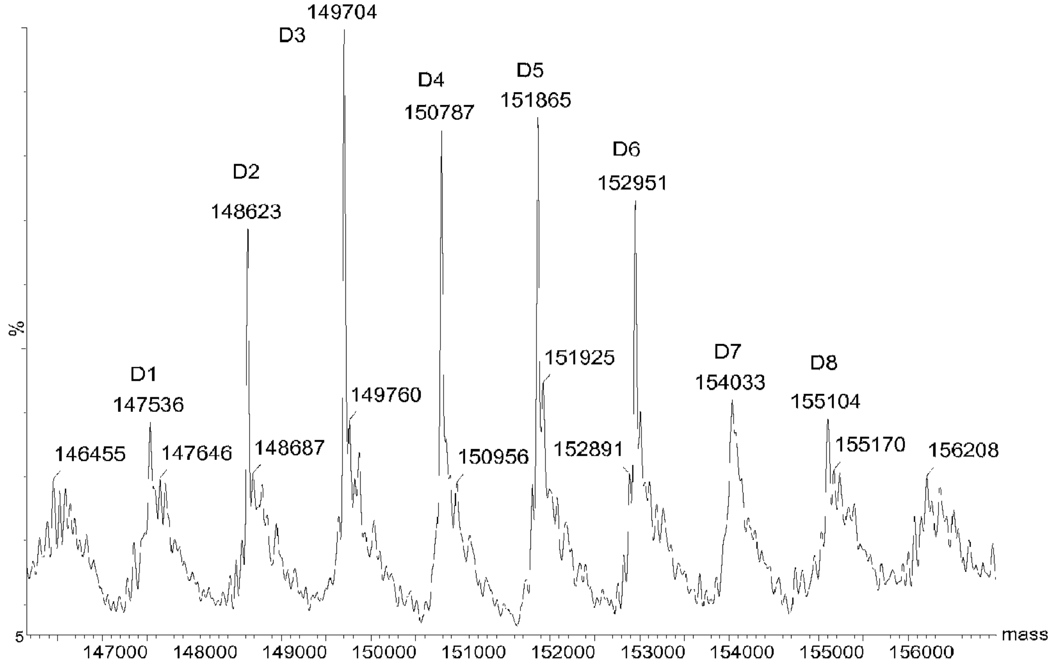

FIG. 14: HRMS spectrum of hu2H11R35R74-PEG4-NMeAc-DM4.

Figure 15:
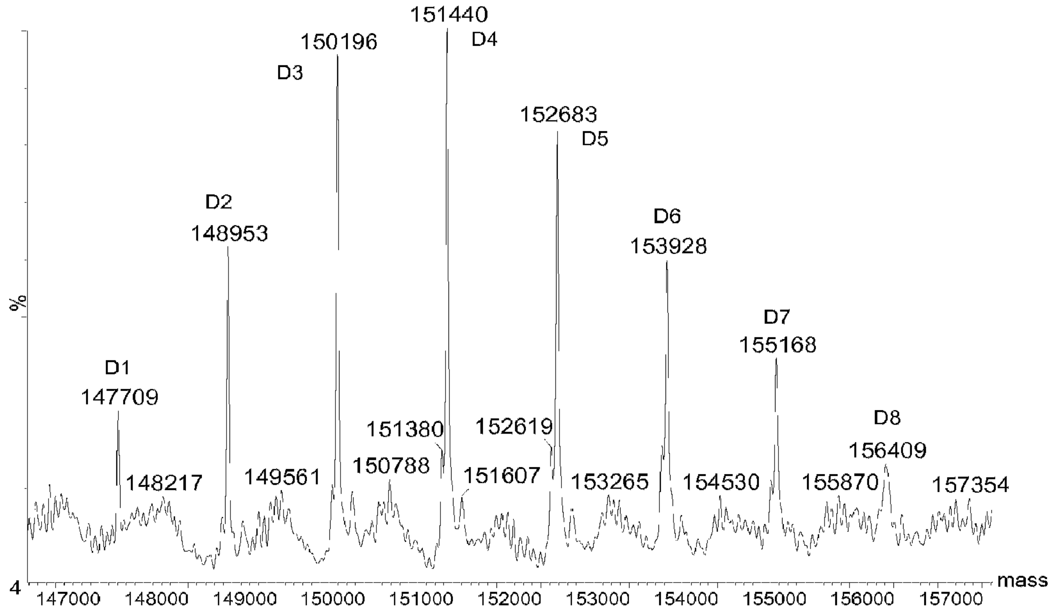

FIG. 15: HRMS spectrum of hu2H11R35R74-PEG8-NHAc-DM4.

Figure 16:
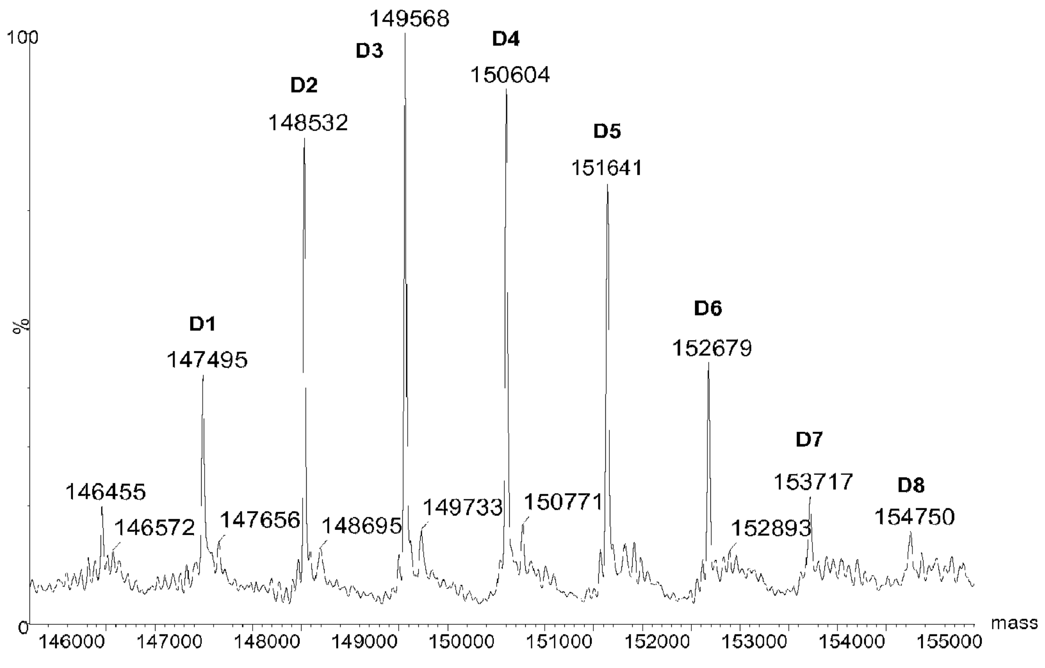

FIG. 16: HRMS spectrum of hu2H11R35R74-PEG4-Allyl-DM4.

Figure 17:
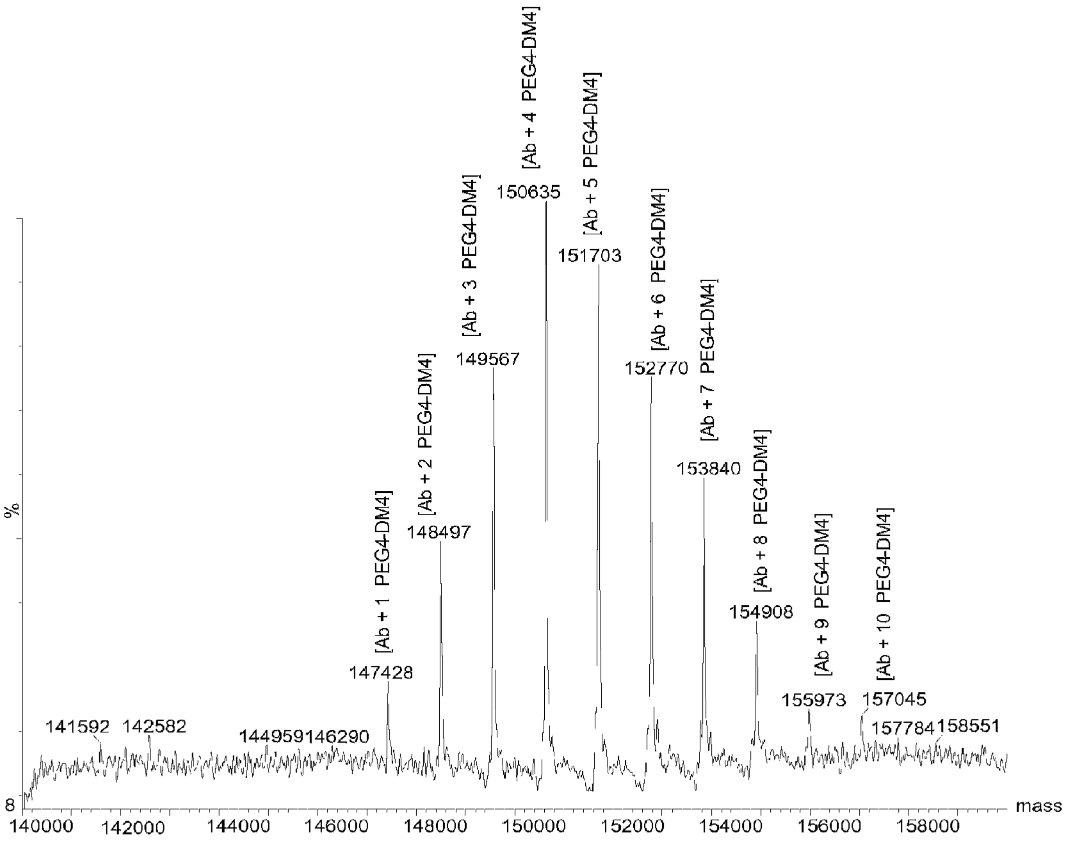

FIG. 17: HRMS spectrum of hu2H11-PEG4-NHAc-DM4.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The practice of the present invention employs, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook et al, 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et ah, eds., 1987, and periodic updates); PCR: The Polymerase Chain Reaction, (Mullis et al, ed., 1994); A Practical Guide to Molecular Cloning (Perbal Bernard V., 1988); Phage Display: A Laboratory Manual (Barbas et al., 2001). Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

New antibodies and fragments thereof, capable of specifically binding the EphA2 receptor and antagonizing said receptor are herein provided. In particular, the novel antibodies or fragments of the invention specifically bind Eph receptors on the cell surface, but are preferentially devoid of any agonist activity. On the other hand, they are capable of inhibiting the cellular functions of the receptor even in the presence of its ligands.

As used herein, the term "EphA2 receptor" refers to a tyrosine kinase belonging to the Eph receptors family (reviewed in Pasquale, E. B. et al., 2005, *Nature Reviews Mol. Cell. Biol.*, 6, 462-475), and comprising, for example, an amino sequence as in Genbank accession Nos NM_004431 (human EphA2), NM_010139 (murine EphA2), or NXM_345596 (rat EphA2). Human EphA2 is a preferred EphA2 receptor. The term "EphA2 ligand" as used herein refers to a protein that binds to, and optionally activates (e.g. stimulates the autophosphorylation of), an EphA2 receptor. A preferred EphA2 ligand herein is "ephrinA1", which binds to the EphA2 receptor and comprises, for example, an amino sequence as in Genbank accession NM_004428 (human ephrinA1).

The term "antagonist" as used herein refers to a molecule which is capable of inhibiting one or more of the biological activities of a target molecule, such as an EphA2 receptor. Antagonists may act by interfering with the binding of a receptor to a ligand and vice versa, by decreasing EphA2 phosphorylation that could be induced by a ligand, and/or by inhibiting the intracellular pathways that are induced by the binding of such ligand, and/or by inhibiting the homo/hetero-oligomerization of EphA receptors. The antagonist may completely block receptor-ligand interactions or may substantially reduce such interactions. All such points of intervention by an antagonist shall be considered equivalent for purposes of this invention. Thus, included within the scope of the invention are antagonists (e.g. neutralizing antibodies) that bind to EphA2 receptor, EphA2 ligand or a complex of an EphA2 receptor and EphA2 ligand; amino acid sequence variants or derivatives of an EphA2 receptor or EphA2 ligand which antagonize the interaction between an EphA2 receptor and EphA2 ligand; soluble EphA2 receptor or soluble EphA2 ligand, optionally fused to a heterologous molecule such as an immunoglobulin region (e.g. an immunoadhesin); a complex comprising an EphA2 receptor in association with EphA2 ligand; synthetic or native sequence peptides which bind to EphA2 receptor or EphA2 ligand. In a preferred embodiment, the antagonist is an antibody.

The term "agonist" as used herein refers to any compound, including a protein, a polypeptide, a peptide, an antibody, an antibody fragment, a conjugate, a large molecule, a small molecule, capable of activating one or more of the biological activities of the target molecule. EphA2 agonists act by stimulating phosphorylation of the protein, thereby triggering degradation of said protein.

Thus in a preferred embodiment the present invention provides, among other features, anti-EphA2 monoclonal antibodies, anti-EphA2 humanized antibodies, and fragments of the anti-EphA2 antibodies. Each of the antibodies and antibody fragments of the present invention is designed to specifically recognize and bind the EphA2 receptor, and acts as an EphA2 receptor antagonist, inhibiting the phosphorylation induced by EphA2 ligands.

The EphA2 receptor belongs to a family of receptor whose cytoplasmic tail phosphorylation is increased after ligand binding to interact with a variety of adapter and signaling proteins, leading to the activation of different downstream cellular signaling pathways (Kullander, K. and Klein, R., 2002, *Nature Reviews Mol. Cell. Biol.,* 3: 475-486; Noren, N. K. and Pasquale, E. B., 2004, *Cell signal.,* 16: 655-666). As used herein, the term "EphA2-mediated signaling" refers to all the cellular events which occur in response to ligand binding by EphA2. Whereas antibodies disclosed in the prior art agonize the EphA2 receptor, and, in particular, increase the tyrosine phosphorylation of the EphA2 protein, the antibodies and antibody fragments of the invention are preferentially devoid of any such agonistic properties. In particular, they are unable to stimulate EphA2 phoshorylation by themselves. Like the antibodies described in WO 2008/010101, the antagonistic antibodies and antibody fragments of the invention are devoid of any agonist activity. In a specific embodiment, they are unable to promote tyrosine phosphorylation of EphA2, unlike other antibodies described in the prior art (Dodge-Zantek et al., 1999, *Cell Growth & Differ.,* 10: 629-638; WO 01/12172, WO 03/094859, WO 2004/014292, WO 2004/101764, WO 2006/023403, WO 2006/047637, WO 2007/030642).

This invention provides actual antagonistic anti-EphA2 antibodies. The antibodies and antibody fragments of the invention have the ability of inhibiting the cellular functions of the EphA2 receptor, even in the presence of the ligands of said EphA2 receptor, e.g. ephrinA1. In one embodiment, the antibodies and antibody fragments of the invention can inhibit the binding of a ligand to an EphA2 receptor. In a preferred embodiment, the binding of ephrinA1 to EphA2 is prevented by the antibodies and fragments thereof provided by this invention. Remarkably, in another embodiment, the antibodies and antibody fragments of the invention are capable of inhibiting tyrosine phosphorylation of the EphA2 receptor, even in the presence of ephrinA1.

Antibodies

The term "antibody" is used herein in the broadest sense and specifically covers monoclonal antibodies (including full length monoclonal antibodies) of any isotype such as IgG, IgM, IgA, IgD, and IgE, polyclonal antibodies, multispecific antibodies, chimeric antibodies, and antibody fragments. An antibody reactive with a specific antigen can be generated by recombinant methods such as selection of libraries of recombinant antibodies in phage or similar vectors, or by immunizing an animal with the antigen or an antigen-encoding nucleic acid.

A typical antibody is comprised of two identical heavy chains and two identical light chains that are joined by disulfide bonds. Each heavy and light chain contains a constant region and a variable region. As used herein, "$V_H$" or "VH" refers to the variable region of an immunoglobulin heavy chain of an antibody, including the heavy chain of an Fv, scFv, dsFv, Fab, Fab', or F(ab')2 fragment. Reference to "$V_L$" or "VL" refers to the variable region of the immunoglobulin light chain of an antibody, including the light chain of an Fv, scFv, dsFv, Fab, Fab', or F(ab')2 fragment. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus. The more highly conserved portions of the variable regions are called the "framework regions" ("FR"). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest,* $5^{th}$ edition, National Institute of Health, Bethesda, Md., 1991).

The constant domains are not involved directly in the binding of an antibody to an antigen, but exhibit various effector functions, such as participation of the antibody in antibody-dependent cellular toxicity (ADCC), phagocytosis via binding to Fcγ receptor, half/life clearance rate via neonatal Fc receptor (FcRn) and complement dependent cytotoxicity (CDC) via the C1q component of the complement cascade.

The "light chains" of antibodies (immunoglobulins) from any vertebrate species can be assigned to one of two clearly distinct types, called kappa (K) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called α, δ, ϵ, γ, and μ, respectively. Within light and heavy chains, the variable and constant regions are joined by a "J" region of about 12 or more amino acids, with the heavy chain also including a "D" region of about 10 more amino acids (see e.g., *Fundamental Immunology* Ch. 7, Paul, W., ed., $2^{nd}$ edition, Raven Press, N.Y., 1989). The subunit structures and three-dimensional configurations of different classes of immunoglobulins are well known and described generally in, for example, Abbas et al. (*Cellular and Mol. Immunology,* $4^{th}$ edition, W. B. Saunders, Co., 2000). An antibody may be part of a larger fusion molecule, formed by covalent or non-covalent association of the antibody with one or more other proteins or peptides.

A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

A "monoclonal antibody", as used herein, is an antibody obtained from a population of substantially homogeneous antibodies, i.e. the antibodies forming this population are essentially identical except for possible naturally occurring mutations which might be present in minor amounts. These antibodies are directed against a single epitope and are therefore highly specific.

A "naked antibody" for the purposes herein is an antibody which is not conjugated to a cytotoxic moiety or radiolabel.

An "epitope" is the site on the antigen to which an antibody binds. It can be formed by contiguous residues or by non-contiguous residues brought into close proximity by the folding of an antigenic protein. Epitopes formed by contiguous amino acids are typically retained on exposure to denaturing solvents, whereas epitopes formed by non-contiguous amino acids are typically lost under said exposure.

As used herein, the term "$K_D$" refers to the dissociation constant of a particular antibody/antigen interaction. "Binding affinity" generally refers to the strength of the sum total of non-covalent interactions between a single binding site of a molecule {e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the $K_D$. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

The present invention proceeds from a murine anti-EphA2 antibody, herein mu2H11R35R74, which is fully characterized with respect to the amino acid sequences of both light and heavy chains, the identification of the CDRs, the identification of surface amino acids, and means for its expression in recombinant form.

The murine antibody of the invention can be obtained for example by site-directed mutagenesis of the antibody 53.2H11. The 53.2H11 antibody is produced by a hybridoma deposited under the Budapest Treaty on June 16, at the American Type Culture Collection, under the accession number PTA-7662, and is described in PCT application WO 2008/010101. Thus, the amino acid sequences of the both light and heavy chains of 53.2H11, the identification of the CDRs, the identification of surface amino acids, as well as polynucleotide sequences encoding said light and heavy chains are all disclosed in WO 2008/010101.

The primary amino acid and DNA sequences of antibody mu2H11R35R74 light and heavy chains, and of humanized versions thereof, are disclosed herein. In one embodiment, this invention provides antibodies or epitope-binding fragment thereof comprising one or more CDRs having an amino acid sequence selected from the group consisting of SEQ ID NOS: 1, 2, 3, 4, 5, 6.

In a preferred embodiment, the antibodies of the invention comprise at least one heavy chain and at least one light chain, and said heavy chain comprises three sequential CDRs having amino acid sequences selected from the group consisting of SEQ ID NOS: 1, 2, 3, and said light chain comprises three sequential CDRs having amino acid sequences selected from the group consisting of SEQ ID NOS: 4, 5, 6.

In a preferred embodiment the paratope of said monoclonal antibodies or epitope-binding fragments thereof comprises in the light chain: Arg35 of Loop L1, Tyr54, Arg58 and Asp60 of L2.

In a preferred embodiment the paratope of said monoclonal antibodies or epitope-binding fragments thereof comprises heavy chain: Thr30, Ala31, Tyr32 and Tyr33 of Loop H1, Asn52, Tyr54, Asn55 and Phe57 of H2 and Glu99, Phe100, Tyr101, Gly102, Tyr103 and Tyr105 of H3.

Said antibodies or an epitope-binding fragments thereof can comprise mutations:

at the position: Thr H28 at one of few of the following positions on the light chain: 35, 26 to 31, 34 to 37, 55, 56, 57, 59 and 94 to 102, and/or at one of few of the following positions on the heavy chain: 28, 54 and 57.

In another embodiment the antibodies of the invention specifically bind to an epitope of human EphA2 receptor comprising residues Gly49, Lys50, Gly51, Asp53, Cys70, Asn71, Val72, Met73, Ser74, Gly75, Gln77, Phe108, Pro109, Gly110, Gly111, Ser113 and Ser114 of the LBD from the extra-cellular domain of EphA2 receptor, or a conservatively substituted form thereof.

In another embodiment, the antibodies of the invention comprise a $V_H$ having an amino acid sequence consisting of SEQ ID NO 8. In another preferred embodiment, the antibodies of the invention comprise a $V_L$ having an amino acid sequence consisting of SEQ ID NO 10.

Humanized or Resurfaced 2H11R35R74 Antibody

As used herein, the term "humanized antibody" refers to a chimeric antibody which contains minimal sequence derived from non-human immunoglobulin. A "chimeric antibody", as used herein, is an antibody in which the constant region, or a portion thereof, is altered, replaced, or exchanged, so that the variable region is linked to a constant region of a different species, or belonging to another antibody class or subclass. "Chimeric antibody" also refers to an antibody in which the variable region, or a portion thereof, is altered, replaced, or exchanged, so that the constant region is linked to a variable region of a different species, or belonging to another antibody class or subclass.

The goal of humanization is a reduction in the immunogenicity of a xenogenic antibody, such as a murine antibody, for introduction into a human, while maintaining the full antigen binding affinity and specificity of the antibody. Humanized antibodies, or antibodies adapted for non-rejection by other mammals, may be produced using several technologies such as resurfacing and CDR grafting. As used herein, the resurfacing technology uses a combination of molecular modeling, statistical analysis and mutagenesis to alter the non-CDR surfaces of antibody variable regions to resemble the surfaces of known antibodies of the target host.

Strategies and methods for the resurfacing of antibodies, and other methods for reducing immunogenicity of antibodies within a different host, are disclosed in U.S. Pat. No. 5,639,641, which is hereby incorporated in its entirety by reference. Briefly, in a preferred method, (1) position alignments of a pool of antibody heavy and light chain variable regions is generated to give a set of heavy and light chain variable region framework surface exposed positions wherein the position alignments for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Å of any atom of any residue of the complementarity-determining regions of the rodent antibody; and (5) the humanized rodent antibody having binding specificity is produced.

Another preferred method of humanization of antibodies, based on the identification of flexible residues, has been described in PCT application WO 2009/032661. Said method comprises the following steps: (1) building a homology model of the parent mAb and running a molecular dynamics simulation; (2) analyzing the flexible residues and identification of the most flexible residues of a non-human antibody molecule, as well as identifying residues or motifs likely to be a source of heterogeneity or of degradation reaction; (3) identifying a human antibody which displays the most similar ensemble of recognition areas as the parent antibody; (4) determining the flexible residues to be mutated, residues or motifs likely to be a source of heterogeneity and degradation are also mutated; and (5) checking for the presence of known T cell or B cell epitopes. The flexible residues can be found using a molecular dynamics calculation using an implicit solvent model, which accounts for the interaction of the water solvent with the protein atoms over the period of time of the simulation.

Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991, *Molecular Immunology* 28 (4/5): 489-498; Studnicka G. M. et al., 1994, *Protein Engineering* 7(6): 805-814; Roguska M. A. et al., 1994, *Proc. Natl. Acad. Sci. U.S.A.,* 91:969-973), and chain shuffling (U.S. Pat. No. 5,565,332).

In certain embodiments both the variable and constant regions of the antibodies, or antigen-binding fragments, variants, or derivatives thereof are fully human. Fully human antibodies can be made using techniques that are known in the art. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human antibodies can likewise be produced by various display technologies, e.g., phage display or other viral display systems. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741 (said references incorporated by reference in their entireties).

The present invention provides humanized antibodies or fragments thereof, which recognize EphA2 receptor and act as antagonists. In a preferred embodiment, the humanized antibodies or epitope-binding fragments thereof have the additional ability to inhibit growth of a cancer cell expressing the EphA2 receptor. In a further embodiment, the humanized antibody or epitope-binding fragment thereof have the additional ability to inhibit the migration of a metastatic cancer cell expressing the EphA2 receptor.

A preferred embodiment of such a humanized antibody is a humanized 2H11R35R74 antibody, or an epitope-binding fragment thereof.

In another preferred embodiment, the humanized antibodies of the invention are obtained by site-directed mutagenesis of the polynucleotide sequences encoding hu53.2H11 (WO 2008/010101) referred herein as hu2H11.

In more preferred embodiments, there are provided resurfaced or humanized versions of the 2H11R35R74 antibody wherein surface-exposed residues of the antibody or its fragments are replaced in both light and heavy chains to more closely resemble known human antibody surfaces. The humanized 2H11R35R74 antibody or epitope-binding fragments thereof of the present invention have improved properties. For example, humanized 2H11R35R74 antibodies or epitope-binding fragments thereof specifically recognize EphA2 receptor. More preferably, the humanized 2H11R35R74 antibody or epitope-binding fragments thereof have the additional ability to inhibit the growth of an EphA2 receptor-expressing cell.

The humanized versions of the 2H11R35R74 antibody are also fully characterized herein with respect to their respective amino acid sequences of both light and heavy chain variable regions, the DNA sequences of the genes for the light and heavy chain variable regions, the identification of the CDRs, the identification of their surface amino acids, and disclosure of a means for their expression in recombinant form. However, the scope of the present invention is not limited to antibodies and fragments comprising these sequences. Instead, all antibodies and fragments that specifically bind to EphA2 receptor are included in the present invention. Preferably, the antibodies and fragments that specifically bind to EphA2 receptor antagonize the biological activity of the receptor. More preferably, such antibodies further are substantially devoid of agonist activity. Thus, antibodies and epitope-binding antibody fragments of the present invention may differ from the 2H11R35R74 antibody or the humanized derivatives thereof, in the amino acid sequences of their scaffold, CDRs, and/or light chain and heavy chain, and still fall within the scope of the present invention.

The CDRs of the 2H11R35R74 antibody have been determined by solving the crystal structure of the Fab fragment of 2H11R35R74 in complex with the extra-cellular domain of the EphA2 receptor. The residues from the 2H11R35R74 which interact with the extra-cellular domain of EphA2 have been identified. Accordingly, antibodies and fragments are provided that have improved properties produced by, for example, affinity maturation of an antibody of the present invention.

The mouse light chain $IgV_K$ and $J_K$ germline genes and heavy chain IgVh and Jh germline genes from which 53.2H11 was likely derived have been identified, and were disclosed in WO 2008/010101. The accession numbers of said germline sequences are respectively MMU231196 and AF303833. Such germline gene sequences are useful to identify somatic mutations in the antibodies, including in the CDRs.

The sequences of the heavy chain and light chain variable regions of the 2H11R35R74 antibody, and the sequences of their CDRs were not previously known and are set forth in this application. Such information can be used to produce humanized versions of the 2H11R35R74 antibody. It is also possible to obtain the humanized 2H11R35R74 antibodies of the invention by site-directed mutagenesis of hu2H11. These humanized anti-EphA2 antibodies or their derivatives may also be used as the cell binding agent of the conjugates of the present invention.

Thus, in one embodiment, this invention provides humanized antibodies or epitope-binding fragment thereof comprising one or more CDRs having an amino acid sequence selected from the group consisting of SEQ ID NOS: 1, 2, 3, 4, 5, 6. In a preferred embodiment, the humanized antibodies of the invention comprise at least one heavy chain and at least one light chain, wherein said heavy chain comprises three sequential CDRs having amino acid sequences represented by SEQ ID NOS: 1, 2, and 3, and wherein said light chain comprises three sequential CDRs having amino acid sequences represented by SEQ ID NOS: 4, 5, and 6.

In one embodiment, this invention provides a humanized 2H11R35R74 antibody or fragments thereof which comprises a $V_H$ having an amino acid sequence consisting of SEQ ID NO. 12. In another embodiment, this invention provides a humanized 2H11R35R74 antibody or fragments thereof which comprises a $V_L$ having an amino acid sequence consisting of SEQ ID NO 14.

In a preferred embodiment, a humanized 2H11R35R74 antibody is provided, which comprises at least one heavy chain and at least one light chain, wherein said heavy chain comprises three sequential CDRs having amino acid sequences represented by SEQ ID NOS: 1, 2, and 3, wherein said light chain comprises three sequential CDRs having amino acid sequences represented by SEQ ID NOS: 4, 5, and 6, wherein said heavy chain has an amino acid sequence consisting of SEQ ID NO. 12, and wherein said light chain has an amino acid sequence consisting of SEQ ID NO. 14.

Polynucleotides, Vectors, and Host Cells.

Nucleic acids encoding anti-EphA2 antibodies of the invention are provided. In one embodiment, the nucleic acid molecule encodes a heavy and/or a light chain of an anti-EphA2 immunoglobulin. In a preferred embodiment, a single nucleic acid encodes a heavy chain of an anti-EphA2 immunoglobulin and another nucleic acid molecule encodes the light chain of an anti-EphA2 immunoglobulin.

In another aspect of this invention, there are provided polynucleotides encoding polypeptides having an amino acid sequence selected from the group of SEQ ID NOS: 1, 2, 3, 4, 5, 6, 8, 10, 12, 14, 16 and 18. In a preferred embodiment, the polynucleotide of the invention is selected from the group consisting of SEQ ID NOs: 7, 9, 11, 13, 15 and 17. The invention is not limited to said polynucleotides per se but also includes all polynucleotides displaying at least 80% identity with said polynucleotides.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the"isolated polynucleotide" is found in nature, (2) is operably linked to a polynucleotide which it is not linked to in nature, or (3) does not occur in nature as part of a larger sequence.

The invention provides vectors comprising the polynucleotides of the invention. In one embodiment, the vector contains a polynucleotide encoding a heavy chain of an anti-EphA2 immunoglobulin. In another embodiment, said polynucleotide encodes the light chain of an anti-EphA2 immunoglobulin. The invention also provides vectors comprising polynucleotide molecules encoding fusion proteins, modified antibodies, antibody fragments, and probes thereof.

In order to express the heavy and/or light chain of the anti-EphA2 antibodies of the invention, the polynucleotides encoding said heavy and/or light chains are inserted into expression vectors such that the genes are operatively linked to transcriptional and translational sequences.

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

Certain vectors are capable of directing the expression of genes to which they are operatively linked. Such vectors are referred to herein as "recombinant expression vectors" (or simply, "expression vectors"). In general, expression vectors of utility in recombinant DNA techniques are in the form of plasmids. In the present specification, "plasmid" and "vector" may be used interchangeably as the plasmid is the most commonly used form of vector. However, the invention is intended to include such forms of expression vectors, such as bacterial plasmids, YACs, cosmids, retrovirus, EBV-derived episomes, and all the other vectors that the skilled man will know to be convenient for ensuring the expression of the heavy and/or light chains of the antibodies of the invention. The skilled man will realize that the polynucleotides encoding the heavy and the light chains can be cloned into different vectors or in the same vector. In a preferred embodiment, said polynucleotides are cloned in the same vector.

Polynucleotides of the invention and vectors comprising these molecules can be used for the transformation of a suitable mammalian host cell, or any other type of host cell known to the skilled person. The term "recombinant host cell"

(or simply "host cell"), as used herein, is intended to refer to a cell into which a recombinant expression vector has been introduced. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein.

Transformation can be by any known method for introducing polynucleotides into a host cell. Such methods are well known of the man skilled in the art and include dextran-mediated transformation, calcium phosphate precipitation, polybrene-mediated transfection, protoplast fusion, electroporation, encapsulation of the polynucleotide into liposomes, biolistic injection and direct microinjection of DNA into nuclei.

Antibody Fragments

The antibodies of the present invention include both the full length antibodies discussed above, as well as epitope-binding fragments. As used herein, "antibody fragments" include any portion of an antibody that retains the ability to bind to the epitope recognized by the full length antibody, generally termed "epitope-binding fragments." Examples of antibody fragments include, but are not limited to, Fab, Fab' and $F(ab')_2$, Fd, single-chain Fvs (scFv), single-chain antibodies, disulfide-linked Fvs (dsFv) and fragments comprising either a $V_L$ or $V_H$ region. Epitope-binding fragments, including single-chain antibodies, may comprise the variable region(s) alone or in combination with the entirety or a portion of the following: hinge region, $C_H1$, $C_H2$, and $C_H3$ domains.

Such fragments may contain one or both Fab fragments or the $F(ab')_2$ fragment. Preferably, the antibody fragments contain all six CDRs of the whole antibody, although fragments containing fewer than all of such regions, such as three, four or five CDRs, are also functional. Further, the fragments may be or may combine members of any one of the following immunoglobulin classes: IgG, IgM, IgA, IgD, or IgE, and the subclasses thereof.

Fab and $F(ab')_2$ fragments may be produced by proteolytic cleavage, using enzymes such as papain (Fab fragments) or pepsin ($F(ab')_2$ fragments).

The "single-chain FVs" ("scFvs") fragments are epitope-binding fragments that contain at least one fragment of an antibody heavy chain variable region ($V_H$) linked to at least one fragment of an antibody light chain variable region ($V_L$). The linker may be a short, flexible peptide selected to ensure that the proper three-dimensional folding of the ($V_L$) and ($V_H$) regions occurs once they are linked so as to maintain the target molecule binding-specificity of the whole antibody from which the single-chain antibody fragment is derived. The carboxyl terminus of the ($V_L$) or ($V_H$) sequence may be covalently linked by a linker to the amino acid terminus of a complementary ($V_L$) or ($V_H$) sequence.

Single-chain antibody fragments of the present invention contain amino acid sequences having at least one of the variable or complementarity determining regions (CDRs) of the whole antibodies described in this specification, but are lacking some or all of the constant domains of those antibodies. These constant domains are not necessary for antigen binding, but constitute a major portion of the structure of whole antibodies. Single-chain antibody fragments may therefore overcome some of the problems associated with the use of antibodies containing a part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies.

Single-chain antibody fragments may be generated by molecular cloning, antibody phage display library or similar techniques well known to the skilled artisan. These proteins may be produced, for example, in eukaryotic cells or prokaryotic cells, including bacteria. The epitope-binding fragments of the present invention can also be generated using various phage display methods known in the art. In phage display methods, functional antibody domains are displayed on the surface of phage particles which carry the polynucleotide sequences encoding them. In particular, such phage can be utilized to display epitope-binding domains expressed from a repertoire or combinatorial antibody library (e.g., human or murine). Phage expressing an epitope-binding domain that binds the antigen of interest can be selected or identified with antigen, e.g., using labelled antigen bound or captured to a solid surface or bead. Phage used in these methods are typically filamentous phage including fd and M13 binding domains expressed from phage with Fab, Fv or disulfide-stabilized Fv antibody domains recombinantly fused to either the phage gene III or gene VIII protein.

Examples of phage display methods that can be used to make the epitope-binding fragments of the present invention include those disclosed in Brinkman et al., 1995, *J. Immunol. Methods,* 182: 41-50; Ames et al., 1995, *J. Immunol. Methods,* 184: 177-186; Kettleborough et al., 1994, *Eur. J. Immunol.,* 24:952-958; Persic et al., 1997, *Gene* 187: 9-18; Burton et al., 1994, *Advances in Immunology,* 57: 191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

After phage selection, the regions of the phage encoding the fragments can be isolated and used to generate the epitope-binding fragments through expression in a chosen host, including mammalian cells, insect cells, plant cells, yeast, and bacteria, using recombinant DNA technology, e.g., as described in detail below. For example, techniques to recombinantly produce Fab, Fab' and $F(ab')_2$ fragments can also be employed using methods known in the art such as those disclosed in PCT publication WO 92/22324; Mullinax et al., 1992, *BioTechniques,* 12(6): 864-869; Sawai et al., 1995, *AJRI,* 34: 26-34; and Better et al., 1988, *Science,* 240: 1041-1043; said references incorporated by reference in their entireties. Examples of techniques which can be used to produce single-chain Fvs and antibodies include those described in U.S. Pat. Nos. 4,946,778 and 5,258,498; Huston et al., 1991, *Methods in Enzymology* 203: 46-88; Shu et al., 1993, *Proc. Natl. Acad. Sci. U.S.A.,* 90: 7995-7999; Skerra et al., 1988, *Science,* 240: 1038-1040.

Functional Equivalents

Also included within the scope of the invention are functional equivalents of the anti-EphA antibody and the humanized anti-EphA2 receptor antibody. The term "functional equivalents" includes antibodies with homologous sequences, chimeric antibodies, artificial antibodies and modified antibodies, for example, wherein each functional equivalent is defined by its ability to bind to EphA2 receptor. The skilled artisan will understand that there is an overlap in the group of molecules termed "antibody fragments" and the group termed "functional equivalents." Methods of producing functional equivalents are known to the person skilled in the art and are disclosed, for example, in PCT Application WO 93/21319, European Patent No. EP 0239400; PCT Application WO 89/09622; European Patent No. EP 0338745; and European Patent Application EP 0332424, which are incorporated in their respective entireties by reference.

Antibodies with homologous sequences are those antibodies with amino acid sequences that have sequence homology with amino acid sequence of an anti-EphA antibody and a humanized anti-EphA antibody of the present invention. Preferably homology is with the amino acid sequence of the variable regions of the anti-EphA antibody and humanized anti-EphA antibody of the present invention. "Sequence homology" as applied to an amino acid sequence herein is defined as a sequence with at least about 90%, 91%, 92%, 93%, or 94% sequence homology, and more preferably at least about 95%, 96%, 97%, 98%, or 99% sequence homology to another amino acid sequence, as determined, for example, by the FASTA search method in accordance with Pearson and Lipman, 1988, *Proc. Natl. Acad. Sci. U.S.A.,* 85: 2444-2448.

A chimeric antibody is one in which different portions of an antibody are derived from different animal species. For example, an antibody having a variable region derived from a murine monoclonal antibody paired with a human immunoglobulin constant region. Methods for producing chimeric antibodies are known in the art. See, e.g., Morrison, 1985, *Science,* 229: 1202; Oi et al., 1986, *BioTechniques,* 4: 214; Gillies et al., 1989, *J. Immunol. Methods,* 125: 191-202; U.S. Pat. Nos. 5,807,715; 4,816,567; and 4,816,397, which are incorporated herein by reference in their entireties.

Humanized forms of chimeric antibodies are made by substituting the complementarity determining regions of, for example, a mouse antibody, into a human framework domain, e.g., see PCT Pub. No. WO 92/22653. Humanized chimeric antibodies preferably have constant regions and variable regions other than the complementarity determining regions (CDRs) derived substantially or exclusively from the corresponding human antibody regions and CDRs derived substantially or exclusively from a mammal other than a human.

Artificial antibodies include scFv fragments, diabodies, triabodies, tetrabodies and mru (see reviews by Winter, G. and Milstein, C., 1991, Nature, 349: 293-299; Hudson, P. J., 1999, *Current Opinion in Immunology,* 11: 548-557), each of which has antigen-binding ability. In the single chain Fv fragment (scFv), the $V_H$ and $V_L$ domains of an antibody are linked by a flexible peptide. Typically, this linker peptide is about 15 amino acid residues long. If the linker is much smaller, for example 5 amino acids, diabodies are formed, which are bivalent scFv dimers. If the linker is reduced to less than three amino acid residues, trimeric and tetrameric structures are formed that are called triabodies and tetrabodies. The smallest binding unit of an antibody is a CDR, typically the CDR2 of the heavy chain which has sufficient specific recognition and binding that it can be used separately. Such a fragment is called a molecular recognition unit or mru. Several such mrus can be linked together with short linker peptides, therefore forming an artificial binding protein with higher avidity than a single mru.

The functional equivalents of the present application also include modified antibodies, e.g., antibodies modified by the covalent attachment of any type of molecule to the antibody. For example, modified antibodies include antibodies that have been modified, e.g., by glycosylation, acetylation, pegylation, phosphorylation, amidation, derivatization by known protecting/blocking groups, proteolytic cleavage, linkage to a cellular ligand or other protein, etc. The covalent attachment does not prevent the antibody from generating an anti-idiotypic response. These modifications may be carried out by known techniques, including, but not limited to, specific chemical cleavage, acetylation, formylation, metabolic synthesis of tunicamycin, etc. Additionally, the modified antibodies may contain one or more non-classical amino acids.

Functional equivalents may be produced by interchanging different CDRs on different chains within different frameworks. Thus, for example, different classes of antibody are possible for a given set of CDRs by substitution of different heavy chains, whereby, for example, IgG1-4, IgM, IgA1-2, IgD, IgE antibody types and isotypes may be produced. Similarly, artificial antibodies within the scope of the invention may be produced by embedding a given set of CDRs within an entirely synthetic framework.

Functional equivalents may be readily produced by mutation, deletion and/or insertion within the variable and/or constant region sequences that flank a particular set of CDRs, using a wide variety of methods known in the art.

The antibody fragments and functional equivalents of the present invention encompass those molecules with a detectable degree of binding to EphA2, when compared to the 2H11R35R74 antibody. A detectable degree of binding includes all values in the range of at least 10-100%, preferably at least 50%, 60% or 70%, more preferably at least 75%, 80%, 85%, 90%, 95% or 99% the binding ability of the murine 2H11R35R74 antibody to EphA2.

Improved Antibodies

The CDRs are of primary importance for epitope recognition and antibody binding. However, changes may be made to the residues that comprise the CDRs without interfering with the ability of the antibody to recognize and bind its cognate epitope. For example, changes that do not affect epitope recognition, yet increase the binding affinity of the antibody for the epitope may be made.

Thus, also included in the scope of the present invention are improved versions of both the murine and humanized antibodies, which also specifically recognize and bind EphA2, preferably with increased affinity.

Several studies have surveyed the effects of introducing one or more amino acid changes at various positions in the sequence of an antibody, based on the knowledge of the primary antibody sequence, on its properties such as binding and level of expression (Yang, W. P. et al., 1995, *J. Mol. Biol.,* 254: 392-403; Rader, C. et al., 1998, *Proc. Natl. Acad. Sci. U.S.A.,* 95: 8910-8915; Vaughan, T. J. et al., 1998, *Nature Biotechnology,* 16: 535-539).

In these studies, equivalents of the primary antibody have been generated by changing the sequences of the heavy and light chain genes in the CDR1, CDR2, CDR3, or framework regions, using methods such as oligonucleotide-mediated site-directed mutagenesis, cassette mutagenesis, error-prone PCR, DNA shuffling, or mutator-strains of *E. coli* (Vaughan, T. J. et al., 1998, *Nature Biotechnology,* 16: 535-539; Adey, N. B. et al., 1996, Chapter 16, pp. 277-291, in "*Phage Display of Peptides and Proteins*", Eds. Kay, B. K. et al., Academic Press). These methods of changing the sequence of the primary antibody have resulted in improved affinities of the secondary antibodies (Gram, H. et al., 1992, *Proc. Natl. Acad.*

*Sci. U.S.A.,* 89: 3576-3580; Boder, E. T. et al., 2000, *Proc. Natl. Acad. Sci. U.S.A.,* 97: 10701-10705; Davies, J. and Riechmann, L., 1996, *Immunotechnology,* 2: 169-179; Thompson, J. et al., 1996, *J. Mol. Biol.,* 256: 77-88; Short, M. K. et al., 2002, *J. Biol. Chem.,* 277: 16365-16370; Furukawa, K. et al., 2001, *J. Biol. Chem.,* 276: 27622-27628).

By a similar directed strategy of changing one or more amino acid residues of the antibody, the antibody sequences described in this invention can be used to develop anti-EphA2 antibodies with improved functions, including improved affinity for EphA2.

Preferred amino acid substitutions are those which: (1) reduce susceptibility to proteolysis, (2) reduce susceptibility to oxidation, (3) alter binding affinity for forming protein complexes, and (4) confer or modify other physico-chemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain (s) forming intermolecular contacts). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., 1991, *Nature,* 354: 105, which are each incorporated herein by reference.

Improved antibodies also include those antibodies having improved characteristics that are prepared by the standard techniques of animal immunization, hybridoma formation and selection for antibodies with specific characteristics.

The interaction between the constant region of an antibody and various Fc receptors (FcγR) is believed to mediate the effector functions of the antibody which include antibody-dependent cellular cytotoxicity (ADCC), fixation of complement, phagocytosis and half-life/clearance of the antibody. Various modifications to the constant region of antibodies of the invention may be carried out depending on the desired property. For example, specific mutations in the constant region to render an otherwise lytic antibody, non-lytic is detailed in EP 0629 240B1 and EP 0307 434B2 or one may incorporate a salvage receptor binding epitope into the antibody to increase serum half life (see U.S. Pat. No. 5,739,277). There are five currently recognised human Fcγ receptors, FcγR (I), FcγRIIa, FcγRIIb, FcγRIIIa and neonatal FcRn. Shields et al. (*J. Biol. Chem.,* 27: 6591-6604, 2001) demonstrated that a common set of IgGI residues is involved in binding all FcγRs, while FcγRII and FcγRIII utilize distinct sites outside of this common set. One group of IgGI residues reduced binding to all FcγRs when altered to alanine: Pro-238, Asp-265, Asp-270, Asn-297 and Pro-239. All are in the IgG CH2 domain and clustered near the hinge joining CH1 and CH2. While FcγRI utilizes only the common set of IgGI residues for binding, FcγRII and FcγRIII interact with distinct residues in addition to the common set.

Alteration of some residues reduced binding only to FcγRII (e.g. Arg-292) or FcγRIII (e.g. Glu-293). Some variants showed improved binding to FcγRII or FcγRIII but did not affect binding to the other receptor (e.g. Ser-267Ala improved binding to FcgRII but binding to FcγRIII was unaffected). Other variants exhibited improved binding to FcγRII or FcγRIII with reduction in binding to the other receptor (e.g. Ser-298Ala improved binding to FcγRIII and reduced binding to FcγRII). For FcγRIIIa, the best binding IgGI variants had combined alanine substitutions at Ser-298, Glu-333 and Lys-334. The neonatal FcRn receptor is believed to be involved in both antibody clearance and the transcytosis across tissues (see Junghans R. P, 1997, *Immunol. Res.,* 16: 29-57 and Ghetie et al., 2000, *Annu. Rev. Immunol.* 18: 739-766). Human IgGI residues determined to interact directly with human FcRn includes Ne253, Ser254, Lys288, Thr307, Gln311, Asn434 and His435. Switches at any of these positions described in this section may enable increased serum half-life and/or altered effector properties of antibodies of the invention.

Other modifications include glycosylation variants of the antibodies of the invention. Glycosylation of antibodies at conserved positions in their constant regions is known to have a profound effect on antibody function, particularly effector functioning such as those described above, see for example, Boyd et al (*Mol. Immunol.* 32: 1311-1318, 1996). Glycosylation variants of the antibodies or antigen binding fragments thereof of the present invention wherein one or more carbohydrate moiety is added, substituted, deleted or modified are contemplated. Introduction of an asparagine-X-serine or asparagine-X-threonine motif creates a potential site for enzymatic attachment of carbohydrate moieties and may therefore be used to manipulate the glycosylate of an antibody. In Raju et al. (*Biochemistry* 40: 8868-8876, 2001) the terminal sialylation of a TNFR-IgG immunoadhesin was increased through a process of regalactosylation and/or resialylation using β-1,4-galactosyltransferace and/or alpha, 2,3 sialyltransferase. Increasing the terminal sialylation is believed to increase the half-life of the immunoglobulin. Antibodies, in common with most glycoproteins, are typically produced as a mixture of glycoforms. This mixture is particularly apparent when antibodies are produced in eukaryotic, particularly mammalian cells. A variety of methods have been developed to manufacture defined glycoforms (see Zhang et al. 2004, *Science* 303: 371; Sears et al, 2001, *Science* 291: 2344; Wacker et al., 2002, *Science* 298: 1790; Davis et al. 2002, *Chem. Rev.* 102: 579; Hang et al., 2001, *Acc. Chem. Res.* 34: 727). Thus the invention contemplates a plurality of (monoclonal) antibodies (which may be of the IgG isotype, e.g. IgGI) as herein described comprising a defined number (e.g. 7 or less, for example 5 or less such as two or a single) glycoform(s) of said antibodies or antigen binding fragments thereof.

Therefore, improved antibodies according to the invention include in particular antibodies with enhanced functional properties. Of special interest are those antibodies with enhanced ability to mediate cellular cytotoxic effector functions such as ADCC. Such antibodies may be obtained by making single or multiple substitutions in the constant framework of the antibody, thus altering its interaction with the Fc receptors. Methods for designing such mutants can be found for example in Lazar et al. (2006, *Proc. Natl. Acad. Sci. U.S.A.* 103(11): 4005-4010) and Okazaki et al. (2004, *J. Mol. Biol.* 336(5): 1239-49). See also WO 03/074679, WO 2004/029207, WO 2004/099249, WO2006/047350, WO 2006/019447, WO 2006/105338, WO 2007/041635. It is also possible to use cell lines specifically engineered for production of improved antibodies. In particular, these lines have altered regulation of the glycosylation pathway, for example resulting in antibodies which are poorly fucosylated or even totally defucosylated. Such cell lines and methods for engineering them are disclosed in e.g. Shinkawa et al. (2003, *J. Biol.*

Chem. 278(5): 3466-3473), Ferrara et al. (2006, *J. Biol. Chem.* 281(8): 5032-5036; 2006, *Biotechnol. Bioeng.* 93(5): 851-61), EP 1 272 527 B1, EP 1 331 266, EP 1 498 490, EP 1 498 491, EP 1 676 910, EP 1 792 987, and WO 99/54342.

Further embodiments of the invention include antibodies of the invention or antigen binding fragments thereof coupled to a non-proteinaeous polymer such as polyethylene glycol (PEG), polypropylene glycol or polyoxyalkylene. Conjugation of proteins to PEG is an established technique for increasing half-life of proteins, as well as reducing antigenicity and immunogenicity of proteins. The use of PEGylation with different molecular weights and styles (linear or branched) has been investigated with intact antibodies as well as Fab' fragments (Koumenis I. L. et al., 2000, *Int. J. Pharmaceut.* 198: 83-95).

The present invention also includes cytotoxic conjugates, or antibody-drug conjugates, or conjugates. As used herein, all these terms have the same meaning and are interchangeable.

These cytotoxic conjugates comprise two primary components, a cell-binding agent and a cytotoxic agent.

As used herein, the term "cell binding agent" refers to an agent that specifically recognizes and binds the EphA2 receptor on the cell surface. In one embodiment, the cell binding agent specifically recognizes the EphA2 receptor such that it allows the conjugate to act in a targeted fashion with little side-effects resulting from non-specific binding.

In another embodiment, the cell binding agent of the present invention also specifically recognizes the EphA2 receptor so that the conjugate will be in contact with the target cell for a sufficient period of time to allow the cytotoxic drug portion of the conjugate to act on the cell, and/or to allow the conjugates to be internalized by the cell.

In a preferred embodiment, the cytotoxic conjugates comprise an anti-EphA2 antibody as the cell binding agent, more preferably the murine 2H11R35R74 monoclonal antibody. In a more preferred embodiment, the cytotoxic conjugate comprises a humanized 2H11R35R74 antibody or an epitope-binding fragment thereof. The 2H11R35R74 antibody is able to specifically recognize an EphA receptor, such as EphA2, and directs the cytotoxic agent to an abnormal cell or a tissue, such as cancer cells, in a targeted fashion.

The second component of the cytotoxic conjugates of the present invention is a cytotoxic agent. The term "cytotoxic agent", as used herein, refers to a substance that reduces or blocks the function, or growth, of cells and/or causes destruction of cells.

In preferred embodiments, the cytotoxic agent is a taxoid, a maytansinoid such as DM1 or DM4, a small drug, a tomaymycin derivative, a prodrug, CC-1065 or a CC-1065 analog. In preferred embodiments, the cell binding agents of the present invention are covalently attached, directly or via a cleavable or non-cleavable linker, to the cytotoxic agent. "Linker", as used herein, means a chemical moiety comprising a covalent bond or a chain of atoms that covalently attaches an antibody to a drug moiety.

Thus, this invention contemplates the use of conjugates between (1) a cell binding agent that recognizes and binds the EphA2 receptor, and (2) a cytotoxic agent. In the cytotoxic conjugates, the cell binding agent has a high affinity for the EphA2 receptor and the cytotoxic agent has a high degree of cytotoxicity for cells expressing the EphA2 receptor, such that the cytotoxic conjugates of the present invention form effective killing agents.

Conjugates of antagonistic EphA2 antibodies have been previously described. For example, WO 2008/010101 disclosed humanized 37.3D7 and humanized 53.2H11 antibodies conjugated to L-DM4, N2' deacetyl-N2'(4-methyl-4-mercapto-1-oxopentyl)-maytansine, using SPDB (4-[2-pyridyldithio]butanoic acid N-hydroxysuccinimide ester) linker (see Example 10 of WO 2008/010101; hu37.3D7-SPDB-DM4 and hu2H11-SPDB-DM4).

When conjugated to a cytotoxic agent, the antibodies of the invention show a number of advantageous properties over the antibodies of the prior art. In particular, conjugation does not affect the affinity of the antibodies of the invention for the EphA2 receptor, whereas the binding of 53.2H11 to EphA2 is negatively affected by the attachment of a cytotoxic agent onto said 53.2H11 antibody.

The cell binding agents, cytotoxic agents, and linkers are discussed in more detail below.

Cell Binding Agents

The effectiveness of the compounds of the present invention as therapeutic agents depends on the careful selection of an appropriate cell binding agent. Cell binding agents may be of any kind presently known, or that become known, and includes peptides and non-peptides. The cell binding agent may be any compound that can bind a cell, either in a specific or non-specific manner. Generally, these can be antibodies (especially monoclonal antibodies), lymphokines, hormones, growth factors, vitamins, nutrient-transport molecules (such as transferrin), or any other cell binding molecule or substance.

More specific examples of cell binding agents that can be used include:

polyclonal antibodies;
monoclonal antibodies;
fragments of antibodies such as Fab, Fab', and F(ab')$_2$, Fv (Parham, 1983, *J. Immunol.*, 131:2895-2902; Spring et al., 1974, *J. Immunol.*, 113: 470-478; Nisonoff et al., 1960, *Arch. Biochem. Biophys.*, 89: 230-244).

Preferably, a humanized anti-EphA2 antibody is used as the cell binding agent of the present invention. More preferably the humanized anti-EphA2 antibody is a humanized 2H11R35R74 antibody.

Cytotoxic Agents

In another embodiment, the humanized antibody or an epitope-binding fragment thereof can be conjugated to a drug, such as a maytansinoid, a tomaymycin derivative or a duocarmycin derivative to form a prodrug having specific cytotoxicity towards antigen-expressing cells by targeting the drug to the EphA2 receptor. Cytotoxic conjugates comprising such antibodies and a small, highly toxic drug (e.g., maytansinoids, tomaymycin derivatives, and CC-1065 and CC-1065 analogs) can be used as a therapeutic for treatment of tumors, such as, for example, breast and ovarian tumors.

The cytotoxic agent used in the cytotoxic conjugate of the present invention may be any compound that results in the death of a cell, or induces cell death, or in some manner decreases cell viability. Preferred cytotoxic agents include, for example, maytansinoids and maytansinoid analogs, tomaymycin derivatives, and CC-1065 and CC-1065 analogs, defined below. These cytotoxic agents are conjugated to the antibodies, antibody fragments, functional equivalents, improved antibodies and their analogs as disclosed herein.

The cytotoxic conjugates may be prepared by in vitro methods. In order to link a drug or prodrug to the antibody, a linking group is used. Suitable linking groups are well known in the art and include disulfide groups, thioether groups, acid labile groups, photolabile groups, peptidase labile groups and esterase labile groups.

Exemplary linking groups are disulfide groups and thioether groups. For example, conjugates can be constructed using a disulfide exchange reaction or by forming a thioether bond between the antibody and the drug or prodrug. Examples of linkers carrying such linking groups include N-succinimidyl pyridyldithiopropionate (SPDP) and N-succinimidyl pyridyldithiobutyrate (SPDB), whose dithiopyridyl reactive group (see Bourdon M. A. et al., *Biochem. J.,* 173: 723-737, 1978; U.S. Pat. No. 5,208,020) reacts with a cytotoxic chemical reactive group such as —SH to form a new bond —S—S—. The N-succinimidyloxy group then preferentially reacts with the amino groups present on the antibody in order to form amide bonds.

In another preferred embodiment, the cytotoxic agent is linked to the cell binding agent using polyethylene glycol (PEG) linking groups, as set forth in U.S. Pat. No. 6,716,821. Exemplary PEG linking groups include heterobifunctional PEG linkers that bind to cytotoxic agents and cell binding agents through a functional sulfhydryl or disulfide group at one end, and an active ester at the other end (U.S. Pat. No. 6,716,821). It is also possible to use PEG linkers which do not bind to cytotoxic agents through a functional sulfhydryl or disulfide group.

Specifically contemplated is a cytotoxic agent bearing a polyethylene glycol (PEG) linking group having a terminal active ester, of formula (I):

(I)

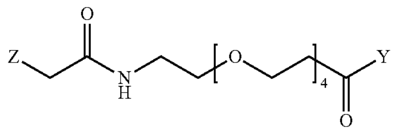

wherein Z is said cytotoxic agent, said cytotoxic agent being selected from the group of maytansinoids and maytansinoid analogs, tomaymycin derivatives, and CC-1065 and CC-1065 analogs, and wherein Y is Y is N-succinimidyloxy, N-sulfosuccinimidyloxy, N-phthalimidyloxy, N-sulfophthalimidyloxy, 2-nitrophenyloxy, 4-nitrophenyloxy, 2,4-dinitrophenyloxy, 3-sulfonyl-4-nitrophenyloxy, 3-carboxy-4-nitrophenyloxy, imidazolyl, or halogen atom.

In another preferred embodiment, a cytotoxic agent is provided, said cytotoxic agent bearing a polyethylene glycol (PEG) linking group having a terminal active ester, and of formula (II):

(II)

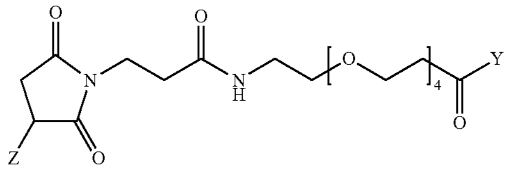

wherein Z is said cytotoxic agent, said cytotoxic agent being selected from the group of maytansinoids and maytansinoid analogs, tomaymycin derivative, and CC-1065 and CC-1065 analogs, and wherein Y is Y is N-succinimidyloxy, N-sulfosuccinimidyloxy, N-phthalimidyloxy, N-sulfophthalimidyloxy, 2-nitrophenyloxy, 4-nitrophenyloxy, 2,4-dinitrophenyloxy, 3-sulfonyl-4-nitrophenyloxy, 3-carboxy-4-nitrophenyloxy, imidazolyl, or halogen atom.

Preparation of the Conjugate

In general, the conjugate can be obtained by a process comprising the steps of:

(i) bringing into contact an optionally-buffered aqueous solution of a cell-binding agent with a solution of a cytotoxic compound;

(ii) then optionally separating the conjugate which was formed in (i) from the unreacted reagents and any aggregate which may be present in the solution.

In one aspect, the cell-binding agent is an antibody; more specifically, the cell-binding agent is the mu2H11R35R74 antibody or a humanized version thereof. In another aspect, the cytotoxic agent is a compound of either formula (I) or (II), wherein Z is a maytansinoid; in particular, Z is DM4.

It is understood that conjugates obtainable by this process are comprised within the scope of the invention.

The aqueous solution of cell-binding agent can be buffered with buffers such as, e.g. potassium phosphate or N-2-Hydroxyethylpiperazine-N'-2-ethanesulfonic acid (Hepes buffer). The buffer depends upon the nature of the cell-binding agent. The cytotoxic compound is in solution in an organic polar solvent, e.g. dimethyl sulfoxide (DMSO) or dimethylacetamide (DMA).

The reaction temperature is usually comprised between 20 and 40° C. The reaction time can vary from 1 to 24 hours. The reaction between the cell-binding agent and the cytotoxic agent can be monitored by size exclusion chromatography (SEC) with a refractometric and/or UV detector. If the conjugate yield is too low, the reaction time can be extended.

A number of different chromatography methods can be used by the person skilled in the art in order to perform the separation of step (ii): the conjugate can be purified e.g. by SEC, adsorption chromatography (such as ion exchange chromatography, IEC), hydrophobic interaction chromatograhy (HIC), affinity chromatography, mixed-support chromatography such as hydroxyapatite chromatography, or high performance liquid chromatography (HPLC). Purification by dialysis or diafiltration can also be used.

An example of a process which can be used is described in the Example I.b.1.

As used herein, the term "aggregates" means the associations which can be formed between two or more cell-binding agents, said agents being modified or not by conjugation. The aggregates can be formed under the influence of a great number of parameters, such as a high concentration of cell-binding agent in the solution, the pH of the solution, high shearing forces, the number of bonded dimers and their hydrophobic character, the temperature (see Wang & Gosh, 2008, *J. Membrane Sci.,* 318: 311-316, and references cited therein); note that the relative influence of some of these parameters is not clearly established. In the case of proteins and antibodies, the person skilled in the art will refer to Cromwell et al. (2006, *AAPS Jounal,* 8 (3): E572-E579). The content in aggregates can be determined with techniques well known to the skilled person, such as SEC (see Walter et al., 1993, *Anal. Biochem.,* 212(2): 469-480).

After step (i) or (ii), the conjugate-containing solution can be submitted to an additional step (iii) of ultrafiltration and/or diafiltration.

The conjugate is recovered at the end of these steps in an aqueous solution.

Maytansinoids

Among the cytotoxic agents that may be used in the present invention to form a cytotoxic conjugate, are maytansinoids and maytansinoid analogs. Examples of suitable maytansinoids include maytansinol and maytansinol analogs. Maytansinoids are drugs that inhibit microtubule formation and that are highly toxic to mammalian cells.

Examples of suitable maytansinol analogues include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Specific examples of suitable analogues of maytansinol having a modified aromatic ring include:

(1) C-19-dechloro (U.S. Pat. No. 4,256,746) (prepared by LAH reduction of ansamytocin P2);

(2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and (3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:

(1) C-9-SH (U.S. Pat. No. 4,424,219) (prepared by the reaction of maytansinol with $H_2S$ or $P_2S_5$);

(2) C-14-alkoxymethyl (demethoxy/$CH_2OR$) (U.S. Pat. No. 4,331,598);

(3) C-14-hydroxymethyl or acyloxymethyl ($CH_2OH$ or $CH_2OAc$) (U.S. Pat. No. 4,450,254) (prepared from *Nocardia*);

(4) C-15-hydroxy/acyloxy (U.S. Pat. No. 4,364,866) (prepared by the conversion of maytansinol by *Streptomyces*);

(5) C-15-methoxy (U.S. Pat. Nos. 4,313,946 and 4,315,929) (isolated from *Trewia nudiflora*);

(6) C-18-N-demethyl (U.S. Pat. Nos. 4,362,663 and 4,322,348) (prepared by the demethylation of maytansinol by *Streptomyces*); and (7) 4,5-deoxy (U.S. Pat. No. 4,371,533) (prepared by the titanium trichloride/LAH reduction of maytansinol).

In a preferred embodiment, the cytotoxic conjugates of the present invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (III):

(III)

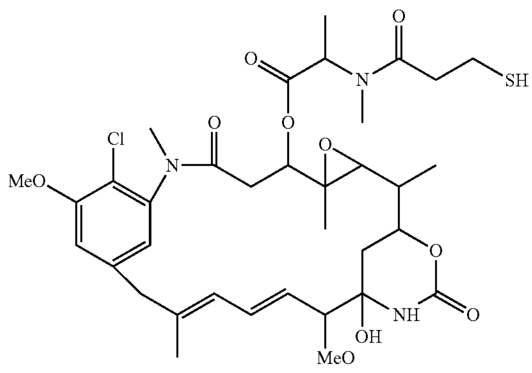

In another preferred embodiment, the cytotoxic conjugates of the present invention utilize the thiol-containing maytansinoid DM4, formally termed $N^{2'}$-deacetyl-$N^{2'}$(4-methyl-4-mercapto-1-oxopentyl)-maytansine, as the cytotoxic agent. DM4 is represented by the following structural formula (IV):

(IV)

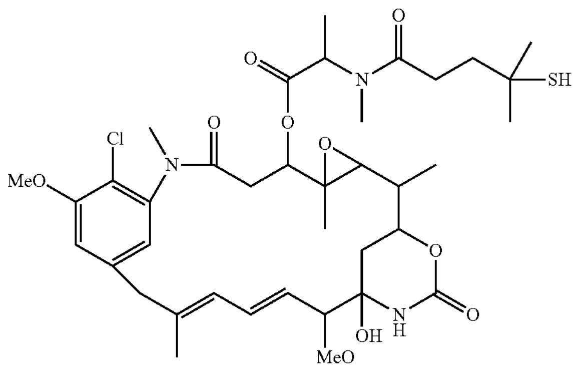

In further embodiments of the invention, other maytansines, including thiol and disulfide-containing maytansinoids bearing a mono or di-alkyl substitution on the carbon atom bearing the sulfur atom, may be used. These include a maytansinoid having, at C-3, C-14 hydroxymethyl, C-15 hydroxy, or C-20 desmethyl, an acylated amino acid side chain with an acyl group bearing a hindered sulfhydryl group, wherein the carbon atom of the acyl group bearing the thiol functionality has one or two substituents, said substituents being $CH_3$, $C_2H_5$, linear or branched alkyl or alkenyl having from 1 to 10 carbon atoms, cyclic alkyl or alkenyl having from 3 to 10 carbon atoms, phenyl, substituted phenyl, or heterocyclic aromatic or heterocycloalkyl radical, and further wherein one of the substituents can be H, and wherein the acyl group has a linear chain length of at least three carbon atoms between the carbonyl functionality and the sulfur atom.

Such additional maytansines include compounds represented by formula (V):

(V)

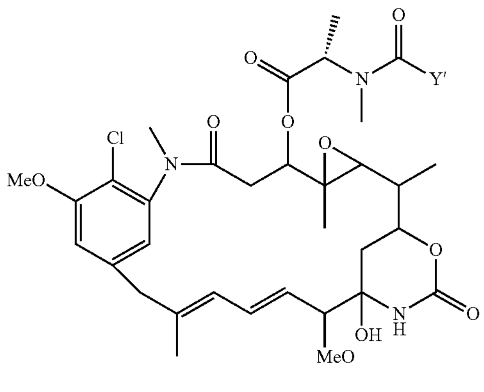

wherein:

Y' represents $$(CR_7R_8)_l(CR_9{=}CR_{10})_p(C{\equiv}C)_qA_r(CR_5R_6)_mD_u(CR_{11}{=}CR_{12})_r(C{\equiv}C)_sB_t(CR_3R_4)_nCR_1R_2SZ,$$

wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and in addition $R_2$ can be H;

A, B, D are cycloalkyl or cycloalkenyl having 3-10 carbon atoms, simple or substituted aryl or heterocyclic aromatic or heterocycloalkyl radical;

$R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical;

l, m, n, o, p, q, r, s, and t are each independently 0 or an integer of from 1 to 5, provided that at least two of l, m, n, o, p, q, r, s and t are not zero at any one time; and Z is H, SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (V) include compounds of formula (V) wherein:

$R_1$ is methyl, $R_2$ is H and Z is H.

$R_1$ and $R_2$ are methyl and Z is H.

$R_1$ is methyl, $R_2$ is H, and Z is —$SCH_3$.

$R_1$ and $R_2$ are methyl, and Z is —$SCH_3$.

Such additional maytansines also include compounds represented by formula (VI-L), (VI-D), or (VI-D,L):

(VI-L)

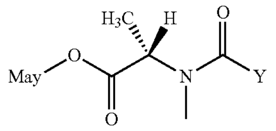

(VI-D)

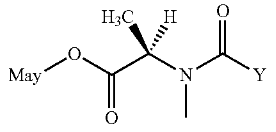

(VI-D,L)

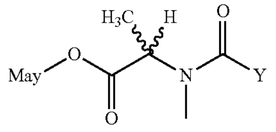

wherein:

Y represents $(CR_7R_8)_l(CR_5R_6)_m(CR_3R_4)_nCR_1R_2SZ$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical;

l, m and n are each independently an integer of from 1 to 5, and in addition n can be 0;

Z is H, SR or —COR wherein R is linear or branched alkyl or alkenyl having from 1 to 10 carbon atoms, cyclic alkyl or alkenyl having from 3 to 10 carbon atoms, or simple or substituted aryl or heterocyclic aromatic or heterocycloalkyl radical; and May represents a maytansinoid which bears the side chain at C-3, C-14 hydroxymethyl, C-15 hydroxy or C-20 desmethyl.

Preferred embodiments of formulas (VI-L), (VI-D) and (VI-D,L) include compounds of formulas (VI-L), (VI-D) and (VI-D,L) wherein:

$R_1$ is methyl, $R_2$ is H, $R_5$, $R_6$, $R_7$, and $R_8$ are each H, l and m are each 1, n is 0, and Z is H.

$R_1$ and $R_2$ are methyl, $R_5$, $R_6$, $R_7$, $R_8$ are each H, l and m are 1, n is 0, and Z is H.

$R_1$ is methyl, $R_2$ is H, $R_5$, $R_6$, $R_7$, and $R_8$ are each H, l and m are each 1, n is 0, and Z is —$SCH_3$.

$R_1$ and $R_2$ are methyl, $R_5$, $R_6$, $R_7$, $R_8$ are each H, l and m are 1, n is 0, and Z is —$SCH_3$.

Preferably the cytotoxic agent is represented by formula (VI-L).

Such additional maytansines also include compounds represented by formula (VII):

(VII)

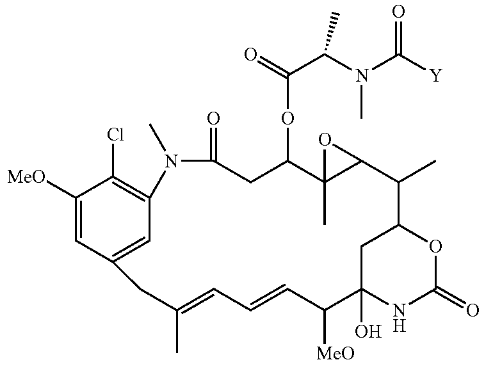

wherein:

Y represents $(CR_7R_8)_l(CR_5R_6)_m(CR_3R_4)_nCR_1R_2SZ$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical;

l, m and n are each independently an integer of from 1 to 5, and in addition n can be 0; and Z is H, SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (VII) include compounds of formula (VII) wherein:

$R_1$ is methyl, $R_2$ is H, R5, R6, R7, and R8 are each H; l and m are each 1; n is 0; and Z is H.

$R_1$ and $R_2$ are methyl; $R_5$, $R_6$, $R_7$, $R_8$ are each H, l and m are 1; n is 0; and Z is H.

$R_1$ is methyl, $R_2$ is H, $R_5$, $R_6$, $R_7$, and $R_8$ are each H, l and m are each 1, n is 0, and Z is —$SCH_3$.

$R_1$ and $R_2$ are methyl, $R_5$, $R_6$, $R_7$, $R_8$ are each H, l and m are 1, n is 0, and Z is —$SCH_3$.

Such additional maytansines further include compounds represented by formula (VIII-L), (VIII-D), or (VIII-D,L):

(VIII-L)

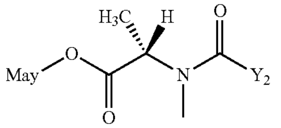

(VIII-D)

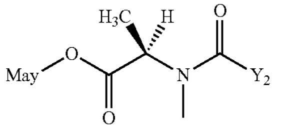

(VIII-D,L)

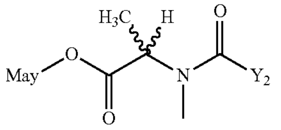

wherein:

$Y_2$ represents $(CR_7R_8)_l(CR_5R_6)_m(CR_3R_4)_nCR_1R_2SZ_2$, wherein:

- $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and in addition $R_2$ can be H;
- $R_3$, $R_4$, $R_5$, $R_6$, $R_7$ and $R_8$ are each independently H, $CH_3$, $C_2H_5$, linear cyclic alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical;
- l, m and n are each independently an integer of from 1 to 5, and in addition n can be 0;
- $Z_2$ is SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical; and May is a maytansinoid.

Such additional maytansines also include compounds represented by formula (IX):

(IX)

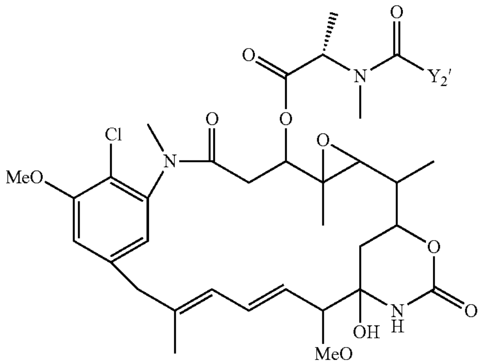

wherein:

$Y_2'$ represents $$(CR_7R_8)_l(CR_9{=}CR_{10})_p(C{\equiv}C)_qA_r(CR_5R_6)_mD_u(CR_{11}{=}CR_{12})_r(C{\equiv}C)_sB_t(CR_3R_4)_nCR_1R_2SZ_2,$$

wherein:

- $R_1$ and $R_2$ are each independently $CH_3$, $C_2H_5$, linear branched or alkyl or alkenyl having from 1 to 10 carbon atoms, cyclic alkyl or alkenyl having from 3 to 10 carbon atoms, phenyl, substituted phenyl or heterocyclic aromatic or heterocycloalkyl radical, and in addition $R_2$ can be H;
- A, B, and D each independently is cycloalkyl or cycloalkenyl having 3 to 10 carbon atoms, simple or substituted aryl, or heterocyclic aromatic or heterocycloalkyl radical;
- $R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical;
- l, m, n, o, p, q, r, s, and t are each independently 0 or an integer of from 1 to 5, provided that at least two of l, m, n, o, p, q, r, s and t are not zero at any one time; and $Z_2$ is SR or —COR, wherein R is linear alkyl or alkenyl having from 1 to 10 carbon atoms, branched or cyclic alkyl or alkenyl having from 3-10 carbon atoms, or simple or substituted aryl or heterocyclic aromatic or heterocycloalkyl radical.

Preferred embodiments of formula (IX) include compounds of formula (IX) wherein: $R_1$ is methyl, $R_2$ is H.

The above-mentioned maytansinoids can be conjugated to anti-EphA antibody 2H11R35R74 or a homologue or fragment thereof, wherein the antibody is linked to the maytansinoid using the thiol or disulfide functionality that is present on the acyl group of an acylated amino acid side chain found at C-3, C-14 hydroxymethyl, C-15 hydroxy or C-20 desmethyl of the maytansinoid, and wherein the acyl group of the acylated amino acid side chain has its thiol or disulfide functionality located at a carbon atom that has one or two substituents, said substituents being $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and in addition one of the substituents can be H, and wherein the acyl group has a linear chain length of at least three carbon atoms between the carbonyl functionality and the sulfur atom.

A preferred conjugate of the present invention is the one that comprises the anti-EphA antibody 2H11R35R74 or a homologue or fragment thereof, conjugated to, or obtainable by conjugation with, a maytansinoid of formula (X):

(X)

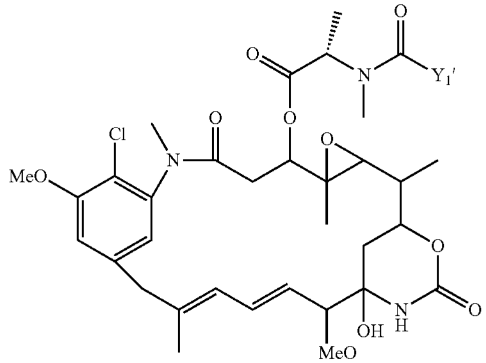

wherein:

$Y_1'$ represents $$(CR_7R_8)_l(CR_9{=}CR_{10})_p(C{\equiv}C)_qA_r(CR_5R_6)_mD_u(CR_{11}{=}CR_{12})_r(C{\equiv}C)_sB_t(CR_3R_4)_nCR_1R_2S—,$$

wherein:

A, B, and D, each independently is cycloalkyl or cycloalkenyl having 3-10 carbon atoms, simple or substituted aryl, or heterocyclic aromatic or heterocycloalkyl radical;

$R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical; and l, m, n, o, p, q, r, s, and t are each independently 0 or an integer of from 1 to 5, provided that at least two of l, m, n, o, p, q, r, s and t are non-not zero at any one time.

Preferably, $R_1$ is methyl, $R_2$ is H, or $R_1$ and $R_2$ are methyl.

An even more preferred conjugate of the present invention is the one that comprises the anti-EphA antibody 2H11R35R74 or a homologue or fragment thereof, conjugated to a maytansinoid of formula (XI-L), (XI-D), or (XI-D, L):

(XI-L)

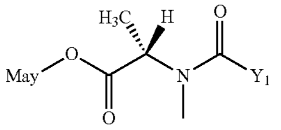

(XI-D)

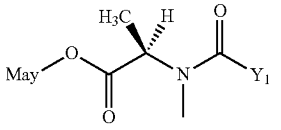

(XI-D,L)

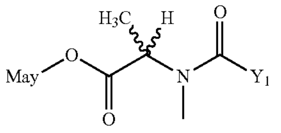

wherein:

$Y_1$ represents $(CR_7R_8)_l(CR_5R_6)_m(CR_3R_4)_nCR_1R_2S$—, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, heterocyclic aromatic or heterocycloalkyl radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical;

l, m and n are each independently an integer of from 1 to 5, and in addition n can be 0; and May represents a maytansinol which bears the side chain at C-3, C-14 hydroxymethyl, C-15 hydroxy or C-20 desmethyl.

Preferred embodiments of formulas (XI-L), (XI-D) and (XI-D,L) include compounds of formulas (XI-L), (XI-D) and (XI-D,L) wherein:

$R_1$ is methyl, $R_2$ is H, or $R_1$ and $R_2$ are methyl, $R_1$ is methyl, $R_2$ is H, $R_5$, $R_6$, $R_7$ and $R_8$ are each H; l and m are each 1; n is 0, $R_1$ and $R_2$ are methyl; $R_5$, $R_6$, $R_7$ and $R_8$ are each H; l and m are 1; n is 0.

Preferably the cytotoxic agent is represented by formula (XI-L).

A further preferred conjugate of the present invention is the one that comprises the anti-EphA antibody 2H11R35R74 or a homologue or fragment thereof, conjugated to a maytansinoid of formula (XII):

(XII)

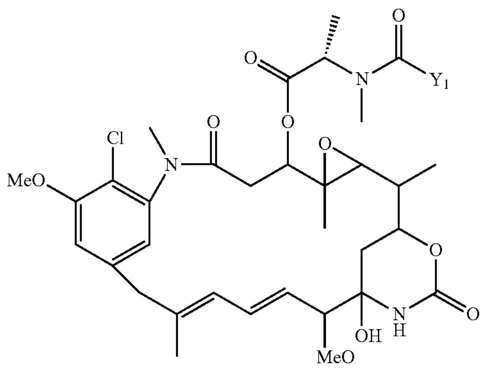

wherein the substituents are as defined for formula (XI) above.

Especially preferred are any of the above-described compounds, wherein $R_1$ is H, $R_2$ is methyl, $R_5$, $R_6$, $R_7$ and $R_8$ are each H, l and m are each 1, and n is 0.

Further especially preferred are any of the above-described compounds, wherein $R_1$ and $R_2$ are methyl, $R_5$, $R_6$, $R_7$, $R_8$ are each H, l and m are 1, and n is 0

Further, the L-aminoacyl stereoisomer is preferred.

Each of the maytansinoids taught in pending U.S. patent application Ser. No. 10/849,136, filed May 20, 2004, may also be used in the cytotoxic conjugate of the present invention. The entire disclosure of U.S. patent application Ser. No. 10/849,136 is incorporated herein by reference.

Disulfide-Containing Linking Groups

In order to link the maytansinoid to a cell binding agent, such as the 2H11R35R74 antibody, the maytansinoid comprises a linking moiety. The linking moiety contains a chemical bond that allows for the release of fully active maytansinoids at a particular site. Suitable chemical bonds are well known in the art and include disulfide bonds, acid labile bonds, photolabile bonds, peptidase labile bonds and esterase labile bonds.

The linking moiety also comprises a reactive chemical group. In a preferred embodiment, the reactive chemical group is used to covalently bind to the maytansinoid via a disulfide bond linking moiety.

Particularly preferred reactive chemical groups are N-succinimidyl esters and N-sulfosuccinimidyl esters.

Particularly preferred maytansinoids comprising a linking moiety that contains a reactive chemical group are C-3 esters of maytansinol and its analogs where the linking moiety contains a disulfide bond and the chemical reactive group comprises a N-succinimidyl or N-sulfosuccinimidyl ester.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. However the C-3 position is preferred and the C-3 position of maytansinol is especially preferred.

While the synthesis of esters of maytansinol having a linking moiety is described in terms of disulfide bond-containing linking moieties, one of skill in the art will understand that linking moieties with other chemical bonds (as described above) can also be used with the present invention, as can other maytansinoids. Specific examples of other chemical bonds include acid labile bonds, photolabile bonds, peptidase labile bonds and esterase labile bonds. The disclosure of U.S.

Pat. No. 5,208,020, incorporated herein, teaches the production of maytansinoids bearing such bonds.

The synthesis of maytansinoids and maytansinoid derivatives having a disulfide moiety that bears a reactive group is described in U.S. Pat. Nos. 6,441,163 and 6,333,410, and U.S. application Ser. No. 10/161,651, each of which is herein incorporated by reference.

PEG-Containing Linking Groups

Maytansinoids may also be linked to cell binding agents using PEG linking groups, as set forth in U.S. Pat. No. 6,716,821. These PEG linking groups are soluble both in water and in non-aqueous solvents, and can be used to join one or more cytotoxic agents to a cell binding agent. Exemplary PEG linking groups include heterobifunctional PEG linkers that bind to cytotoxic agents and cell binding agents at opposite ends of the linkers through a functional sulfhydryl or disulfide group at one end, and an active ester at the other end.

As a general example of the synthesis of a cytotoxic conjugate using a PEG linking group, reference is again made to U.S. Pat. No. 6,716,821 for specific details. Synthesis begins with the reaction of one or more cytotoxic agents bearing a reactive PEG moiety with a cell-binding agent, resulting in displacement of the terminal active ester of each reactive PEG moiety by an amino acid residue of the cell binding agent, such as the 2H11R35R74 antibody, to yield a cytotoxic conjugate comprising one or more cytotoxic agents covalently bonded to a cell binding agent through a PEG linking group. It is also possible to use PEG linking groups which do not bind to cytotoxic agents through a functional sulfhydryl or disulfide group.

Thus comprised within the scope of the invention is the maytansinoid of formula (XIII), herein referred to as PEG4-NHAc-DM4:

(XIII)

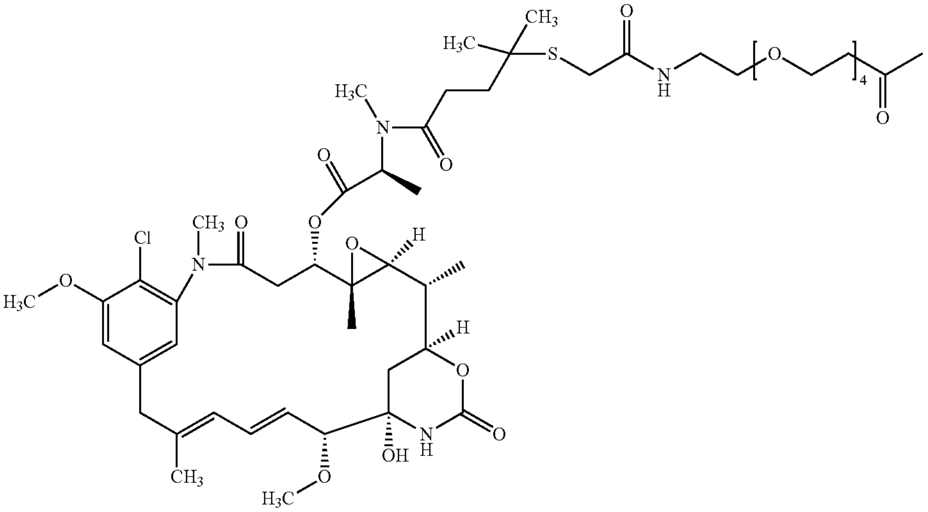

Also comprised within the meaning of the invention is the maytansinoid of formula (XIV), herein referred to as PEG4-Mal-DM4:

(XIV)

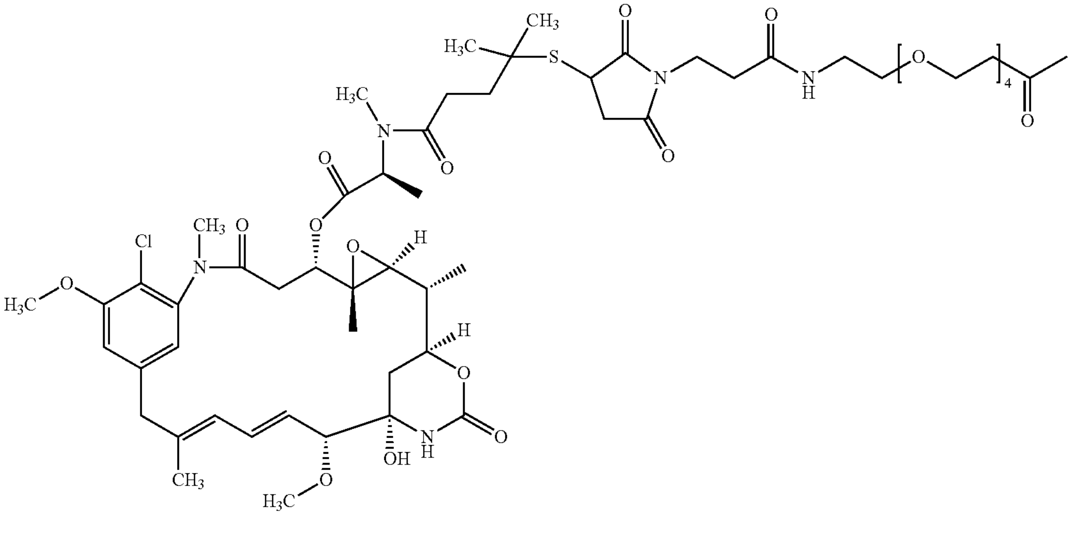

Also comprised within the meaning of the invention is the maytansinoid of formula (XXIV), herein referred to as SPDB-DM4:

(XXIV)

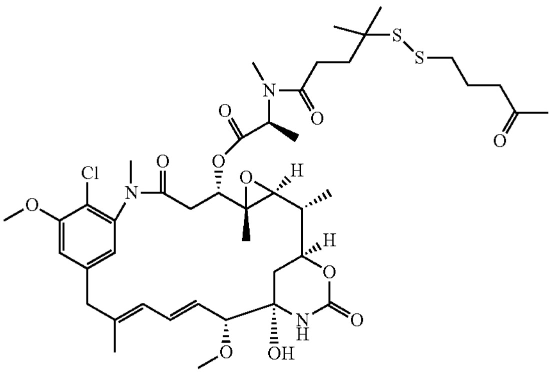

Also comprised within the meaning of the invention is the maytansinoid of formula (XXV), herein referred to as: PEG4-NMeAc-DM4

(XXV)

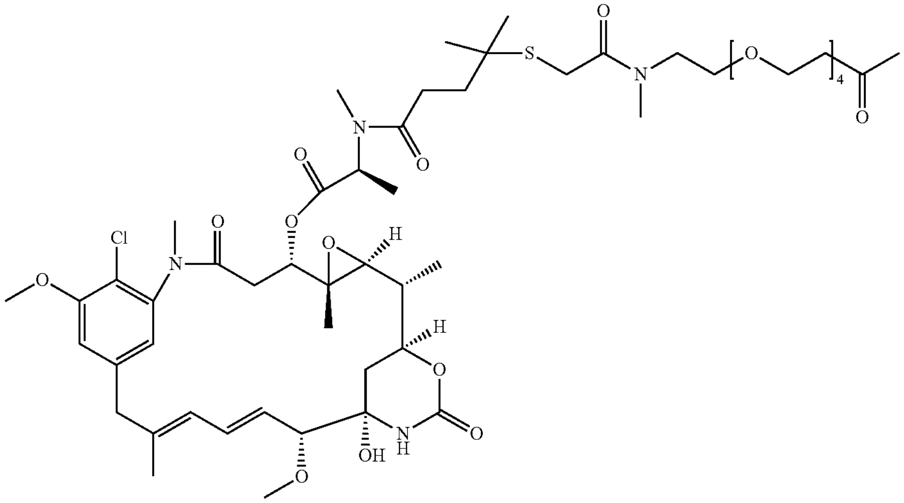

Also comprised within the meaning of the invention is the maytansinoid of formula (XXVI), herein referred to as: PEG8-NHAc-DM4

(XXVI)

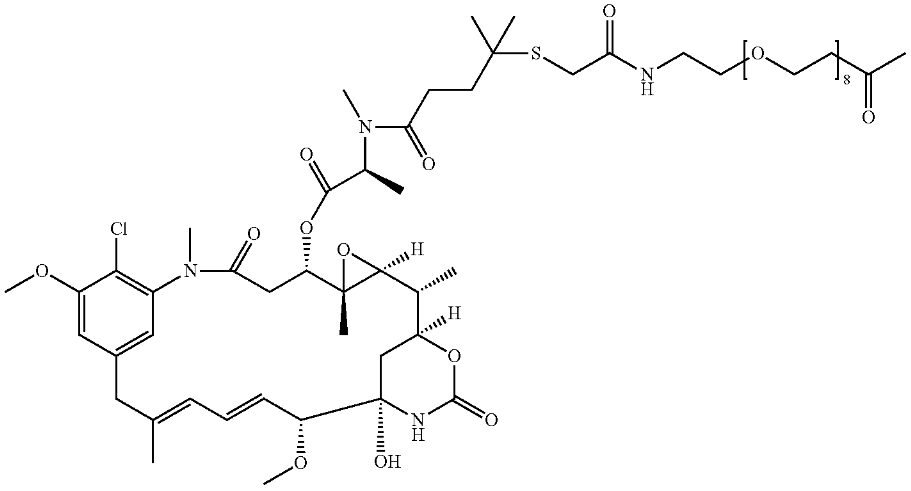

Also comprised within the meaning of the invention is the maytansinoid of formula (XXVII), herein referred to as: PEG4-Allyl-DM4 noid of formula (XIV) is conjugated to the 2H11R35R74 antibody of the invention to yield a 2H11R35R74-PEG4-Mal-DM4 conjugate.

(XXVII)

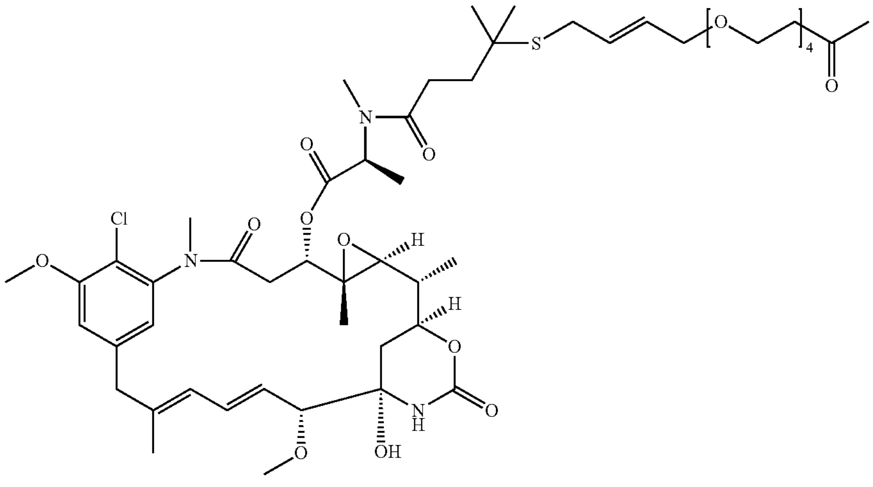

The reactive group-containing maytansinoids, such as DM4, are reacted with an antibody, such as the 2H11R35R74 antibody, to produce cytotoxic conjugates, wherein the cytotoxic is covalently attached to the antibody. These conjugates may be purified by HPLC or by gel-filtration.

Thus, a preferred embodiment is drawn to an antibody-drug conjugate having a structure consisting of the structure of the formula (XV):

(XV)

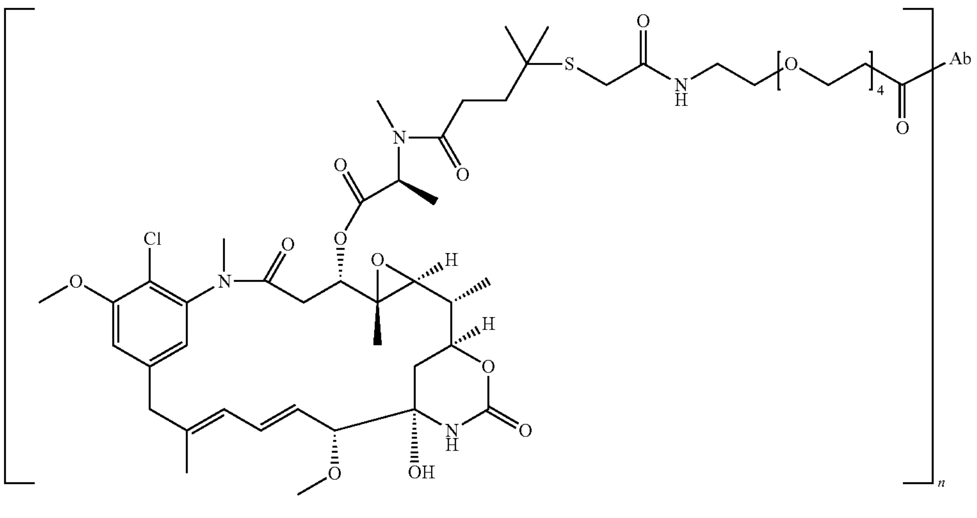

A preferred embodiment of the invention is a conjugate of the 2H11R35R74 antibody, or of a humanized version thereof, said conjugate comprising a cytotoxic agent attached covalently to said 2H11R35R74 antibody, said cytotoxic agent being chosen between the maytansinoid of formula (XIII) and the maytansinoid of formula (XIV). In a more preferred embodiment, the conjugation of the maytansinoid of formula (XIII) to the 2H11R35R74 antibody of the invention will result in a 2H11R35R74-PEG4-NHAc-DM4 conjugate. In another further preferred embodiment, the maytansinoid of formula (XIV) is conjugated to the 2H11R35R74 antibody of the invention to yield a 2H11R35R74-PEG4-Mal-DM4 conjugate.

wherein Ab is an antibody of the invention and n is an integer comprised between 1 and 15. Preferentially, n is comprised between 1 and 10. Even more preferentially, n is comprised between 5 and 7. In another further preferred embodiment, the antibody of the invention is the 2H11R35R74 antibody or a humanized version thereof, and the conjugate is a 2H11R35R74-PEG4-NHAc-DM4 conjugate.

Thus, another preferred embodiment is drawn to an antibody-drug conjugate having a structure consisting of the structure of the formula (XVI):

(XVI)

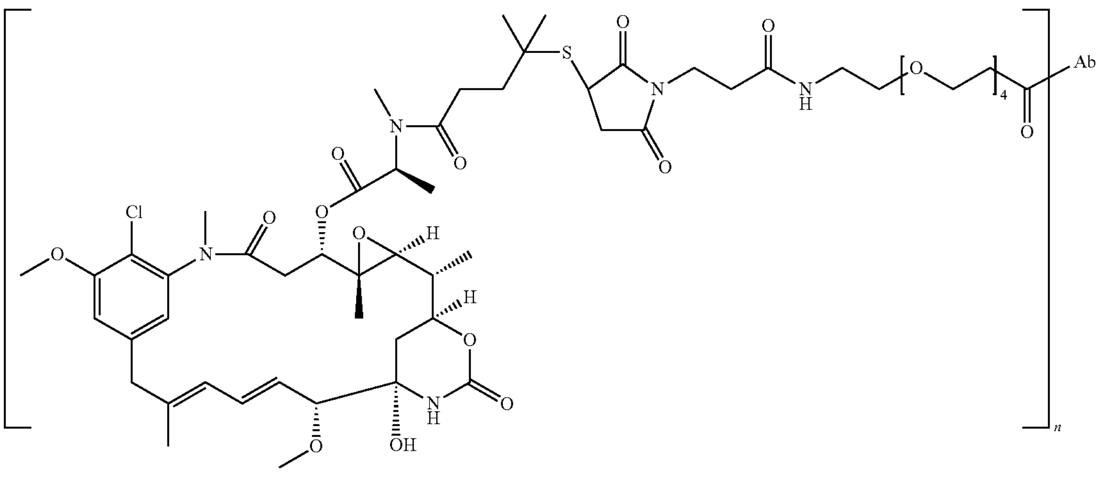

wherein Ab is an antibody of the invention and n is an integer comprised between 1 and 15. Preferentially, n is comprised between 1 and 10. Even more preferentially, n is comprised between 5 and 7. In another further preferred embodiment, the antibody of the invention is the 2H11R35R74 antibody or a humanized version thereof, and the conjugate is a 2H11R35R74-PEG4-Mal-DM4 conjugate.

Several excellent schemes for producing such antibody-maytansinoid conjugates are provided in U.S. Pat. No. 6,333,410, and U.S. application Ser. Nos. 09/867,598, 10/161,651 and 10/024,290, each of which is incorporated herein in its entirety.

As explained above, in general, the conjugate can be obtained by a process comprising the steps of:

(i) bringing into contact an optionally-buffered aqueous solution of an antibody with a solution of a maytansinoid;

(ii) then optionally separating the conjugate which was formed in (i) from the unreacted reagents and any aggregate which may be present in the solution.

More specifically, a solution of an antibody in aqueous buffer may be incubated with a molar excess of maytansinoid having a disulfide moiety that bears a reactive group. The reaction mixture can be quenched by addition of excess amine (such as ethanolamine, taurine, etc.). The maytansinoid-antibody conjugate may then be purified by gel-filtration.

In one aspect of the process, the antibody is the mu2H11R35R74 antibody or a humanized version thereof. In another aspect of that process, the cytotoxic agent is a cytotoxic agent chosen between:

the compound of formula (XVII):

(XVII)

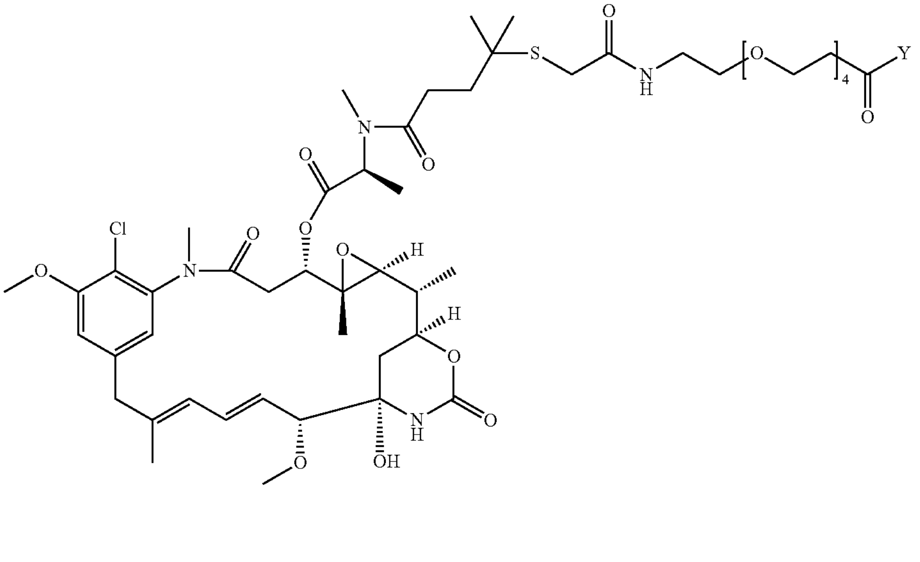

wherein Y is N-succinimidyloxy, N-sulfosuccinimidyloxy, N-phthalimidyloxy, N-sulfophthalimidyloxy, 2-nitrophenyloxy, 4-nitrophenyloxy, 2,4-dinitrophenyloxy, 3-sulfonyl-4-nitrophenyloxy, 3-carboxy-4-nitrophenyloxy, imidazolyl, or halogen atom; and the compound of formula (XVIII):

(XVIII)

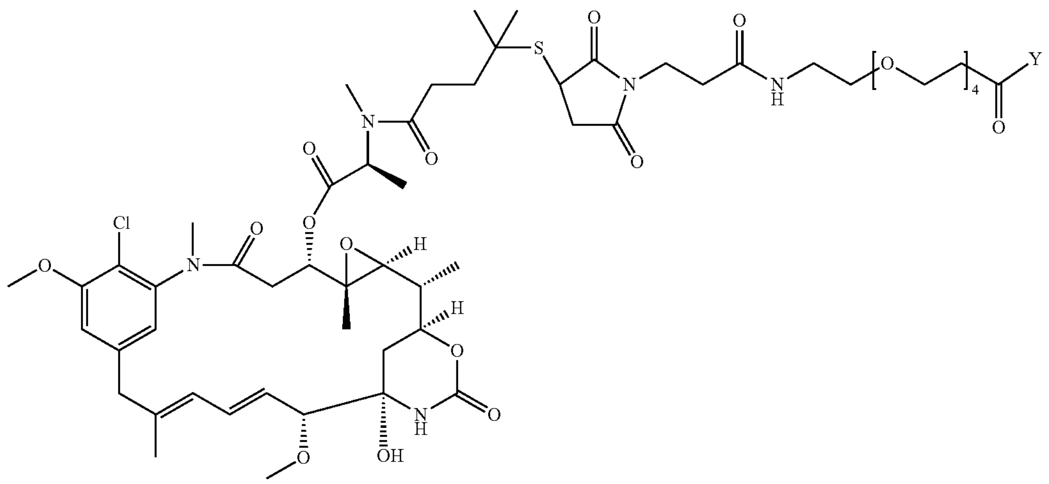

wherein Y is N-succinimidyloxy, N-sulfosuccinimidyloxy, N-phthalimidyloxy, N-sulfophthalimidyloxy, 2-nitrophenyloxy, 4-nitrophenyloxy, 2,4-dinitrophenyloxy, 3-sulfonyl-4-nitrophenyloxy, 3-carboxy-4-nitrophenyloxy, imidazolyl, or halogen atom.

An example of a process which can be used to with an antibody and a compound of either formula (XVII) or (XVIII) is given in Example I.

The number of maytansinoid molecules bound per antibody molecule ("drug-to-antibody ratio" or "DAR") can be determined spectrophotometrically by measuring the ratio of the absorbance at 252 nm and 280 nm of a solution of the substantially purified conjugate (that is after step (ii)). In particular, said DAR can be determined spectrophotometrically using the measured extinction coefficients at respectively 280 and 252 nm for the antibody: $\epsilon_{A280}$=224,000 $M^{-1}cm^{-1}$ and $\epsilon_{A252}$=82,880 $M^{-1}cm^{-1}$; assuming an average 160,000 molecular weight for the antibody, and for the maytansinoid, $\epsilon_{D280}$=5,180 $M^{-1}cm^{-1}$ and $\epsilon_{D252}$=26,159 $M^{-1}cm^{-1}$). The method of calculation is derived from Antony S. Dimitrov (ed), LLC, 2009, Therapeutic Antibodies and Protocols, vol 525, 445, Springer Science and is described in more details below:

The absorbances for the conjugate at 252 nm ($A_{252}$) and at 280 nm ($A_{280}$) are measured either on the monomeric peak of the SEC analysis (allowing to calculate the "DAR(SEC)" parameter) or using a classic spectrophotometer apparatus (allowing to calculate the "DAR(UV)" parameter). The absorbances can be expressed as follows:

$$A_{252}=(c_D\times\epsilon_{D252})+(c_A\times\epsilon_{A252})$$

$$A_{280}=(c_D\times\epsilon_{D280})+(c_A\times\epsilon_{A280})$$

wherein:

$c_D$ and $c_A$ are respectively the concentrations in the solution of the maytansinoid and of the antibody $\epsilon_{D252}$ and $\epsilon_{D280}$ are respectively the molar extinction coefficients of the maytansinoid at 252 nm and 280 nm $\epsilon_{A252}$ and $\epsilon_{A280}$ are respectively the molar extinction coefficients of the antibody at 252 nm and 280 nm.

Resolution of these two equations with two unknowns leads to the following equations:

$$c_D=[(\epsilon_{A280}\times A_{252})-(\epsilon_{A252}\times A_{280})]/[(\epsilon_{D252}\times\epsilon_{A280})-(\epsilon_{A252}\times\epsilon_{D280})]$$

$$c_A=[A_{280}-(c_D\times\epsilon_{D280})]/\epsilon_{A280}$$

The average DAR is then calculated from the ratio of the drug concentration to that of the antibody:

$$DAR=c_D/c_A$$

The average DAR measured with a UV spectrophometer (DAR(UV)) is more particularly above 4, more particularly between 4 and 10, even more particularly between 4 and 7, even more particularly between 5.5 and 8 and even more particularly between 5.9 and 7.5

In yet a further preferred embodiment, the invention comprises a conjugate of the 2H11R35R74 antibody, or of a humanized version thereof, and a compound of either formula (XVII) or (XVIII), wherein the DAR is comprised between 4 and 7 maytansinoid molecules/antibody molecule, said DAR being determined by measuring spectrophotometrically the ratio of the absorbance at 252 nm and 280 nm of a solution of the substantially purified conjugate.

The conjugates obtainable by the above-process are comprised within the scope of this invention. In a particular aspect, such conjugates have a structure chosen between formula (XV) and formula (XVI), wherein Ab is an antibody of the invention, and wherein n is comprised between 4 and 10. In a preferred embodiment, n is comprised between 4 and 7. In another preferred embodiment, said conjugates have the structure of formula (XV).

Conjugates of antibodies with maytansinoid drugs can be evaluated for their ability to suppress proliferation of various unwanted cell lines in vitro. For example, cell lines such as the human epidermoid carcinoma line A-431, the human small cell lung cancer cell line SW2, the human breast tumor line SKBR3 and the Burkitt's lymphoma cell line Namalwa can easily be used for the assessment of cytotoxicity of these compounds. Cells to be evaluated can be exposed to the compounds for 24 hours and the surviving fractions of cells measured in direct assays by known methods. $IC_{50}$ values can then be calculated from the results of the assays.

Tomaymycin Derivatives

The cytotoxic according to the present invention may also be a tomaymycin derivative. Tomaymycin derivatives are pyrrolo[1,4]benzodiazepines (PBDs), a known class of compounds exerting their biological properties by covalently binding to the N2 of guanine in the minor groove of DNA. PBDs include a number of minor groove binders such as anthramycin, neothramycin and DC-81.

Novel tomaymycin derivatives that retain high cytotoxicity and that can be effectively linked to cell binding agents are described in the International Application No. PCT/1B2007/000142, whose content is herein incorporated by reference. The cell binding agent-tomaymycin derivative complexes permit the full measure of the cytotoxic action of the tomaymycin derivatives to be applied in a targeted fashion against unwanted cells only, therefore avoiding side effects due to damage to non-targeted healthy cells.

The cytotoxic agent according to the present invention comprises one or more tomaymycin derivatives, linked to a cell binding agent, such as the 2H11R35R74 antibody, via a linking group. The linking group is part of a chemical moiety that is covalently bound to a tomaymycin derivative through conventional methods. In a preferred embodiment, the chemical moiety can be covalently bound to the tomaymycin derivative via a disulfide bond.

The tomaymycin derivatives useful in the present invention have the formula (XX) shown below:

—N3, a cyano, a halo, a trialkyl or triarylphosphonium, an aminoacid-derived group; Preferably W and W' are the same or different and are OH, OMe, OEt, $NHCONH_2$, SMe;

and when ⎓ represents a double bond, U and U' are absent and W and W' represent H;

R1, R2, R1', R2' are the same or different and independently chosen from Halide or Alkyl optionally substituted by one or more Hal, CN, NRR', $CF_3$, OR, Aryl, Het, $S(O)_qR$, or R1 and R2 and R1' and R2' form together a double bond containing group =B and =B' respectively.

Preferably, R1 and R2 and R1' and R2' form together a double bond containing group =B and =B' respectively.

B and B' are the same or different and independently chosen from Alkenyl being optionally substituted by one or more Hal, CN, NRR', $CF_3$, OR, Aryl, Het, $S(O)_qR$ or B and B' represent an oxygen atom.

Preferably, B=B'.

More preferably, B=B'=$CH_2$ or =CH—$CH_3$,

X, X' are the same or different and independently chosen from one or more —O—, —NR—, —(C=O)—, —$S(O)_q$—.

Preferably, X=X'.

More preferably, X=X'=O.

A, A' are the same or different and independently chosen from Alkyl or Alkenyl optionally containing an oxygen, (XX)

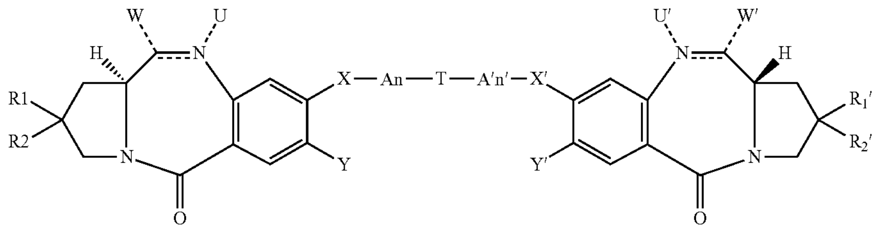

wherein

---- represents an optional single bond;

⎓ represents either a single bond or a double bond;

provided that when ⎓ represents a single bond, U and U', the same or different, independently represent H, and W and W', the same or different, are independently selected from the group consisting of OH, an ether such as —OR, an ester (e.g. an acetate), such as —OCOR, a carbonate such as —OCOOR, a carbamate such as —OCONRR', a cyclic carbamate, such that N10 and C11 are a part of the cycle, a urea such as —NRCONRR', a thiocarbamate such as —OCSNHR, a cyclic thiocarbamate such that N10 and C11 are a part of the cycle, —SH, a sulfide such as —SR, a sulfoxide such as —SOR, a sulfone such as —SOOR, a sulfonate such as —SO3-, a sulfonamide such as —NRSOOR, an amine such as —NRR', optionally cyclic amine such that N10 and C11 are a part of the cycle, a hydroxylamine derivative such as —NROR', an amide such as —NRCOR, an azido such as a nitrogen or a sulfur atom, each being optionally substituted by one or more Hal, CN, NRR', $CF_3$, OR, $S(O)_q$ R, Aryl, Het, Alkyl, Alkenyl.

Preferably, A=A'.

More preferably, A=A'=linear unsubstituted alkyl.

Y, Y' are the same or different and independently chosen from H, OR;

Preferably, Y=Y'.

More preferably, Y=Y'=OAlkyl, more preferably OMethyl.

T is —NR—, —O—, —$S(O)_q$—, or a 4 to 10-membered aryl, cycloalkyl, heterocyclic or heteroaryl, each being optionally substituted by one or more Hal, CN, NRR', $CF_3$, R, OR, $S(O)_qR$, and/or linker(s), or a branched Alkyl, optionally substituted by one or more Hal, CN, NRR', $CF_3$, OR, $S(O)_qR$ and/or linker(s), or a linear Alkyl substituted by one or more Hal, CN, NRR', $CF_3$, OR, $S(O)_qR$ and/or linker(s).

Preferably, T is a 4 to 10-membered aryl or heteroaryl, more preferably phenyl or pyridyl, optionally substituted by one or more linker(s).

Said linker comprises a linking group. Suitable linking groups are well known in the art and include thiol, sulfide, disulfide groups, thioether groups, acid labile groups, photo-labile groups, peptidase labile groups and esterase labile groups. Preferred are disulfide groups and thioether groups.

When the linking group is a thiol-, sulfide (or so-called thioether —S—) or disulfide (—S—S—)-containing group, the side chain carrying the thiol, the sulfide or disulfide group can be linear or branched, aromatic or heterocyclic. One of ordinary skill in the art can readily identify suitable side chains.

Preferably, said linker is of formula:

G-D-(Z)*p*-S—Z' where

G is a single or double bond, —O—, —S— or —NR—;

D is a single bond or -E-, -E-NR—, -E-NR—F—, -E-O—, -E-O—F—, -E-NR—CO—, -E-NR—CO—F—, -E-CO—, —CO-E-, -E-CO—F, -E-S—, -E-S—F—, -E-NR—C—S—, -E-NR—CS—F—;

where E and F are the same or different and are independently chosen from linear or branched —(OCH2CH2)iAlkyl(OCH2CH2)j-, -Alkyl(OCH2CH2)i-Alkyl-, —(OCH2CH2)i-, —(OCH2CH2)iCycloalkyl(OCH2CH2)j—, —(OCH2CH2)iHeterocyclic(OCH2CH2)j-, —(OCH2CH2)iAryl(OCH2CH2)j-, —(OCH2CH2)iHeteroaryl(OCH2CH2)j-, -Alkyl-(OCH2CH2)iAlkyl(OCH2CH2)j-, -Alkyl-(OCH2CH2)i-, -Alkyl-(OCH2CH2)iCycloalkyl(OCH2CH2)j-, -Alkyl(OCH2CH2)iHeterocyclic(OCH2CH2)j-, -Alkyl-(OCH2CH2)iAryl(OCH2CH2)j-, -Alkyl(OCH2CH2)iHeteroaryl(OCH2CH2)j-, -Cycloalkyl-Alkyl-, -Alkyl-Cycloalkyl-, -Heterocyclic-Alkyl-, -Alkyl-Heterocyclic-, -Alkyl-Aryl-, -Aryl-Alkyl-, -Alkyl-Heteroaryl-, -Heteroaryl-Alkyl-;

where i and j, identical or different are integers and independently chosen from 0, 1 to 2000;

Z is linear or branched -Alkyl-;

p is 0 or 1;

Z' represents H, a thiol protecting group such as COR, R20 or SR20, wherein R20 represents H, methyl, Alkyl, optionally substituted Cycloalkyl, aryl, heteroaryl or heterocyclic, provided that when Z' is H, said compound is in equilibrium with the corresponding compound formed by intramolecular cyclisation resulting from addition of the thiol group —SH on the imine bond —NH= of one of the PBD moieties.

n, n', equal or different are 0 or 1.

q is 0, 1 or 2.

R, R' are equal or different and independently chosen from H, Alkyl, Aryl, each being optionally substituted by Hal, CN, NRR', CF3, R, OR, S(O)qR, Aryl, Het;

or their pharmaceutically acceptable salts, hydrates, or hydrated salts, or the polymorphic crystalline structures of these compounds or their optical isomers, racemates, diastereomers or enantiomers.

The compounds of the general formula (XX) having geometrical and stereoisomers are also a part of the invention.

The N-10, C-11 double bond of tomaymycin derivatives of formula (XX) is known to be readily convertible in a reversible manner to corresponding imine adducts in the presence of water, an alcohol, a thiol, a primary or secondary amine, urea and other nucleophiles. This process is reversible and can easily regenerate the corresponding tomaymycin derivatives in the presence of a dehydrating agent, in a non-protic organic solvent, in vacuum or at high temperatures (Z. Tozuka, 1983, *J. Antibiotics,* 36: 276).

Thus, reversible derivatives of tomaymycin derivatives of general formula (XXI) can also be used in the present invention:

(XXI)

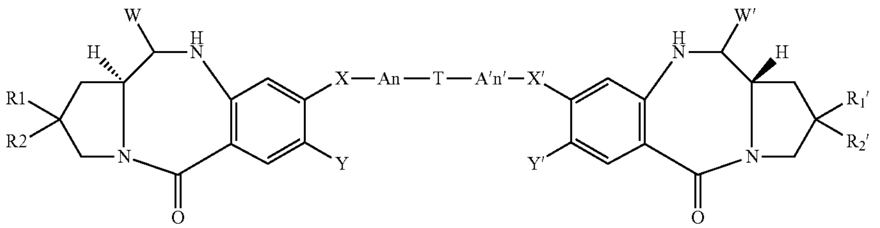

where A, X, Y, n, T, A', X', Y', n', R1, R2, R1, R2' are defined as in formula (XX) and W, W' are the same or different and are selected from the group consisting of OH, an ether such as —OR, an ester (e.g. an acetate), such as —OCOR, —COOR, a carbonate such as —OCOOR, a carbamate such as —OCONRR', a cyclic carbamate, such that N10 and C11 are a part of the cycle, a urea such as —NRCONRR', a thiocarbamate such as —OCSNHR, a cyclic thiocarbamate such that N10 and C11 are a part of the cycle, —SH, a sulfide such as —SR, a sulphoxide such as —SOR, a sulfone such as —SOOR, a sulphonate such as —SO3-, a sulfonamide such as —NRSOOR, an amine such as —NRR', optionally cyclic amine such that N10 and C11 are a part of the cycle, a hydroxylamine derivative such as —NROR', an amide such as —NRCOR, —NRCONRR', an azido such as —N3, a cyano, a halo, a trialkyl or triarylphosphonium, an aminoacid-derived group. Preferably, W and W' are the same or different and are OH, Ome, Oet, NHCONH2, SMe.

Compounds of formula (XXI) may thus be considered as solvates, including water when the solvent is water; these solvates can be particularly useful.

Preferred compounds are those of formula (XXII) or (XXIII):

(XXII)

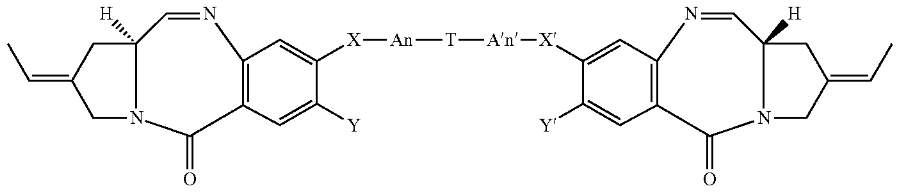

(XXIII)

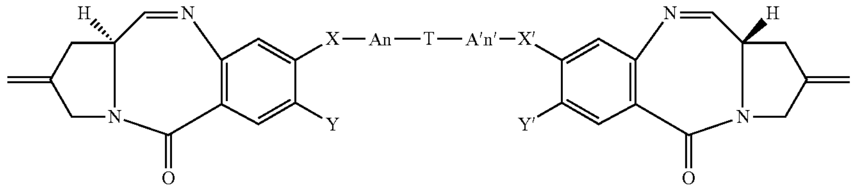

where X, X', A, A', Y, Y', T, n, n' are defined as above.

The compounds of formula (XX) may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art. In particular, such methods can be found in R. C. Larock, *Comprehensive Organic Transformations*, Wiley-VCH Publishers, 1999.

Methods for synthesizing the tomaymycin derivatives which may be used in the invention are described in the International Application No. PCT/1B2007/000142. Compounds of the present invention may be prepared by a variety of synthetic routes. The reagents and starting materials are commercially available, or readily synthesized by well-known techniques by one of ordinary skill in the arts (see, for example, WO 00/12508, WO 00/12507, WO 2005/040170, WO 2005/085260, FR1516743, M. Mori et al., 1986, *Tetrahedron,* 42: 3793-3806).

The conjugate molecules of the invention may be formed using any techniques. The tomaymycin derivatives of the invention may be linked to an antibody or other cell binding agent via an acid labile linker, or by a photolabile linker. The derivatives can be condensed with a peptide having a suitable sequence and subsequently linked to a cell binding agent to produce a peptidase labile linker. The conjugates can be prepared to contain a primary hydroxyl group, which can be acylated and then linked to a cell binding agent to produce a conjugate that can be cleaved by intracellular esterases to liberate free derivative. Preferably, the derivatives are synthesized to contain a free or protected thiol group, and then one or more disulfide or thiol-containing derivatives are each covalently linked to the cell binding agent via a disulfide bond or a thioether link.

Numerous methods of conjugation are taught in U.S. Pat. No. 5,416,064 and U.S. Pat. No. 5,475,092. The tomaymycin derivatives can be modified to yield a free amino group and then linked to an antibody or other cell binding agent via an acid labile linker or a photolabile linker. The tomaymycin derivatives with a free amino or carboxyl group can be condensed with a peptide and subsequently linked to a cell binding agent to produce a peptidase labile linker. The tomaymycin derivatives with a free hydroxyl group on the linker can be acylated and then linked to a cell binding agent to produce a conjugate that can be cleaved by intracellular esterases to liberate free drug. Most preferably, the tomaymycin derivatives are treated to create a free or protected thiol group, and then the disulfide- or thiol containing tomaymycin dimers are linked to the cell binding agent via disulfide bonds.

Preferably, monoclonal antibody- or cell binding agent-tomaymycin derivative conjugates are those that are joined via a disulfide bond, as discussed above, that are capable of delivering tomaymycin derivatives. Such cell binding conjugates are prepared by known methods such as by modifying monoclonal antibodies with succinimidyl pyridyl-dithiopropionate (SPDP) (Carlsson et al., 1978, *Biochem. J.,* 173: 723-737). The resulting thiopyridyl group is then displaced by treatment with thiol-containing tomaymycin derivatives to produce disulfide linked conjugates. Alternatively, in the case of the aryldithio-tomaymycin derivatives, the formation of the cell binding conjugate is effected by direct displacement of the aryl-thiol of the tomaymycin derivative by sulfhydryl groups previously introduced into antibody molecules. Conjugates containing 1 to 10 tomaymycin derivative drugs linked via a disulfide bridge are readily prepared by either method.

More specifically, a solution of the dithio-nitropyridyl modified antibody at a concentration of 2.5 mg/ml in 0.05 M potassium phosphate buffer, at pH 7.5 containing 2 mM EDTA is treated with the thiol-containing tomaymycin derivative (1.3 molar eq./dithiopyridyl group). The release of nitropyridinethione from the modified antibody is monitored spectrophotometrically at 325 nm and is complete in about 16 hours. The antibody-tomaymycin derivative conjugate is purified and freed of unreacted drug and other low molecular weight material by gel filtration through a column of Sephadex G-25 or Sephacryl S300. The number of tomaymycin derivative moieties bound per antibody molecule can be determined by measuring the ratio of the absorbance at 230 nm and 275 nm. An average of 1-10 tomaymycin derivative molecules/antibody molecule can be linked via disulfide bonds by this method.

The effect of conjugation on binding affinity towards the antigen-expressing cells can be determined using the methods previously described by Liu et al., 1996, *Proc. Natl. Acad. Sci. U.S.A.,* 93: 8618-8623. Cytotoxicity of the tomaymycin derivatives and their antibody conjugates to cell lines can be measured by back-extrapolation of cell proliferation curves as described in Goldmacher et al., 1985, *J. Immunol.,* 135: 3648-3651. Cytotoxicity of these compounds to adherent cell lines can be determined by clonogenic assays as described in Goldmacher et al., 1986, *J. Cell Biol.,* 102: 1312-1319.

CC-1065 Analogues

The cytotoxic agent used in the cytotoxic conjugates according to the present invention may also be CC-1065 or a derivative thereof.

CC-1065 is a potent anti-tumor antibiotic isolated from the culture broth of *Streptomyces zelensis*. CC-1065 is about 1000-fold more potent in vitro than are commonly used anti-cancer drugs, such as doxorubicin, methotrexate and vincristine (B. K. Bhuyan et al., 1982, *Cancer Res.,* 42, 3532-3537). CC-1065 and its analogs are disclosed in U.S. Pat. Nos. 6,372,738, 6,340,701, 5,846,545 and 5,585,499.

The cytotoxic potency of CC-1065 has been correlated with its alkylating activity and its DNA-binding or DNA-intercalating activity. These two activities reside in separate parts of the molecule. Thus, the alkylating activity is contained in the cyclopropapyrroloindole (CPI) subunit and the DNA-binding activity resides in the two pyrroloindole subunits.

Although CC-1065 has certain attractive features as a cytotoxic agent, it has limitations in therapeutic use. Administration of CC-1065 to mice caused a delayed hepatotoxicity leading to mortality on day 50 after a single intravenous dose of 12.5 μg/kg (V. L. Reynolds et al., 1986, *J. Antibiotics, XXIX:* 319-334). This has spurred efforts to develop analogs that do not cause delayed toxicity, and the synthesis of simpler analogs modeled on CC-1065 has been described (M. A. Warpehoski et al., 1988, *J. Med. Chem.,* 31: 590-603).

In another series of analogs, the CPI moiety was replaced by a cyclopropa[c]benz[e]indole (CBI) moiety (D. L. Boger et al., 1990, *J. Org. Chem.,* 55: 5823-5833; D. L. Boger et al., 1991, *BioOrg. Med. Chem. Lett.,* 1: 115-120). These compounds maintain the high in vitro potency of the parental drug, without causing delayed toxicity in mice. Like CC-1065, these compounds are alkylating agents that bind to the minor groove of DNA in a covalent manner to cause cell death. However, clinical evaluation of the most promising analogs, Adozelesin and Carzelesin, has led to disappointing results (B. F. Foster et al., 1996, *Investigational New Drugs,* 13: 321-326; I. Wolff et al., 1996, *Clin. Cancer Res.,* 2: 1717-1723). These drugs display poor therapeutic effects because of their high systemic toxicity.

The therapeutic efficacy of CC-1065 analogs can be greatly improved by changing the in vivo distribution through targeted delivery to the tumor site, resulting in lower toxicity to non-targeted tissues, and thus, lower systemic toxicity. In order to achieve this goal, conjugates of analogs and derivatives of CC-1065 with cell-binding agents that specifically target tumor cells have been described (U.S. Pat. Nos. 5,475,092; 5,585,499; 5,846,545). These conjugates typically display high target-specific cytotoxicity in vitro, and exceptional anti-tumor activity in human tumor xenograft models in mice (R. V. J. Chari et al., 1995, *Cancer Res.,* 55: 4079-4084).

Recently, prodrugs of CC-1065 analogs with enhanced solubility in aqueous medium have been described (European Patent Application No. 06290379.4). In these prodrugs, the phenolic group of the alkylating portion of the molecule is protected with a functionality that renders the drug stable upon storage in acidic aqueous solution, and confers increased water solubility to the drug compared to an unprotected analog. The protecting group is readily cleaved in vivo at physiological pH to give the corresponding active drug. In the prodrugs described in EP 06290379.4, the phenolic substituent is protected as a sulfonic acid containing phenyl carbamate which possesses a charge at physiological pH, and thus has enhanced water solubility. In order to further enhance water solubility, an optional polyethylene glycol spacer can be introduced into the linker between the indolyl subunit and the cleavable linkage such as a disulfide group. The introduction of this spacer does not alter the potency of the drug.

Methods for synthesizing CC-1065 analogs that may be used in the cytotoxic conjugates of the present invention, along with methods for conjugating the analogs to cell binding agents such as antibodies, are described in detail in EP 06290379.4 (whose content is incorporated herein by reference) and U.S. Pat. Nos. 5,475,092, 5,846,545, 5,585,499, 6,534,660 and 6,586,618 and in U.S. application Ser. Nos. 10/116,053 and 10/265,452.

Other Drugs

Drugs such as methotrexate, daunorubicin, doxorubicin, vincristine, vinblastine, melphalan, leptomycin derivatives, mitomycin C, chlorambucil, calicheamicin, tubulysin and tubulysin analogs, duocarmycin and duocarmycin analogs, dolastatin and dolastatin analogs such as auristatins are also suitable for the preparation of conjugates of the present invention. The drug molecules can also be linked to the antibody molecules through an intermediary carrier molecule such as serum albumin. Doxorubicin and Daunorubicin compounds, as described, for example, in U.S. Pat. No. 6,630,579, may also be useful cytotoxic agents.

Therapeutic Composition

The invention also relates to a therapeutic composition for the treatment of a hyperproliferative disorder in a mammal which comprises a therapeutically effective amount of a compound of the invention and a pharmaceutically acceptable carrier. In one embodiment said pharmaceutical composition is for the treatment of cancer, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma, and other cancers yet to be determined in which EphA2 is expressed predominantly. In a preferred embodiment, the pharmaceutical compositions of the invention are used for treatment of cancer of the lung, breast, colon, prostate, kidney, pancreas, ovary, cervix and lymphatic organs, osteosarcoma, synovial carcinoma, a sarcoma, head and neck, a glioma, gastric, liver or other carcinomas in which EphA2 is expressed. In particular, the cancer is a metastatic cancer. In another embodiment, said pharmaceutical composition relates to other disorders such as, for example, autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as mV infection, HIV infection, AIDS, etc.; and parasite infections, such as giardiasis, amoebiasis, schistosomiasis, and others as determined by one of ordinary skill in the art.

The instant invention provides pharmaceutical compositions comprising:

an effective amount of an antibody, antibody fragment or antibody conjugate of the present invention, and a pharmaceutically acceptable carrier, which may be inert or physiologically active.

As used herein, "pharmaceutically-acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH ~7.4, containing or not containing about 1 mg/ml to 25 mg/ml human serum albumin, (2) 0.9% saline (0.9% w/v sodium chloride (NaCl)), and (3) 5% (w/v) dextrose; and may also contain an antioxidant such as tryptamine and a stabilizing agent such as Tween 20.

The compositions herein may also contain a further therapeutic agent, as necessary for the particular disorder being treated. Preferably, the antibody, antibody fragment or antibody conjugate of the present invention, and the supplementary active compound will have complementary activities, that do not adversely affect each other. In a preferred embodiment, the further therapeutic agent is an antagonist of fibroblast-growth factor (FGF), hepatocyte growth factor (HGF), tissue factor (TF), protein C, protein S, platelet-derived growth factor (PDGF), or HER2 receptor.

The compositions of the invention may be in a variety of forms. These include for example liquid, semi-solid, and solid dosage forms, but the preferred form depends on the intended mode of administration and therapeutic application. Typical preferred compositions are in the form of injectable or infusible solutions. The preferred mode of administration is parenteral (e.g. intravenous, intramuscular, intraperinoneal, subcutaneous). In a preferred embodiment, the compositions of the invention are administered intravenously as a bolus or by continuous infusion over a period of time. In another preferred embodiment, they are injected by intramuscular, subcutaneous, intra-articular, intrasynovial, intratumoral, peritumoral, intralesional, or perilesional routes, to exert local as well as systemic therapeutic effects. They can be also administered by nebulisation.

Sterile compositions for parenteral administration can be prepared by incorporating the antibody, antibody fragment or antibody conjugate of the present invention in the required amount in the appropriate solvent, followed by sterilization by microfiltration. As solvent or vehicle, there may be used water, saline, phosphate buffered saline, dextrose, glycerol, ethanol, and the like, as well as a combination thereof. In many cases, it will be preferable to include isotonic agents, such as sugars, polyalcohols, or sodium chloride in the composition. These compositions may also contain adjuvants, in particular wetting, isotonizing, emulsifying, dispersing and stabilizing agents. Sterile compositions for parenteral administration may also be prepared in the form of sterile solid compositions which may be dissolved at the time of use in sterile water or any other injectable sterile medium.

The doses depend on the desired effect, the duration of the treatment and the route of administration used; they are generally between 5 mg and 1000 mg per day for an adult with unit doses ranging from 1 mg to 250 mg of active substance. In general, the doctor will determine the appropriate dosage depending on the age, weight and any other factors specific to the subject to be treated.

Therapeutic Methods of Use

In another embodiment, the present invention provides a method for inhibiting the EphA2 receptor activity by administering an antibody which antagonizes said EphA2 receptor, to a patient in need thereof. Any of the type of antibodies, antibody fragments, or cytotoxic conjugates of the invention, may be used therapeutically. The invention thus includes the use of antagonistic anti-EphA2 antibodies, fragments thereof, or cytotoxic conjugates thereof as medicaments. In a preferred embodiment, the antagonistic anti-EphA2 antibody is the 2H11R35R74 antibody or a humanized variant thereof.

In a preferred embodiment, antibodies, antibody fragments, or cytotoxic conjugates of the invention are used for the treatment of a hyperproliferative disorder in a mammal. In a more preferred embodiment, one of the pharmaceutical compositions disclosed above, and which contains an antibody, antibody fragment, or cytotoxic conjugate of the invention, is used for the treatment of a hyperproliferative disorder in a mammal. It is also an embodiment of the invention that the antibodies, antibody fragments, and cytotoxic conjugates of the invention can also be used to make a medicament to treat said hyperproliferative disorder in a mammal. In one embodiment, the disorder is a cancer. In particular, the cancer is a metastatic cancer. The antibodies, antibody fragments, and cytotoxic conjugates of the invention can also be used to treat the neovascularization of said cancer tumor.

Accordingly, the pharmaceutical compositions of the invention are useful in the treatment or prevention of a variety of cancers, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma, and other cancers yet to be determined in which EphA is expressed predominantly. In a preferred embodiment, the cancer is a cancer of the lung, breast, colon, prostate, kidney, pancreas, uterus, ovary, cervix and lymphatic organs, osteosarcoma, synovial carcinoma, a sarcoma, head and neck, a glioma, gastric, liver or other carcinomas in which EphA is expressed. In another embodiment, said pharmaceutical composition relates to other disorders such as, for example, autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as mV infection, HIV infection, AIDS, etc.;

and parasite infections, such as giardiasis, amoebiasis, schistosomiasis, and others as determined by one of ordinary skill in the art.

Similarly, the present invention provides a method for inhibiting the growth of selected cell populations comprising contacting target cells, or tissue containing target cells, with an effective amount of an antibody, antibody fragment or antibody conjugate of the present invention, or an antibody, antibody fragment or a therapeutic agent comprising a cytotoxic conjugate, either alone or in combination with other cytotoxic or therapeutic agents.

The method for inhibiting the growth of selected cell populations can be practiced in vitro, in vivo, or ex vivo. As used herein, "inhibiting growth" means slowing the growth of a cell, decreasing cell viability, causing the death of a cell, lysing a cell and inducing cell death, whether over a short or long period of time.

Examples of in vitro uses include treatments of autologous bone marrow prior to their transplant into the same patient in order to kill diseased or malignant cells; treatments of bone marrow prior to its transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogeneic bone marrow or tissue prior to transplant in order to prevent graft versus host disease (GVHD). Treatment can be carried out as follows. Bone marrow is harvested from the patient or other individual and then incubated in medium containing serum to which is added the cytotoxic agent of the invention. Concentrations range from about 10 μM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the antibody, the epitope-binding antibody fragment, or the cytotoxic conjugate of the invention will be supplied as solutions that are tested for sterility and for endotoxin levels. Examples of suitable protocols of cytotoxic conjugate administration are as follows. Conjugates are given weekly for 4 weeks as an i.v. bolus each week. Bolus doses are given in 50 to 100 ml of normal saline to which 5 to 10 ml of human serum albumin can be added. Dosages will be 10 μg to 100 mg per administration, i.v. (range of 100 ng to 1 mg/kg per day). More preferably, dosages will range from 50 μg to 30 mg. Most preferably, dosages will range from 1 mg to 20 mg. After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Diagnostic

The antibodies or antibody fragments of the invention can also be used to detect EphA2 in a biological sample in vitro or in vivo. In one embodiment, the anti-EphA2 antibodies of the invention are used to determine the level of EphA2 in a tissue or in cells derived from the tissue. In a preferred embodiment, the tissue is a diseased tissue. In a preferred embodiment of the method, the tissue is a tumor or a biopsy thereof. In a preferred embodiment of the method, a tissue or a biopsy thereof is first excised from a patient, and the levels of EphA2 in the tissue or biopsy can then be determined in an immunoassay with the antibodies or antibody fragments of the invention. The tissue or biopsy thereof can be frozen or fixed. The same method can be used to determine other properties of the EphA2 protein, such as its level of tyrosine phosphorylation, cell surface levels, or cellular localization.

The above-described method can be used to diagnose a cancer in a subject known to or suspected to have a cancer, wherein the level of EphA2 measured in said patient is compared with that of a normal reference subject or standard. Said method can then be used to determine whether a tumor expresses EphA2, which may suggest that the tumor will respond well to treatment with the antibodies, antibody fragments or antibody conjugates of the present invention. Preferably, the tumor is a cancer of the lung, breast, colon, prostate, kidney, pancreas, uterus, ovary, cervix and lymphatic organs, osteosarcoma, synovial carcinoma, a sarcoma, a glioma, gastric, liver, head and neck or other carcinomas in which EphA2 is expressed, and other cancers yet to be determined in which EphA2 is expressed predominantly.

The present invention further provides for monoclonal antibodies, humanized antibodies and epitope-binding fragments thereof that are further labeled for use in research or diagnostic applications. In preferred embodiments, the label is a radiolabel, a fluorophore, a chromophore, an imaging agent or a metal ion.

A method for diagnosis is also provided in which said labeled antibodies or epitope-binding fragments thereof are administered to a subject suspected of having a cancer, and the distribution of the label within the body of the subject is measured or monitored.

Kit

The present invention also includes kits, e.g., comprising a described cytotoxic conjugate and instructions for the use of the cytotoxic conjugate for killing of particular cell types. The instructions may include directions for using the cytotoxic conjugates in vitro, in vivo or ex vivo.

Typically, the kit will have a compartment containing the cytotoxic conjugate. The cytotoxic conjugate may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the cytotoxic conjugate prior to administering to a patient, and tools that aid in administering the conjugate to a patient.

The present invention also relates to an article of manufacture comprising:

a) a packaging material b) an antibody or epitope-binding fragment thereof or a conjugate, and c) a label or package insert contained within said packaging material indicting that said antibody or epitope-binding fragment thereof is effective for treating cancer.

EXAMPLES
Example 1
Preparation of Conjugates
Conjugation of 2H11R35R74 to DM4
General Synthetic Schemes
Example 1a
hu2H11R35R74-PEG4-NHAc-DM4
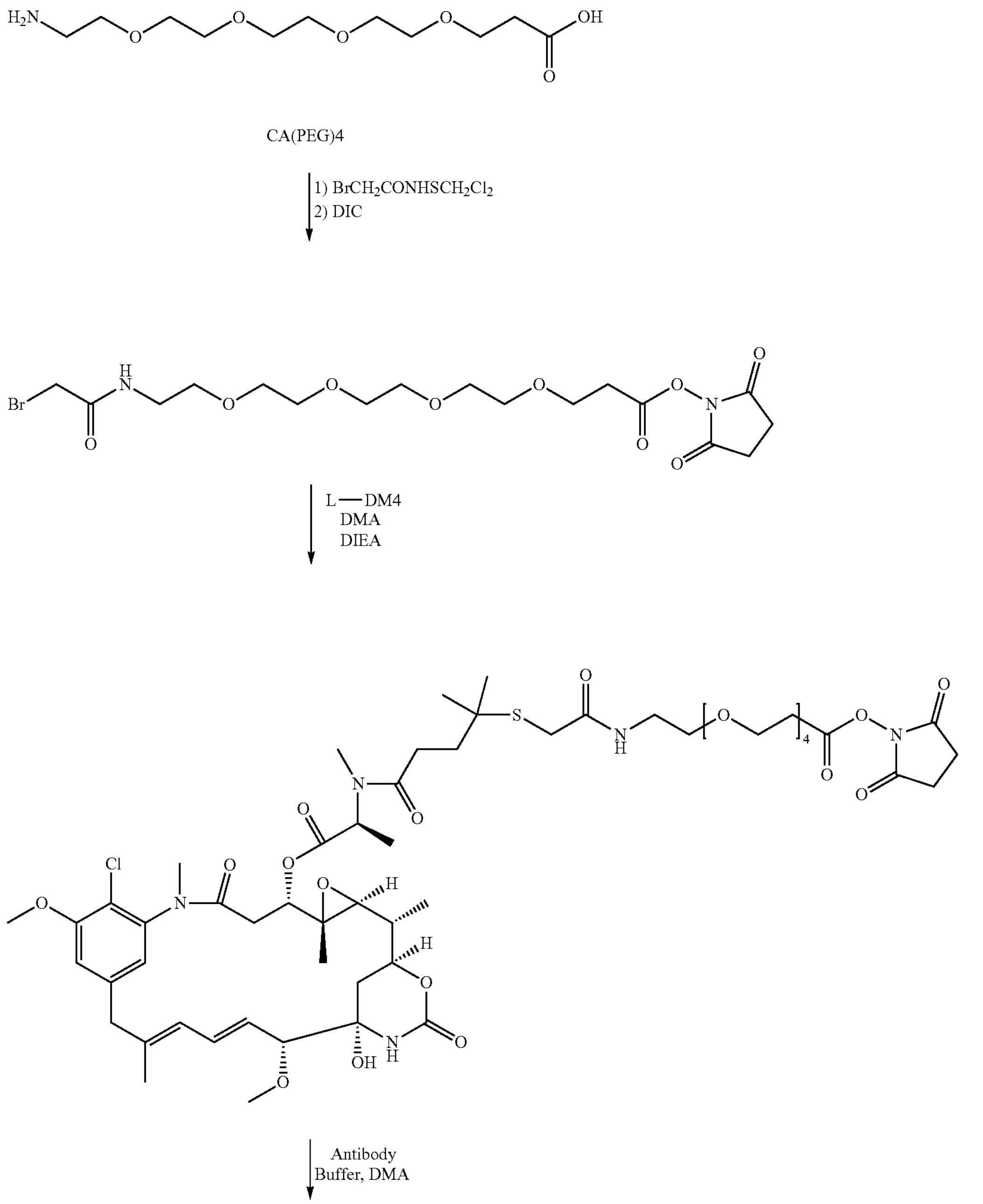

-continued
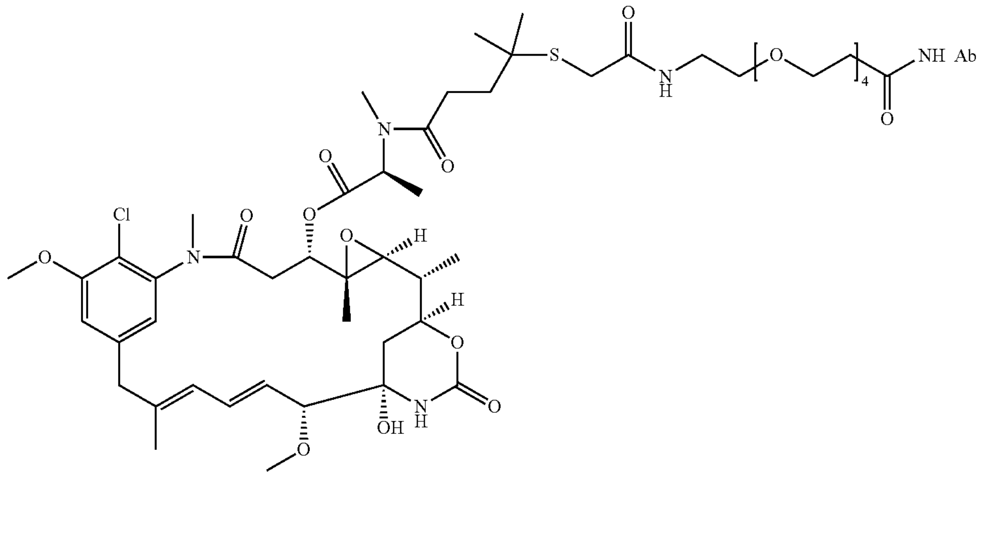
Example 1b
hu2H11R35R74-PEG4-Mal-DM4
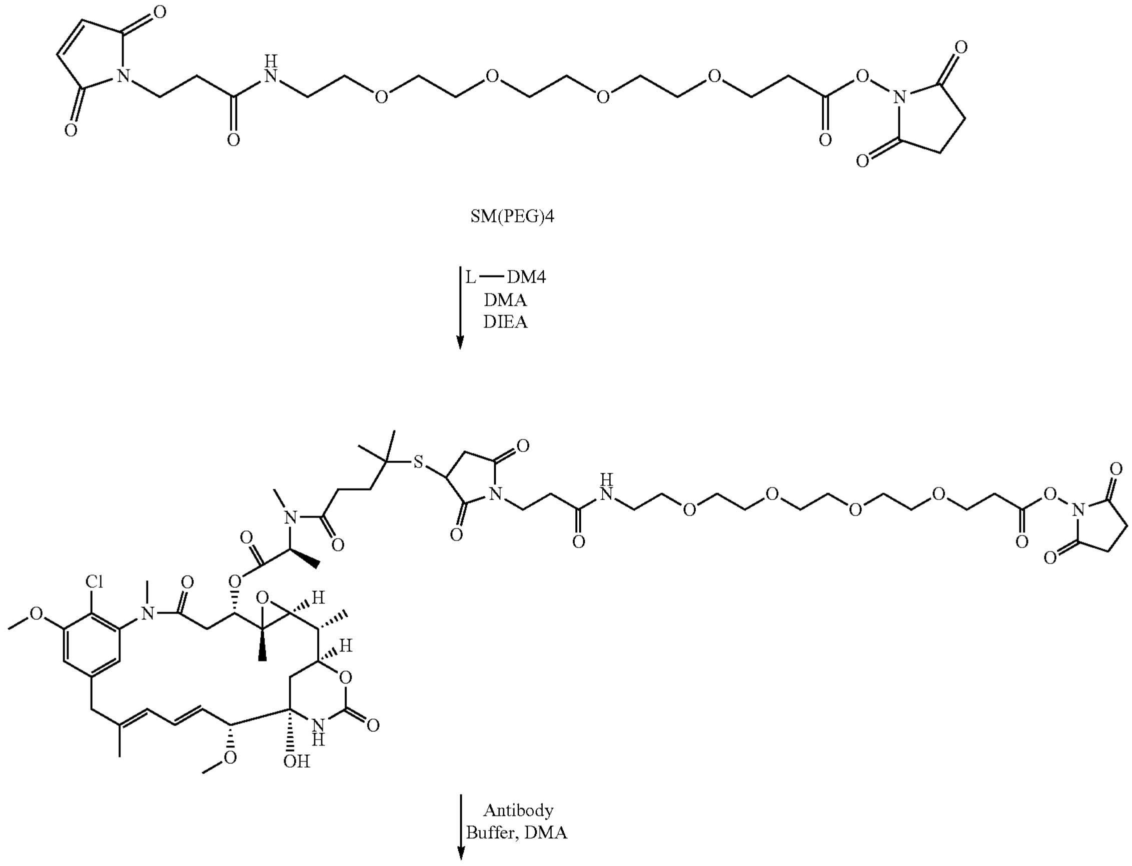

-continued

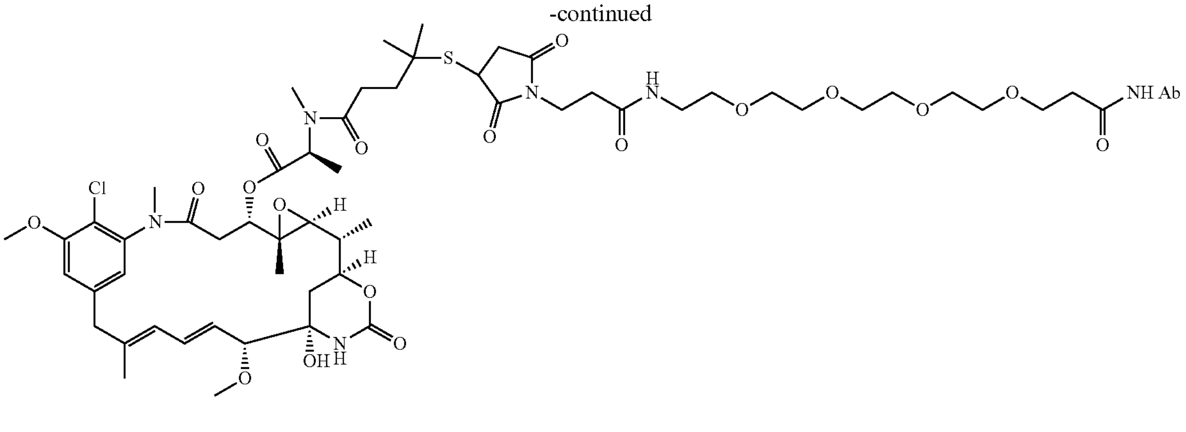

Method A: High Pressure Liquid Chromatography—Mass Spectrometry (LCMS)

Spectra have been obtained on a Waters UPLC-SQD system in positive and/or negative electrospray mode (ES+/−). Chromatographic conditions are the following: column: ACQUITY BEH C18, 1.7 μm-2.1×30 mm; solvents: A: $H_2O$ (0.1% formic acid) B: $CH_3CN$ (0.1% formic acid); column temperature: 45° C.; flow rate: 0.6 ml/min; gradient (2 min): from 5 to 50% of B in 1 min; 1.3 min: 100% of B; 1.45 min: 100% of B; 1.75 min: 5% of B.

Method B: High Pressure Liquid Chromatography—Mass Spectrometry (LCMS)

Spectra have been obtained on a Waters ZQ system in positive and/or negative electrospray mode (ES+/−). Chromatographic conditions are the following: column: XBridge C18 2.5 μm 3×50 mm; solvents: A: $H_2O$ (0.1% formic acid) B: $CH_3CN$ (0.1% formic acid; column temperature: 70° C.; flow rate: 0.9 ml/min; gradient (7 min): from 5 to 100% of B in 5.3 min; 5.5 min: 100% of B; 6.3 min: 5% of B.

Method C: Deglycosylation and High Resolution Mass Spectrometry of Immunoconjugate (HRMS)

Deglycosylation is a technique of enzymatic digestion by means of glycosidase. The deglycosylation is made from 500 μl of conjugated+100 μl of Tris buffer HCl 50 mM+10 μl of glycanase-F enzyme (100 units of freeze-dried enzyme/100 μl of water). The medium is vortexed and maintained one night at 37° C. The deglycosylated sample is then ready to be analyzed in HRMS. Mass spectra were obtained on a Waters Q-Tof-2 system in electrospray positive mode (ES+). Chromatographic conditions are the following: column: 4 μm BioSuite 250 URH SEC 4.6×300 mm (Waters); solvents: A: ammonium formate 25 mM+1% formic acid: B: $CH_3CN$; column temperature: 30° C.; flow rate 0.4 ml/min; isocratic elution 70% A+30% B (15 min).

Method D: Analytical Size Exclusion Chromatography (SEC)

- Column: TSKgel G3000 SWXL 5 μm column, 7.8 mm×30 cm, TOSOH BIOSCIENCE, LLC Part #: 08541
- Mobile Phase: KCl (0.2M), $KH_2PO_4$ (0.052M) $K_2HPO_4$ (0.107M), iPrOH (20% in volume)
- Analysis Conditions: isocratic elution at 0.5 ml/min for 30 minutes Method E: Mass Spectrometry (MS)

Spectra have been obtained through chemical ionisation (reactant gas: ammoniac) on a WATERS GCT of system (direct introduction without LC).

Method F: High Pressure Liquid Chromatography—Mass Spectrometry (LCMS)

Spectra have been obtained on a Waters HPLC-SQD system in positive and/or negative electrospray mode (ES+/−). Chromatographic conditions are the following: column: ACQUITY BEH C18 1.7 μm-2.1×50 mm; solvents: A: $H_2O$ (0.1% formic acid) B: $CH_3CN$ (0.1% formic acid); column temperature: 50° C.; flow rate: 1 ml/min; gradient (2 min): from 5 to 50% of B in 0.8 min; 1.2 min: 100% of B; 1.85 min: 100% of B; 1.95:5% of B.

Abbreviations:

AcOEt: ethyl acetate; ALK: $(C_1-C_{12})$alkylene group, particularly $(C_1-C_6)$alkylene; DAR: Drug Antibody Ratio; DBU: 1,8-diazabicyclo[5.4.0]undec-7-ene; DCC: N,N'-dicyclohexylcarbodiimide; DCM: dichloromethane; DEAD: diethylazodicarboxylate; DIC: N,N'-diisopropylcarbodiimide; DIPEA: N,N-diisopropylethylamine; DMA: dimethylacetamide; DMAP: 4-dimethylaminopyridine; DME: dimethoxyethane; DMF: dimethylformamide; DMSO: dimethylsulfoxyde; ϵ: molar extinction coefficient; EEDQ: 2-ethoxy-1-ethoxycarbonyl-1,2-dihydroquinoline; EDCI: N-(3-dimethylaminopropyl)-N'-ethylcarbodiimide; EDTA: ethylene-diamine-tetraacetic acid; Fmoc: fluorenylmethoxycarbonyl; Hal: halogen atom; HOBt: 1-hydroxybenzotriazole; HEPES: 4-(2-hydroxyethyl)-1-piperazine-ethanesulfonic acid; NHS: N-hydroxysuccinimide; iPrOH: isopropyl alcohol; NMP: N-methylpyrrolidinone; Rf: retention factor; RP: reduced pressure; RT: room temperature; SEC: Size Exclusion Chromatography; TBDMS: tert-butyldimethylsilyl; TEA: triethylamine; TFA: trifluoroacetic acid; TFAA: trifluoroacetic anhydride; TFF: Tangential Flow Filtration; THF: tetrahydrofurane; TIPS: triisopropylsilyl; TLC: Thin Layer Chromatography; $t_R$: retention time.

Buffers Contents:

- Buffer A (pH 6.5): NaCl (50 mM), KPi (50 mM), EDTA (2 mM)
- Buffer HGS (pH 5.5): Histidine (10 mM), Glycine (130 mM), sucrose 5% (w/v), HCl (8 mM)

Parameters for Ab and L-DM4 concentration calculations (reference for the method of calculation: Therapeutic Antibodies and Protocols, vol 525, 445):

- Molar extinction coefficients for hu2H11R35R74 (224000 at 280 nM; 82880 at 252 nM) and L-DM4 (5180 at 280 nM; 26159 at 252 nM), assuming an average 160000 molecular weight for the antibody.

Example 1a 1a.1. Preparation of Conjugate Linked with PEG4-Acetamido hu2H11R35R74-PEG4-NHAc-DM4

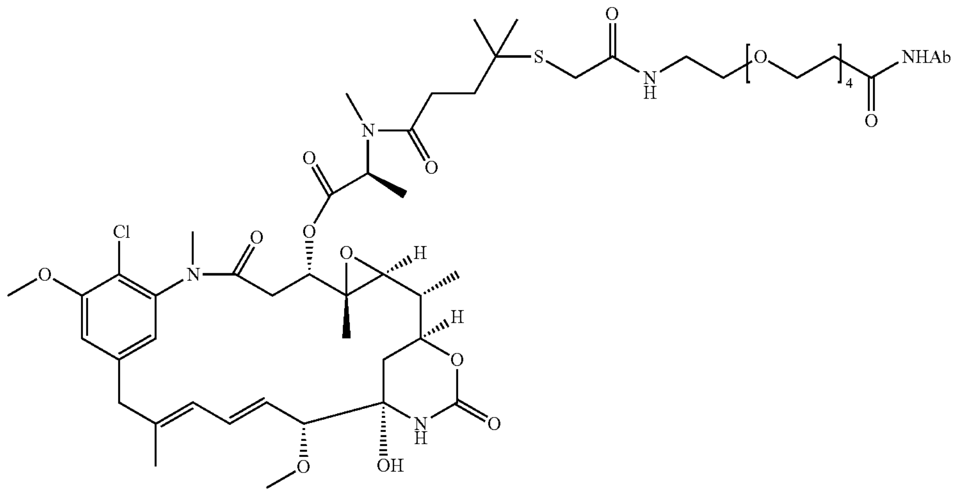

Under magnetic stirring, at room temperature, 9 ml of hu2H11R35R74 (14.36 mg/ml in buffer A) are added, then 16.85 ml of buffer A, 3.23 ml of HEPES 1M, 1.59 ml of DMA, followed by 1.64 ml of a 10 mM DMA solution of L-DM4-AcNH-PEG4-CONHS activated ester. After 1 hours 30 minutes at room temperature, an extra 0.085 ml of 10 mM DMA solution of L-DM4-AcNH-PEG4-CONHS activated ester is added. After 1 hours 45 minutes at room temperature, the crude conjugation medium is diluted with 60 ml of HGS buffer and purified by TFF on Pellicon 3 cassettes. The sample is diafiltered against ~10 sample volumes of HGS buffer and then collected. The TFF tank and lines are washed with an extra 10 ml of HGS buffer. The two solutions are mixed, filter-sterilized through 0.22 μm PVDF, concentrated on Amicon 15 and filter-sterilized through 0.22 μm PVDF. 17 ml of hu2H11R35R74-PEG4-NHAc-DM4 immunoconjugate (c=5.76 mg/ml) was thus obtained. The immunoconjugate is then analyzed for final drug load and monomeric purity.

SEC analysis (method D): DAR (SEC)=5.4; RT=16.757; monomeric purity=99.5%

HRMS data (method C): see FIG. 2

1a.2. Preparation of L-DM4-AcNH-PEG4-CONHS Activated Ester

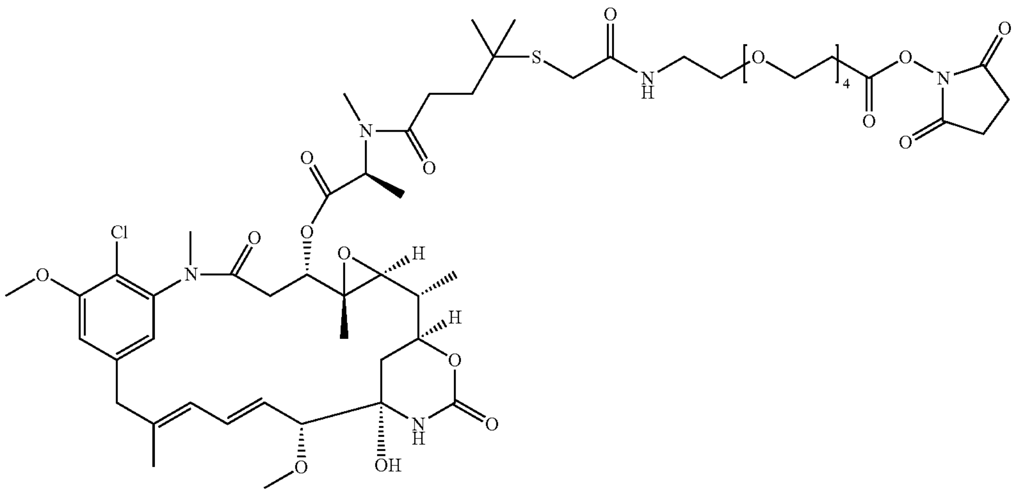

Under magnetic stirring, at room temperature, 154.3 mg of L-DM4 are introduced in a glass vial. A solution of 90 mg of 3-[2-(2-{2-[2-(2-bromo-acetylamino)-ethoxy]-ethoxy}-ethoxy)-ethoxy]-propionic acid 2,5-dioxo-pyrrolidin-1-yl ester in 0.94 ml of DMA is then added, followed by 36 μl of DIEA. After 23 hours at room temperature, the reaction medium is diluted with 5 ml of AcOEt and washed with 7 ml of water. The aqueous phase is extracted with 5 ml of AcOEt. The combined organic phases are dried over magnesium sulphate, concentrated to dryness under reduced pressure. 228 mg of pale yellow viscous oil are obtained, which product is diluted with a minimum amount of DMA and purified by flash-chromatography on 30 g of C18-grafted silica gel (gradient of elution water:acetonitrile 95:5 to 5:95 by volume). After concentration of fractions 2 and 3 under reduce pressure, a colourless viscous oil is obtained, which product is diluted with a minimum amount of DMA and purified by flash-chromatography on 30 g of C18-grafted silica gel (gradient of elution water:acetonitrile 95:5 to 5:95 by volume). After concentration of fractions 33 to 35 under reduce pressure, 41 mg of L-DM4-AcNH-PEG4-CONHS activated ester are obtained in the form of a white meringue-like product, the characteristics of which are as follows:

Mass Spectra: Method B

Retention time (min)=4.06

[M+H−H2O]+: m/z 1164; [M+H]+: m/z 1182;

[M−H+HCO2H]−: m/z 1226

NMR analysis 1H (500 MHz, δ in ppm, chloroform-d): 0.80 (s, 3H); 1.21 (s, 3H); 1.22 (s, 3H); 1.25 (m, 1H); 1.29 (d, J=6.7 Hz, 6H); 1.46 (m, 1H); 1.57 (d, J=13.4 Hz, 1H); 1.64 (s, 3H); 1.76 to 1.83 (m, 1H); 1.88 to 1.96 (m, 1H); 2.18 (dd, J=2.5 et 14.3 Hz, 1H); 2.36 (m, 1H); 2.53 (m, 1H); 2.61 (dd, J=12.5 et 14.3 Hz, 1H); 2.82 to 2.92 (m, 10H); 2.98 (d, J=16.7 Hz, 1H); 3.03 (d, J=9.6 Hz, 1H); 3.15 (d, J=12.9 Hz, 1H); 3.22 (s, 3H); 3.32 (s large, 1H); 3.36 (s, 3H); 3.42 (m, 2H); 3.50 (d, J=9.1 Hz, 1H); 3.53 (t, J=5.2 Hz, 2H); 3.58 to 3.67 (m, 13H); 3.84 (t, J=6.4 Hz, 2H); 3.99 (s, 3H); 4.27 (m, 1H); 4.77 (dd, J=2.9 et 11.9 Hz, 1H); 5.42 (q, J=6.7 Hz, 1H); 5.66 (dd, J=9.1 et 15.4 Hz, 1H); 6.23 (s, 1H); 6.43 (dd, J=11.3 et 15.4 Hz, 1H); 6.64 (d, J=1.1 Hz, 1H); 6.74 (d, J=11.3 Hz, 1H); 6.85 (d, J=1.1 Hz, 1H); 7.08 (t, J=5.2 Hz, 1H).

1a.3. Preparation of 3-[2-(2-{2-[2-(2-bromo-acetylamino)-ethoxy]-ethoxy}-ethoxy)-ethoxy]-propionic acid 2,5-dioxo-pyrrolidin-1-yl ester

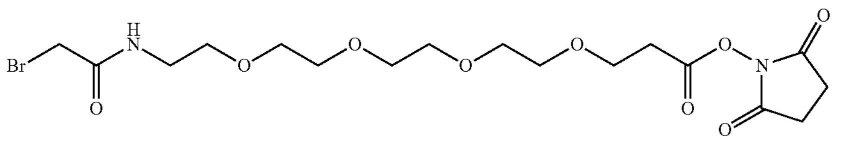 [SMILES: O=C(CBr)NCCOCCOCCOCCOCCC(=O)ON1C(=O)CCC1=O]

Under magnetic stirring, at room temperature, 671.4 mg of 3-(2-{2-[2-(2-amino-ethoxy)-ethoxy]-ethoxy}-ethoxy)-propionic acid (CA(PEG)4, Pierce) are introduced in a glass vial. A solution of 597.4 mg of bromo-acetic acid 2,5-dioxo-pyrrolidin-1-yl ester in 14 ml of dichloromethane is then added. After 15 minutes at room temperature, 0.396 ml of DIC (N,N'-diisopropylcarbodiimide) is added. After 1 hour 30 minutes, the crude reaction medium is filtered on sintered glass, and the filtrate is purified by flash-chromatography on 100 g of CN-grafted silica gel (gradient of elution n.heptane/iPrOH/AcOEt with increasing iPrOH portion). After concentration of fractions 30 to 45 under reduce pressure, 761 mg of 3-[2-(2-{2-[2-(2-bromo-acetylamino)-ethoxy]-ethoxy}-ethoxy)-ethoxy]-propionic acid 2,5-dioxo-pyrrolidin-1-yl ester are obtained in the form of a colourless oil, the characteristics of which are as follows:

Mass Spectra: Method A

Retention time (min)=0.74

[M+H]+: m/z 483/485

[M−H+HCO2H]−: m/z 527/529

Bromo-acetic acid 2,5-dioxo-pyrrolidin-1-yl ester could be prepared following published protocol (Biochemistry, 1974, 481).

Example 1b 1b.1. Preparation of Conjugate Linked with PEG4-Mal hu2H11R35R74-PEG4-Mal-DM4

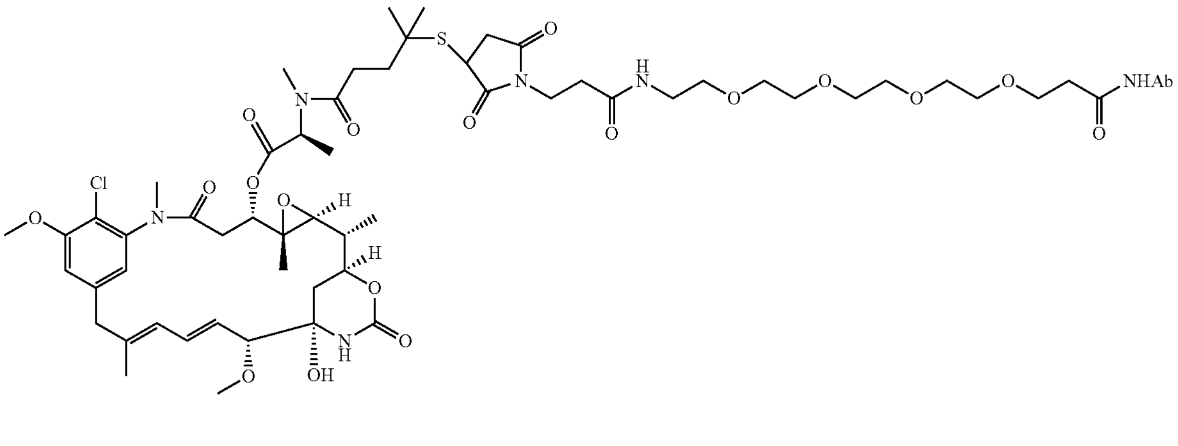

Under magnetic stirring, at room temperature, 4 ml of hu2H11R35R74 (14.36 mg/ml in buffer A) are added, then 7.5 ml of buffer A, 1.45 ml of HEPES 1M, 1.15 ml of DMA, followed by 0.305 ml of a 10 mM DMA solution of L-DM4-Mal-PEG4-CONHS activated ester. After 7 hour at room temperature, the crude conjugation medium is diluted with 70 ml of HGS buffer and purified by TFF on Pellicon 3 cassette. The sample is diafiltered against ~10 sample volumes of HGS buffer and then collected. The TFF tank and lines are washed with an extra 10 ml of HGS buffer. The two solutions are mixed, concentrated on Amicon 15 and filter-sterilized through 0.22 µm PVDF. 8.0 ml of hu2H11R35R74-PEG4-Mal-DM4 immunoconjugate (c=5.09 mg/ml) was thus obtained. The immunoconjugate is then analyzed for final drug load and monomeric purity.

SEC analysis (method D): DAR (SEC)=5.3; RT=16.680; monomeric purity=99.5%

HRMS data (method C): see FIG. 3

1b.2. Preparation of L-DM4-Mal-PEG4-CONHS Activated Ester

Under magnetic stirring, at room temperature, 50 mg of L-DM4, 17.2 mg of supported DIEA (3.72 mmol/g), and a solution of 36.2 mg of 3-{2-[2-(2-{2-[3-(2,5-dioxo-2,5-dihydro-pyrrol-1-yl)-propionylamino]-ethoxy}-ethoxy)-ethoxy]ethoxy}-propionic acid 2,5-dioxo-pyrrolidin-1-yl ester (commercially available, SM(PEG)4, Pierce) in 360 µl of DMA are successively added. After 1 hours 30 minutes at room temperature the reaction medium is filtered, the solids are washed with AcOEt, and the combined filtrates are directly purified by flash-chromatography on 14 g of CN grafted silica gel (gradient of elution heptane:AcOEt:iPrOH with increasing contribution of iPrOH). After concentration of fractions containing the expected product under reduce pressure, 29.8 mg of L-DM4-Mal-PEG4-CONHS activated ester are obtained in the form of a colourless glass, the characteristics of which are as follows:

Mass Spectra: Method A

Retention time (min)=1.24/1.25 (2 diastereoisomers)

[M+H]+: m/z 1293

[M−H+HCO2H]−: m/z 1337

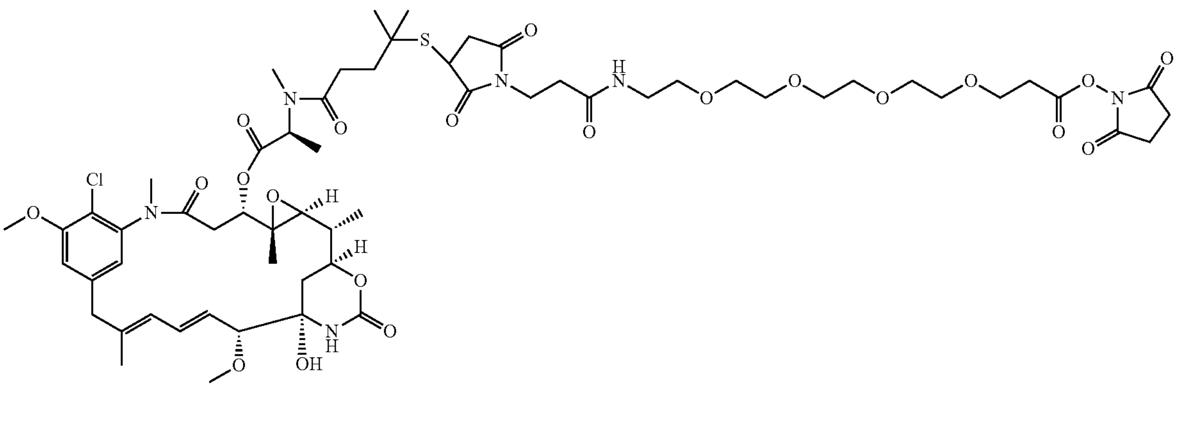 [SMILES: COc1cc2cc(c1Cl)N(C)C(=O)C[C@H](OC(=O)[C@H](C)N(C)C(=O)CCC(C)(C)SC1CC(=O)N(CCC(=O)NCCOCCOCCOCCOCCC(=O)ON3C(=O)CCC3=O)C1=O)[C@]1(C)O[C@H]1[C@H](C)[C@@H]1C[C@@](O)(NC(=O)O1)[C@H](OC)/C=C/C=C(\C)C2]

Example 1c

Preparation of Conjugate Linked with SPDB hu2H11R35R74-SPDB-$DM_4$

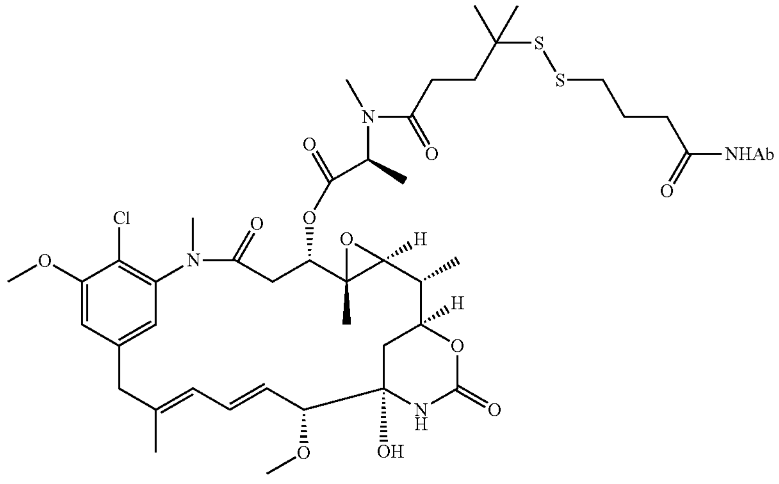

Humanized 2H11R35R74 antibodies were conjugated to L-DM4 N2' deacetyl-N2'(4-methyl-4-mercapto-1-oxopentyl)-maytansine using SPDB (4-[2-pyridyldithio]butanoic acid N-hydroxsuccinimde ester) linker using the same protocol as previously described in WO 2008010101A9 with other hu2H11 antibodies. Briefly, the antibody was modified at 8 mg/mL with 5.5 or 6.5 folds molar excess of SPDB for hu2H11 and hu37.3D7 respectively. The reaction was carried out in Buffer A (50 mM KPi/50 mM NaCl/2 mM EDTA, pH 6.5, 95% v/v) with EtOH (5% v/v) for 90 minutes at room temperature. The modified antibody was then purified by SephadexG25 desalting column with Buffer A. Next, the modified antibody was reacted with a 1.7-fold molar excess of DM4 over SPDB linker. The reaction was carried out at 2.5 mg/mL antibody in Buffer A (97% v/v) and DMA (dimethylacetamide, 3% v/v) at room temperature for 20 hours. The conjugate was purified by SephadexG25 desalting column with 10 mM Histidine, 130 mM Glycine, 5% sucrose, pH5.5. The drug to antibody ratio was 4.0 for hu37.3D7-SPDB-DM4 and 3.1 for hu2H11-SPDB-DM4.

Example 1d

Preparation of Conjugate hu2H11R35R74-PEG4-NMeAc-DM4

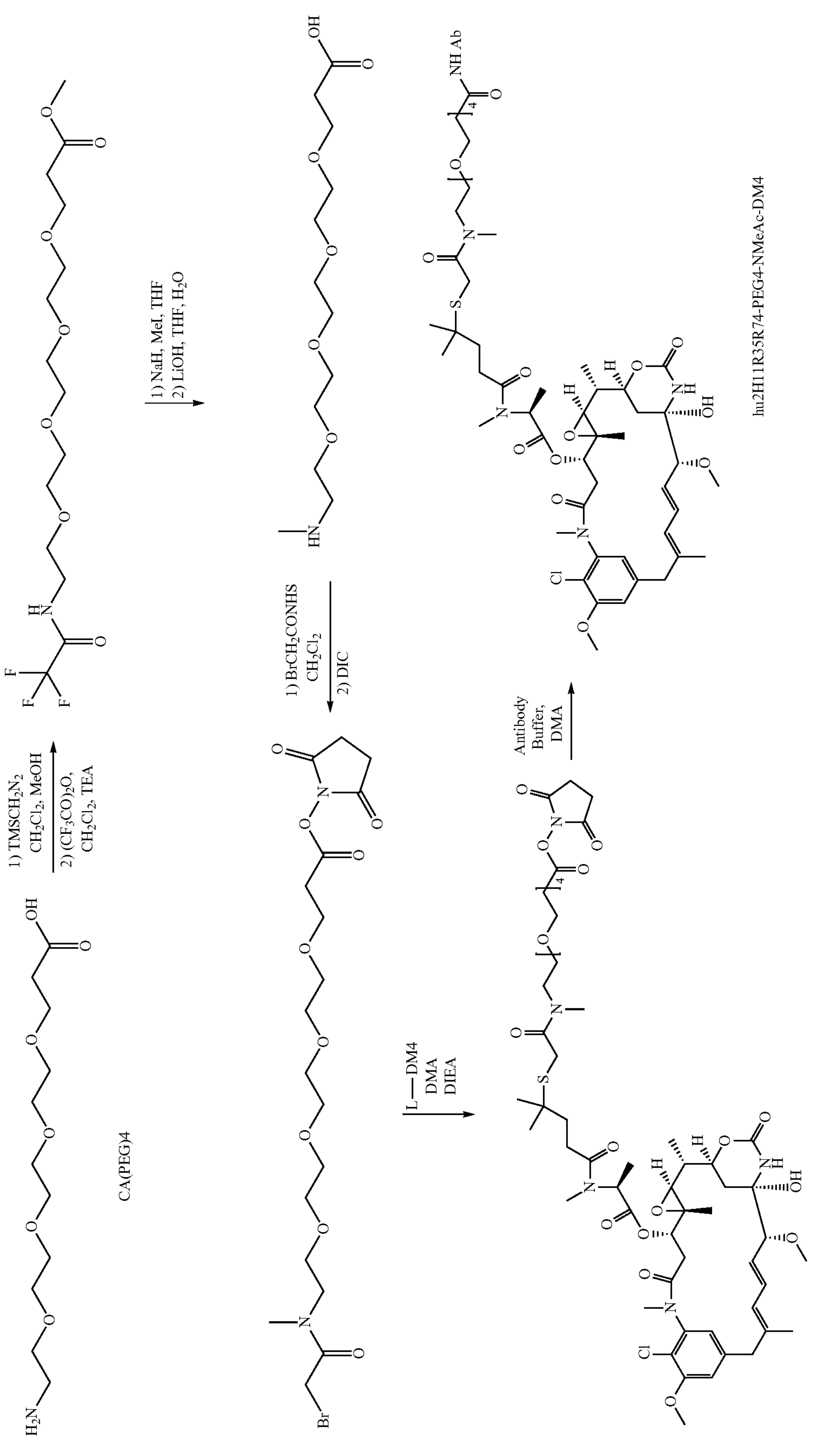
CA(PEG)4
1) TMSCH$_2$N$_2$
CH$_2$Cl$_2$, MeOH
2) (CF$_3$CO)$_2$O,
CH$_2$Cl$_2$, TEA
1) NaH, MeI, THF
2) LiOH, THF, H$_2$O
1) BrCH$_2$CONHS
CH$_2$Cl$_2$
2) DIC
L—DM4
DMA
DIEA
Antibody
Buffer,
DMA
hu2H11R35R74-PEG4-NMeAc-DM4

1d.1 Preparation of Conjugate hu2H11R35R74-PEG4-NMeAc-DM4

Under magnetic stirring at RT, 4 ml of hu2H11R35R74 (14.36 mg/ml in buffer A) are added, then 7.5 ml of buffer A, 1.45 ml of HEPES 1M, 1.05 ml of DMA, followed by 0.39 ml of a 10 mM DMA solution of L-DM4-AcNMe-PEG4-CONHS activated ester. After 30 min at RT, an extra 0.19 ml of 10 mM DMA solution of L-DM4-AcNMe-PEG4-CONHS activated ester is added. After 3 hrs at RT, the crude conjugation medium is diluted with 65 ml of HGS buffer and purified by TFF on Pellicon 3 cassette. The sample is diafiltered against ~10 sample volumes of HGS buffer and then collected. The TFF tank and lines are washed with an extra 10 ml of HGS buffer. The two solutions are mixed, concentrated on Amicon 15 and filter-sterilized through 0.22 μm PVDF. 8.5 ml of hu2H11R35R74-PEG4-NMeAc-DM4 conjugate (c=6.01 mg/ml) was thus obtained. The conjugate is then analyzed for final drug load and monomeric purity. SEC analysis (D): DAR (SEC)=5.5; RT=16.7 min; monomeric purity=99.4%; HRMS data: see FIG. 14.

1d.2 Preparation of L-DM4-AcNMe-PEG4-CONHS Activated Ester

Under magnetic stirring at RT, 133.4 mg of L-DM4 are introduced in a glass vial. A solution of 85 mg of 3-{2-[2-(2-{2-[(2-bromo-acetyl)-methyl-amino]-ethoxy}-ethoxy)-ethoxy]-ethoxy}-propionic acid 2,5-dioxo-pyrrolidin-1-yl ester in 0.2 ml of DMA is then added, followed by 32.9 μl of DIEA. After 1 hours at RT, the reaction medium is purified by flash-chromatography on 30 g of C18-grafted silica gel (gradient of elution water:acetonitrile 95:5 to 5:95 by volume). After concentration of fractions containing the desired product under RP, 71.3 mg of L-DM4-AcNMe-PEG4-CONHS activated ester are obtained in the form of a colourless glass-like product. Mass spectra (D): RT=0.98 min; $[M+H-H_2O]+$: m/z 1178 (main signal); [M+Na]+: m/z 1218; $[M-H+HCO_2H]-$: m/z 1240; 1H NMR (500 MHz, δ in ppm, chloroform-d): 0.81 (s, 3H); 1.20 to 1.33 (m, 13H); 1.42 to 1.52 (m, 1H); 1.56 to 1.61 (m, 1H); 1.65 (s, 3H); 1.73 to 1.83 (m, 1H); 1.96 to 2.04 (m, 1H); 2.19 (dd, J=2.8 and 14.4 Hz, 1H); 2.29 to 2.41 (m, 1H); 2.55 to 2.66 (m, 2H); 2.83 to 2.93 (m, 12H); 3.04 (d, J=9.8 Hz, 1H); 3.12 (d, J=12.7 Hz, 1H); 3.18 to 3.25 (m, 5H); 3.37 (s, 3H); 3.47 to 3.54 (m, 3H); 3.57 to 3.68 (m, 15H); 3.85 (t, J=6.6 Hz, 2H); 3.99 (s, 3H); 4.29 (m, 1H); 4.79 (dd, J=2.8 and 12.2 Hz, 1H); 5.41 (q, J=6.7 Hz, 1H); 5.68 (dd, J=9.3 et 15.2 Hz, 1H); 6.23 (s, 1H); 6.43 (dd, J=11.0 and 15.2 Hz, 1H); 6.66 (s, 1H); 6.74 (d, J=11.0 Hz, 1H); 6.83 (s, 1H).

1d.3 Preparation of 3-{2-[2-(2-{2-[(2-bromo-acetyl)-methyl-amino]-ethoxy}-ethoxy)-ethoxy]-ethoxy}-propionic acid 2,5-dioxo-pyrrolidin-1-yl ester

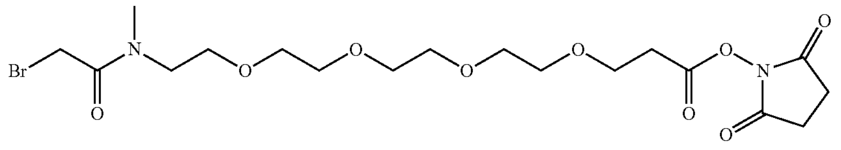 [SMILES: CN(CCOCCOCCOCCOCCC(=O)ON1C(=O)CCC1=O)C(=O)CBr]

Under magnetic stirring, at RT, in a round bottom flask, 115.1 mg of 3-(2-{2-[2-(2-methylamino-ethoxy)-ethoxy]ethoxy}-ethoxy)-propionic acid, 1.5 ml of DCM, 97.3 mg of bromo-acetic acid 2,5-dioxo-pyrrolidin-1-yl ester are successively introduced. After 2 h, 72 μl of DIEA are added, and after a further 1 hour at RT, 70.2 μl of DIC are added. The crude reaction medium is kept 4 hrs at RT, 16 hrs at −20° C., and then purified by flash-chromatography on 30 g of silica gel (gradient of elution DCM:methanol from 0:100 to 3:97 by volume). After concentration of fractions containing the desired product under RP, 85.8 mg of 3-{2-[2-(2-{2-[(2-bromo-acetyl)-methyl-amino]-ethoxy}-ethoxy)-ethoxy]-ethoxy}-propionic acid 2,5-dioxo-pyrrolidin-1-yl ester are obtained in the form of a white solid. Mass spectra (A): RT=0.84 min; [M+H]+: m/z 497/499

1d.4 Preparation of 3-(2-{2-[2-(2-methylamino-ethoxy)-ethoxy]-ethoxy}-ethoxy)-propionic acid

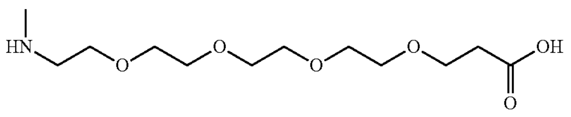 [SMILES: CNCCOCCOCCOCCOCCC(=O)O]

Under an inert atmosphere of argon, in a round bottom flask, with magnetic stirring, 120.1 mg of 3-[2-(2-{2-[2-(2,2,2-trifluoro-acetylamino)-ethoxy]-ethoxy}-ethoxy)-ethoxy]-propionic acid methyl ester, 1 ml of anhydrous THF and 59.8 μl of $CH_3I$ and successively introduced. The reaction medium is cooled with a ice/water bath at about 0° C., and 16.1 mg of NaH (50% pure in oil) is slowly added by small portions. After 15 min at 0° C., and 1 hr at RT, the crude reaction medium is concentrated to dryness under RP, and diluted with 0.5 ml of THF and 0.8 ml of water. At RT, 30.6 mg of LiOH is then added to the reaction medium. The crude reaction medium is kept 2 hrs at RT, 16 hrs at −20° C., and then purified by flash-chromatography on 30 g of C18-grafted silica gel (gradient of elution water:acetonitrile from 95:5 to 5:95 by volume). After concentration of fractions containing the desired product under RP, 115.3 mg of 3-(2-{2-[2-(2-methylamino-ethoxy)-ethoxy]-ethoxy}-ethoxy)-propionic acid are obtained in the form of a yellow oil.

1d.5 Preparation of 3-[2-(2-{2-[2-(2,2,2-trifluoro-acetylamino)-ethoxy]-ethoxy}-ethoxy)-ethoxy]-propionic acid methyl ester

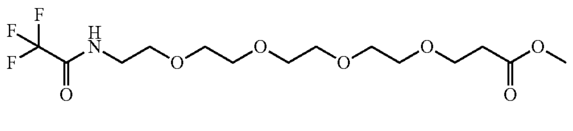 [SMILES: COC(=O)CCOCCOCCOCCOCCNC(=O)C(F)(F)F]

Under an inert atmosphere of argon, in a round bottom flask, with magnetic stirring, 230 mg of 3-(2-{2-[2-(2-amino-ethoxy)-ethoxy]-ethoxy}-ethoxy)-propionic acid (CA $(PEG)_4$, Pierce) 2 ml of DCM and 1 ml of methanol are successively introduced. At RT, 1 ml of trimethylsilyldiazomethane (2M solution in hexane) is slowly added to the reaction medium. After 2 hrs at RT, the excess of triméthylsilyldiazomethane is neutralized by addition of acetic acid. The crude reaction medium is then evaporated to dryness under RP. The residue obtained is diluted with 2 ml of DCM, cooled to 0° C. with a water-ice bath, then 363 μl of TEA and 300 μl of TFAA are successively added. After 2 hrs 30 min at RT and 19 hrs at −20° C., 363 μl of TEA and 300 μl of TFAA are successively added. After 4 hrs 30 min at RT and the crude medium is stocked at −20° C. and then purified by flash-chromatography on 30 g of C18-grafted silica gel (gradient of elution water:acetonitrile from 95:5 to 5:95 by volume). After concentration of fractions containing the desired product under RP, 123 mg of 3-[2-(2-{2-[2-(2,2,2-trifluoro-acetylamino)-ethoxy]-ethoxy}-ethoxy)-ethoxy]-propionic acid methyl ester are obtained in the form of a pale-yellow oil. Mass spectra (A): RT=0.90 min; [M+H]+: m/z 376; [M−H]−: m/z 374.

Example 1e

Preparation of Conjugate hu2H11R35R74-PEG8-NHAc-DM4

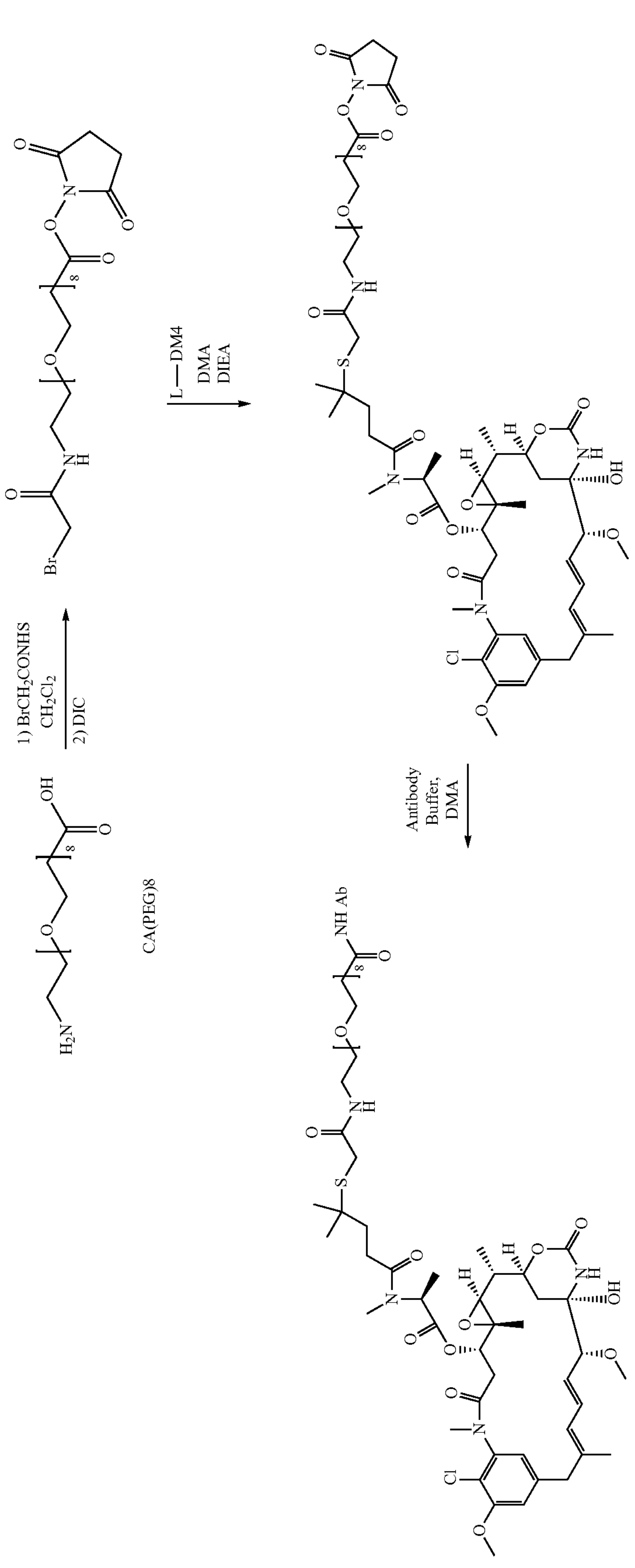
CA(PEG)8
L-DM4-AcNH-PEG8-CONHS
hu2H11R35R74-PEG8-AcNH-DM4

1e.1 Preparation of Conjugate hu2H11R35R74-PEG8-NHAc-DM4

Under magnetic stirring at RT, 4 ml of hu2H11R35R74 (14.36 mg/ml in buffer A) are added, then 7.5 ml of buffer A, 1.45 ml of HEPES 1M, 1.05 ml of DMA, followed by 0.405 ml of a 10 mM DMA solution of L-DM4-AcNMe-PEG8-CONHS activated ester. After 30 min at RT, an extra 0.1 ml of 10 mM DMA solution of L-DM4-AcNMe-PEG8-CONHS activated ester is added. After 1 hr 45 min at RT, the crude conjugation medium is diluted with 60 ml of HGS buffer and purified by TFF on Pellicon 3 cassette. The sample is diafiltered against ~10 sample volumes of HGS buffer and then collected. The TFF tank and lines are washed with an extra 10 ml of HGS buffer. The two solutions are mixed, concentrated on Amicon 15 and filter-sterilized through 0.22 μm PVDF. 7.0 ml of hu2H11R35R74-PEG8-AcNMe-DM4 conjugate (c=6.95 mg/ml) was thus obtained. The conjugate is then analyzed for final drug load and monomeric purity. SEC analysis (D): DAR (SEC)=5.0; RT=16.593 min; monomeric purity=99.5%; HRMS data: see FIG. 15.

1e.f Preparation of L-DM4-AcNH-PEG8-CONHS Activated Ester

Under magnetic stirring at RT, 65 mg of 3-{2-[2-(2-{2-[2-(2-{2-[2-(3-bromo-propionylamino)-ethoxy]-ethoxy}-ethoxy)-ethoxy]-ethoxy}-ethoxy)-ethoxy]-ethoxy}-propionic acid 2,5-dioxo-pyrrolidin-1-yl ester are introduced in a glass vial, followed by a solution of 67.7 mg of L-DM4 in 0.85 ml of DMA and 16.5 μl of DIEA. After 48 hrs at RT, the reaction medium is purified by flash-chromatography on 10 g of silica gel (gradient of elution DCM:MeOH 100:0 to 90:10 by volume). After concentration of fractions 18 to 26 under RP, 17 mg of L-DM4-AcNH-PEG8-CONHS activated ester are obtained in the form of a colourless glass. Mass spectra (B): RT=4.08 min; $[M+H-H_2O]+$: m/z 1340 (main signal); [M+Na]+: m/z 1380; $[M-H+HCO_2H]-$: m/z 1402; 1H NMR (400 MHz, δ in ppm, chloroform-d): 0.81 (s, 3H); 1.22 (s, 3H); 1.23 (s, 3H); 1.26 (m, 1H); 1.30 (d, J=6.8 Hz, 6H); 1.41 to 1.52 (m, 1H); 1.65 (s, 3H); 1.80 (m, 1H); 1.89 to 1.99 (m, 1H); 2.19 (m, 1H); 2.37 (m, 1H); 2.47 à 2.67 (m, 2H); 2.81 à 2.93 (m, 10H); 2.99 (d, J=16.6 Hz, 1H); 3.04 (d, J=9.8 Hz, 1H); 3.16 (d broad, J=13.7 Hz, 1H); 3.23 (s, 3H); 3.32 (s broad, 1H); 3.37 (s, 3H); 3.44 (m, 2H); 3.51 (d, J=9.1 Hz, 1H); 3.54 (t, J=5.4 Hz, 2H); 3.59 à 3.73 (m, 29H); 3.86 (t, J=6.6 Hz, 2H); 4.00 (s, 3H); 4.22 to 4.33 (m, 1H); 4.78 (dd, J=2.9 and 12.2 Hz, 1H); 5.43 (q, J=6.8 Hz, 1H); 5.67 (dd, J=9.0 et 15.2 Hz, 1H); 6.23 (s, 1H); 6.44 (dd, J=11.2 et 15.2 Hz, 1H); 6.65 (d, J=1.5 Hz, 1H); 6.75 (d, J=11.2 Hz, 1H); 6.86 (d, J=1.5 Hz, 1H); 7.02 à 7.13 (m, 1H).

1e.g Preparation of 3-{2-[2-(2-{2-[2-(2-{2-[2-(3-bromo-propionylamino)-ethoxy]-ethoxy}-ethoxy)-ethoxy]-ethoxy}-ethoxy)-ethoxy]-ethoxy}-propionic acid 2,5-dioxo-pyrrolidin-1-yl ester

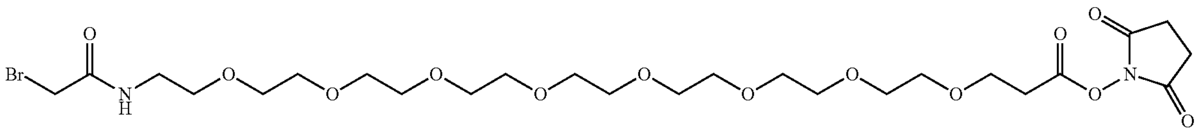 [SMILES: O=C(CBr)NCCOCCOCCOCCOCCOCCOCCOCCOCCC(=O)ON1C(=O)CCC1=O]

Under magnetic stirring at RT, 100 mg of 3-(2-{2-[2-(2-amino-ethoxy)-ethoxy]-ethoxy}-ethoxy)-propionic acid (CA(PEG)4, Pierce), 2 ml of DCM and 53.5 mg of bromo-acetic acid 2,5-dioxo-pyrrolidin-1-yl ester are successively introduced in a glass vial. After 1 hr at RT, 35.1 μl of DIC are added. After 1 hr, the crude reaction medium is filtered on sintered glass, concentrated to dryness under RP, dilute with 10 ml of AcOEt, filtered on sintered glass and concentrated to dryness under RP. 76.5 mg of 3-{2-[2-(2-{2-[2-(2-{2-[2-(3-bromo-propionylamino)-ethoxy]-ethoxy}-ethoxy)-ethoxy]-ethoxy}-ethoxy)-ethoxy]-ethoxy}-propionic acid 2,5-dioxo-pyrrolidin-1-yl ester are obtained in the form of a colourless oil. Mass spectra (A): RT=0.80 min; [M+H]+: m/z 659/661; $[M-H+HCO_2H]-$: m/z 703/705

Example 1f

Preparation of Conjugate hu2H11R35R74-PEG4-Allyl-DM4

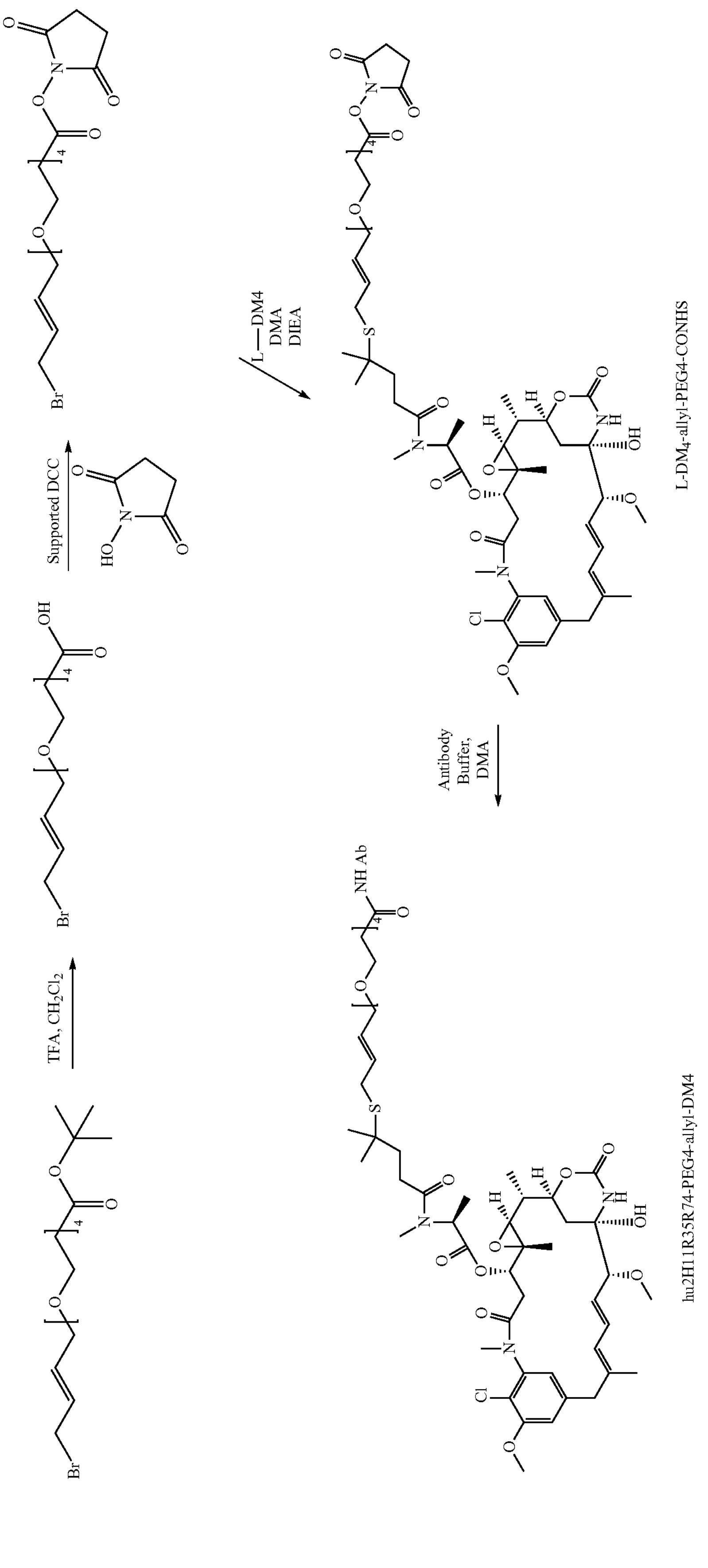
L-DM4-allyl-PEG4-CONHS
hu2H11R35R74-PEG4-allyl-DM4

1f.1 Preparation of Conjugate hu2H11R35R74-PEG4-Allyl-DM4

Under magnetic stirring at RT, 4 ml of hu2H11R35R74 (14.36 mg/ml in buffer A) are added, then 7.5 ml of buffer A, 1.45 ml of HEPES 1M, 1.14 ml of DMA, followed by 0.3 ml of a 10 mM DMA solution of L-DM4-Allyl-PEG4-CONHS activated ester. After 30 min at RT, an extra 0.125 ml of 10 mM DMA solution of L-DM4-Allyl-PEG4-CONHS activated ester is added. After 1 hr 25 min at RT, the crude conjugation medium is diluted with 65 ml of HGS buffer and purified by TFF on Pellicon 3 cassette. The sample is diafiltered against ~10 sample volumes of HGS buffer and then collected. The TFF tank and lines are washed with an extra 10 ml of HGS buffer. The two solutions are mixed, concentrated on Amicon 15 and filter-sterilized through 0.22 μm PVDF. 8.0 ml of hu2H11R35R74-PEG4-Allyl-DM4 conjugate (c=5.22 mg/ml) was thus obtained. The conjugate is then analyzed for final drug load and monomeric purity. SEC analysis (H): DAR (SEC)=5.3; RT=16.767 min; monomeric purity=99.4%; HRMS data: see FIG. 16.

1f.2 Preparation of L-DM4-Allyl-PEG4-CONHS Activated Ester

Under magnetic stirring at RT, 70 mg of L-DM4, 45 mg of 3-(2-{2-[2-(4-bromo-but-2-enyloxy)-ethoxy]-ethoxy}-ethoxy)-propionic acid 2,5-dioxo-pyrrolidin-1-yl ester (Bromo-Allyl-PEG$_4$-CONHS), 0.5 ml of DMA and 23.5 μl of DIEA are successively introduced in a glass vial. After 2 hrs at RT and 17 hrs at −20° C., 50 μl of DIEA is added. After 24 hrs at RT, the reaction medium is purified by flash-chromatography on 30 g of C-18 grafted silica gel (gradient of elution water:acetonitrile 95:5 to 5:95 by volume). After concentration of fractions containing the expected product under RP, 47.1 mg of L-DM4-Allyl-PEG4-CONHS activated ester are obtained in the form of a white solid. Mass spectra (D): RT=1.06 min; [M+Na]+: m/z 1173; 1H NMR (500 MHz, 8 in ppm, chloroform-d): 0.81 (s, 3H); 1.18 à 1.39 (m, 13H); 1.42 to 1.52 (m, 1H); 1.58 (d, J=13.4 Hz, 1H); 1.65 (s, 3H); 1.73 to 1.82 (m, 1H); 1.86 à 1.95 (m, 1H); 2.19 (d, J=14.3 Hz, 1H); 2.40 (m, 1H); 2.51 to 2.65 (m, 2H); 2.82 to 2.95 (m, 9H); 2.98 to 3.07 (m, 2H); 3.12 (d, J=12.6 Hz, 1H); 3.18 to 3.27 (m, 1H); 3.23 (s, 3H); 3.36 (s, 3H); 3.51 (d, J=9.1 Hz, 1H); 3.54 à 3.82 (m, 13H); 3.86 (t, J=6.4 Hz, 2H); 3.91 à 3.95 (m, 2H); 3.99 (s, 3H); 4.28 (t, J=11.0 Hz, 1H); 4.78 (dd, J=2.6 et 11.9 Hz, 1H); 5.44 (q, J=6.7 Hz, 1H); 5.49 to 5.63 (m, 2H); 5.68 (dd, J=9.1 and 15.0 Hz, 1H); 6.24 (s, 1H); 6.43 (dd, J=11.1 and 15.0 Hz, 1H); 6.66 (s, 1H); 6.77 (d, J=11.1 Hz, 1H); 6.83 (s, 1H).

1f.3 Preparation of 3-(2-{2-[2-(4-bromo-but-2-enyloxy)-ethoxy]-ethoxy}-ethoxy)-propionic acid 2,5-dioxo-pyrrolidin-1-yl ester

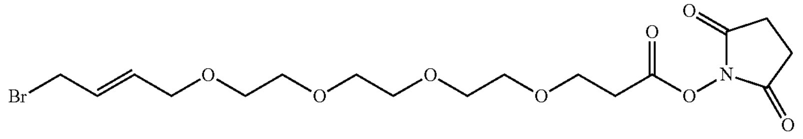 [SMILES: O=C(CCOCCOCCOCCOC/C=C/CBr)ON1C(=O)CCC1=O]

At RT, 200 mg of 3-(2-{2-[2-(4-bromo-but-2-enyloxy)-ethoxy]-ethoxy}-ethoxy)-propionic acid, 4 ml of DCM and 232.3 mg of supported DCC (2 equivalents) are successively introduced in a glass vial. After 1 hr at RT, 64.8 mg of NHS are added. After 5 hrs at RT, the crude reaction medium is filtered on sintered glass, solids are washed with DCM, and the combined filtrates are concentrated to dryness under RP. Purification by flash-chromatography on 15 g of silica gel (gradient of elution MeOH:DCM 0:100 to 10:90 by volume), and concentration of fractions containing the expected product under RP, afforded 46 mg of 3-(2-{2-[2-(4-bromo-but-2-enyloxy)-ethoxy]-ethoxy}-ethoxy)-propionic acid 2,5-dioxo-pyrrolidin-1-yl ester (Bromo-Allyl-PEG4-CONHS) are obtained in the form of a pale yellow oil. Mass spectra (A): RT=1.02 min; [M+H]+: m/z 454/456; [M+Na]+: m/z 476/478; [M−H+HCO2H]−: m/z 498/500.

1f.4 Preparation of 3-(2-{2-[2-(4-bromo-but-2-enyloxy)-ethoxy]-ethoxy}-ethoxy)-propionic acid

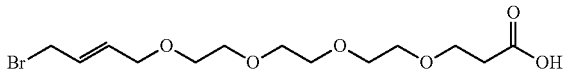 [SMILES: O=C(O)CCOCCOCCOCCOC/C=C/CBr]

At RT, a solution of 1 g of 3-(2-{2-[2-(4-bromo-but-2-enyloxy)-ethoxy]-ethoxy}-ethoxy)-propionic acid tert-butyl ester (commercially available), 6 ml of TFA and 3 ml of DCM is stirred during 3 hrs, and then concentrated to dryness under RP. The oily residue is diluted with toluene and concentrated to dryness under RP affording 853 mg of 3-(2-{2-[2-(4-bromo-but-2-enyloxy)-ethoxy]-ethoxy}-ethoxy)-propionic acid in the form of a brown oil.

Example 1q

Preparation of Conjugate hu2H11-PEG4-NHAc-DM4

Conjugate hu2H11-PEG4-NHAc-DM4 could be prepared in a manner similar to example 1: under stirring, at RT, 1 ml of hu2H11 (8.52 mg/ml in buffer A) is added, then 0.7 ml of buffer A, 0.213 ml of HEPES1M, 0.7 ml of DMA, followed by 0.085 ml of a 10 mM DMA solution of L-DM4-AcNH-PEG4-CONHS activated ester diluted with 0.128 ml of DMA. After 2 hrs at RT, the crude medium is concentrated on Amicon 4 at 7000 G, buffer exchanged with HGS buffer on Nap-10 column, and finally purified on a 5 ml Zeba column. 1.15 ml of hu2H11-PEG4-NHAc-DM4 conjugate (c=3.78 mg/ml) was thus obtained. The conjugate is then analyzed for final drug load and monomeric purity. SEC analysis (method D): DAR (UV)=6.6; DAR (SEC)=5.6; RT=15.387 min; monomeric purity=99.7%; HRMS data: see FIG. 17.

Example 2

Inhibition of EphA2 Autophosphorylation Activity by hu2H11R35R74

Materials and Methods

Cell Lines and Antibodies

The breast adenocarcinoma cell line MDA-MB-231 was obtained from ECAAC (ref. #92020424). The non-small cell lung carcinoma cell line NCI-H1299 was obtained from ATCC (ref. #CRL-5803). Both cell lines were maintained in Dulbecco's modified Eagle medium (DMEM) supplemented with 10% heat inactivated foetal calf serum and 2 mM L-Gln. The recombinant mouse Ephrin-A1 extracellular domain/Fc chimera (EphrinA1/Fc) was obtained from Sigma (ref. #E 9902) or from R & D Systems (ref. #602-A1). The anti-Eck/EphA2 clone D7 antibody (Ab) and the anti-phosphotyrosine Ab 4G10 were obtained from Millipore (ref. #05-480 and 05-321 respectively). The chKTI isotype control Ab was generated at Immunogen Inc. It corresponds to the chimeric version of the anti-Kunitz Soybean Trypsin Inhibitor Ab (KTI, ATCC ref. #HB9515) where the Ig heavy and light chain constant regions were replaced by the human κ light chain and human γ1 heavy chain. The recombinant Ab was purified at ImmunoGen (chKTI lot #2539-91) from culture supernatants of HEK293T cells transiently transfected with an expression plasmid for the heavy and light chains. The humanized anti-EphA2 Abs hu2H11 (lot #LP08191) and hu2H11R35R74 (lot #LP09077) were produced at Sanofi-Aventis from stably transfected Lonza Chinese hamster ovary (CHO)/GS cell lines. Both Abs were purified from culture supernatants by affinity chromatography on protein A-sepharose followed by anion exchange chromatography according to standard procedures. An additional chromatography step was performed on ceramic hydroxyapatite. All preparations were stored in 1×PBS at 4° C. and tested for low endotoxin levels by using the kinetic LAL method. The anti-actin antibody clone C4 was from Millipore (ref. #MAB1501). The peroxydase (PO) conjugated goat anti-mouse IgG Ab was from Jackson Immunoresearch (ref. #115-035-003).

Induction of Phosphorylation

MDA-MB-231 cells were plated in complete medium in P100 Petri-dishes (5 plates per sample) at $3\times10^6$ cells per plate and incubated for 48 hrs at 37° C. in a $CO_2$ incubator. Cells were serum starved for 18 hrs and subsequently treated with hu2H11 or hu2H11-R35/R74 10 μg/mL or with EphrinA1/Fc at 2 μg/mL 10 min to 2 hrs at 37° C.

Inhibition of Phosphorylation

Serum starved MDA-MB-231 or NCI-H1299 cells were incubated with chKTI, hu2H11 or hu2H11R35R74 (10 μg/mL) 1 hrs at 37° C. EphrinA1/Fc was then added at 1 μg/mL and cells were further incubated 10-30 min at 37° C.

Preparation of Cell Extracts

Cell samples were harvested on ice by scraping, transferred into 15 mL conical tubes and centrifuged 5 min at 1300 rpm. After one wash with 1× phosphate buffered saline (PBS; Invitrogen #14190) cells were resuspended in 300 μL of lysis buffer (Biosource ref. #FNN0011) extemporaneously supplemented with 1 mM phenylmethylsulphonyl fluoride (PMSF), 1× protease inhibitor cocktail (Sigma ref. #P2714) and 1× Halt phosphatase inhibitor (Pierce ref. #78420). Cell extracts were kept on ice 45 min with occasional vortexing, centrifuged 10 min at 15000 rpm and kept at −80° C. until further use. Protein concentration was determined by the bicinchoninic acid (BCA) method using a kit from Pierce (ref. #23227).

Immunoprecipitation

A pre-cleaning step of cell extracts (0.3-0.5 mg per sample) was performed by adding protein G Sepharose 4 fast flow (GE Healthcare Life Sciences ref. #17-0618-01) previously equilibrated in lysis buffer (1 hr at 4° C. on a rotator). Incubation was performed 30 min at 4° C. on a rotator. Samples were centrifuged 2 min at 1500 rpm, supernatant were collected and incubated over night on a rotator with the anti-EphA2 Ab clone D7 (4 μL per sample). Immunoprecipitation was performed with Protein G Sepharose 4 hrs at 4° C. on a rotator. Samples were centrifuged 2 min at 1500 rpm at 4° C. and washed 3 times 5 min with 100 μL of lysis buffer. Immunoprecipitated beads were resuspended in 50 μL of 4× NuPAGE LDS sample buffer (Invitrogen ref. #NP0007) supplemented with NuPAGE reducing agent (Invitrogen ref. #NP0009), heated 5 min at 95° C. centrifuged 5 min 1500 rpm and kept at −20° C. or subjected to electrophoresis.

Immunoblotting

Immunoprecipitates or cell extracts were loaded on a 4-12% Bis-Tris Midi gel (Invitrogen #NP0322BOX) with reference molecular weight markers (GE healthcare Life Sciences ref. #RPN800) and electrophoresis was performed 3 hrs at 150 V in MOPS-SDS buffer 1× (Invitrogen ref. #NP0001). Electroblotting was performed on PVDF membranes (Invitrogen ref. #LC2007) with an i-blot™ apparatus (Invitrogen) using programme 3. Blocking of the membranes was performed in TBST 1× (i.e. Tris-Buffered Saline Sigma ref. #T 5912, 0.1% Tween 20 Sigma ref. #P1379) supplemented with 5% Bovine serum albumin. Labeling with the anti-EphA2 Ab clone D7 or the anti-Phosphotyrosine 4G10 Ab were performed over night at 4° C. in the same buffer. Labeling with anti-Actin Ab clone C4 was performed 1 h at room temperature.

After subsequent washing of the membranes with 1×TBST development of the Immunoblots was performed using the PO-conjugated goat anti-mouse Ab and the ECL kit from Perkin Elmer (ref. #NEL 104001 EA). Luminescence was read on a Fuji4000 apparatus.

Results

Induction of the phosphorylation of EphA2 by hu2H11 or hu2H11R35R74Abs was investigated in MDA-MB231 cells using recombinant EphrinA1/Fc as a positive control. Results are presented in FIG. 4. No induction of phosphorylation could be detected with any of the two Abs from 10 min to 2 hrs while recombinant EphrinA1/Fc induced a strong phosphorylation of the EphA2 receptor at 10 min with a decline of the signal starting at 1 hr and a degradation of the receptor beginning to be visible at 2 hrs.

Inhibition of the phosphorylation of EphA2 after induction by EphrinA1/Fc was investigated in NCI-H1299 and MDA-MB-231 cells. Results are presented in FIGS. 5A and 5B. In both cases, pre-incubation of the cells with any of the two Abs inhibited phosphorylation of the EphA2 receptor by EphrinA1/Fc.

We can conclude that hu2H11 and hu2H11R35R74 have similar inhibitory activity on the EphA2 receptor.

Example 3

Binding Characterization of Conjugated Anti-EphA2 Antibodies, hu2H11R35R74 and hu2H11

The interaction of the anti-EphA2 antibodies hu2H11 and hu2H11R35R74, either naked or conjugated to DM4 with the PEG4-NHAc linker, with immobilized EphA2-Fc was monitored by surface plasmon resonance detection using a BIAcore 3000 instrument (GE healthcare, N°CH321). EphA2-Fc (10 μg/ml; Acetate buffer pH=4.5) was coupled to the matrix of a C1 sensor chip (GE healthcare BR-1005-40) at 10 μl/min using a standard amine coupling protocol with EDC (N-ethyl-N'-[dimethyl-amino-propyl]carbodiimide)/NHS (N-hydroxysuccinimide). The density was controlled at an increased response level of ~100 response units (RU) in kinetic binding experiments. IgGs were diluted in 0.01 M Hepes, pH 7.4 containing 0.15 M NaCl, 3 mM EDTA, and 0.005% P20. All subsequent dilutions were made in the same buffer. All binding experiments were performed at 25° C. with IgG concentrations typically ranging from 50 to 0.2 nM at a flow rate of 50 μl/min.

Data were collected for approximately 12 min (2 min association time and 10 min dissociation time) and 1 min pulse at 30 μl/min of 1M NaCl, 50 mM NaOH was used to regenerate the surfaces. IgGs were also flowed over an uncoated cell and the sensorgrams from the blank runs were substracted from those obtained with EphA2-Fc coupled chips. Data were fitted to a 1:1 Langmuir binding model with drifting baseline. This algorithm calculates both the $k_{on}$ and the $k_{off}$, from which the apparent equilibrium dissociation constant $K_D$, is deduced as the ratio of the two rate constants ($k_{off}/k_{on}$). The values obtained are indicated in Table I.

The affinity constant was first measured with both naked hu2H11 and hu2H11R35R74. Analysis of the binding data of hu2H11 to EphA2-Fc give a $K_D$ of 0.30 nM; this value was similar to the $K_D$ of hu2H11R35R74 (0.22 nM). However, when conjugated antibodies were used in the assay, the results were dramatically different: conjugated hu2H11 with a high drug-to-antibody-ratio such as 7.5 displayed a $K_D$ increased by 5.4 fold, when compared to the naked antibody (1.62 nM vs. 0.30 nM). On the other hand, the $K_D$ the hu2H11R35R74 conjugated at a drug-to-antibody ratio of 7.4 was not different from the one of the naked antibody (0.27 nM vs. 0.22 nM). Moreover, the $K_D$ was not significantly different for drug-to-antibody ratios ranging from 5.6 to 8.4.

We conclude that the affinity of the 2H11R35R74 antibody is not affected by conjugation, even at high-drug-to-antibody ratios.

Example 4

Inhibition of Growth of EphA2 Expressing Tumor Cells by Humanized 2h11R35R74-PEG4-Mal-DM4

Inhibition of Lovo Tumor Cells

Lovo tumor cells (2000 per well) were plated in 96-well tissue culture plates in complete serum-containing media. Conjugates were serially diluted and added to triplicate wells at concentrations ranging between $10^{-7}$ and $10^{-12}$ M. Cells were cultured at 37° C./5% $CO_2$ in the presence of the antibody-cytotoxic compound conjugates for 5 days, after which time a 4 h WST8 assay was performed according to the manufacturer's instructions (Dojindo Cell Counting Kit-8, Cat. #CK04) to evaluate cell survival and growth. Cell-free reagent blanks were subtracted from the test well readings and the data were plotted as surviving fractions obtained by dividing readings of the conjugate-treated cells by the average of readings from control wells of vehicle-treated cells.

The cytotoxic potency of two lots of hu2H11R35R74-PEG4-Mal-DM4 at high maytansine/antibody ratios (6.70 D/A and 7.00 D/A) was compared with that of a wild-type hu2H11-PEG4-Mal-DM4 conjugate having a comparable maytansine/antibody ratio (6.99 D/A). As may be seen in FIG. 7, the two hu2H11R35R74-PEG4-Mal-DM4 conjugates showed higher potency than the corresponding conjugate of the wild-type hu2H11 against the EphA2-positive Lovo cell line (Table II).

Example 5

Inhibition of Growth of EphA2 Expressing Tumor Cells by Humanized 2h11R35R74-PEG4-NHAc-DM4

Inhibition of Growth of MDA-MB231 and SKMEL28

Cells in exponential phase of growth were trypsinized and resuspended in their respective culture medium (DMEM/F12 Gibco #21331; 10% SVF Gibco #10500-056; 2 nM Glutamine Gibco #25030 for MDA-MB231cells; DMEM (Gibco #11960) 10% SVF Gibco #10500-056; 2 nM Glutamine Gibco #25030 for SKMEL-28 cells). Cell suspension was distributed in 96-well Cytostar culture plates (GE Healthcare Europe, #RPNQ0163) in complete serum-containing media at a density of 5000 cells/well (MDA-MB231, SKMEL-28). After coating for 4 hours, serial dilutions of conjugates were added to triplicate wells at concentrations ranging between $10^{-7}$ and $10^{-12}$ M. Cells were cultured at 37° C./5% CO2 in the presence of the antibody-cytotoxic compound conjugates for 3 days. The 4th day, 10 μl of a solution of 14C thymidine (0.1 μCi/well (Perkin Elmer #NEC56825000) was added to each well. The uptake of 14C thymidine was measured 96 hours after the experiment has been started with a microbeta radioactive counter (Perkin Elmer). Cell-free reagent blanks were substracted from the test well readings and the data were plotted as surviving fractions obtained by dividing readings of the conjugate-treated cells by the average of readings from control wells of vehicle-treated cells. In some experiments, the naked antibody (2H11 or 2H11R35R74) was added to the wells at a concentration of 1 μM at the beginning of the experiment, and inhibition of proliferation was measured as previously described.

Results

Results reported in table III suggest that the 2H11R35R74-PEG4-NHAc-DM4 as well as the 2H11R35R74-PEG4-Mal-DM4 conjugates are better than former conjugates in terms of in vitro proliferation inhibition on MDA-MB231 cells and in vitro selectivity against antigen minus cells (SKMEL-28)

Example 6

Pharmacokinetics Study

The present study was designed to evaluate the pharmacokinetic behavior of the hu2H11R35R74-PEG4-NHAc-DM4 conjugate (DAR=5.5) in comparison to the hu2H11-SPDB-DM4 conjugate (DAR=3.9) in CD-1 mice. Animals received 20 mg/kg by IV route of each conjugate and blood was collected at 0, 8, 24, 48, 72, 120, 168, 240, 336, 504, 672 h post-injection. Plasma levels of antibody drug conjugates were measured to establish basic single dose pharmacokinetic parameters under standard conditions. The plasma concentrations of conjugates and their antibody component (total antibody, a sum of conjugated antibody and any de-conjugated antibody) were measured by specific ELISA techniques.

The clearance-related pharmacokinetic parameters for the antibody component of hu2H11-SPDB-DM4 (total) were calculated to be Cl (clearance) of 0.00043 L/h/kg, T1/2 (terminal half life) of 160 h, AUC 0-inf (area under the concentration time-curves from time zero to infinity) of 47,000,000 ng·h/mL, Vdss (steady-state volume of distribution) of 0.095 L/kg and CO (concentration at time 0) of 270,000 ng/mL.

The pharmacokinetic parameters for hu2H11-SPDB-DM4 conjugate were calculated to be Cl of 0.00070 L/h/kg, T1/2 of 87 h, AUC 0-inf of 28,000,000 ng·h/mL, Vdss of 0.080 L/kg and C0 of 360,000 ng/mL.

The PK parameters for the antibody component of hu2H11R35R74-PEG4-NHAc-DM4 (total) were Cl of 0.00027 L/h/kg, T1/2 of 190 h, AUC 0-inf of 73,000,000 ng·h/mL, Vdss of 0.068 L/kg and CO of 530,000 ng/mL.

Finally, the hu2H11R35R74-PEG4-NHAc-DM4 conjugate showed values of: 0.00036 L/h/kg for clearance, T1/2 of 150 h, AUC 0-inf of 56,000,000 ng·h/mL, Vdss of 0.069 L/kg and CO of 600,000 ng/mL.

In conclusion, hu2H11-SPDB-DM4 conjugate is cleared faster than hu2H11R35R74-PEG4-NHAc-DM4. Furthermore, compared with hu2H11-SPDB-DM4, hu2H11R35R74-PEG4-NHAc-DM4 showed a better exposure (AUC 0-inf) and a narrower separation between the total conjugated antibody and total antibody curves (compare FIGS. 7 and 8).

Example 7

Antitumor Effect of hu2H11R35R74-PEG4-NHAc-DM4 and hu2H11-PEG4-NHAc-DM4 Conjugate Against a Primary Colon Tumor, CR-LRB-004P Implanted in Female SCID Mice Materials and Methods For the evaluation of anti-tumor activity of conjugates, animals were weighed daily and tumors were measured 2 times weekly by caliper. Tumor weights were calculated using the formula mass (mg)=[length (mm)×width (mm)$^2$]/2. Antitumor activity evaluation was done at the highest non toxic dose (HNTD).

A dosage producing a 20% body weight loss (bwl) at nadir (mean of group) or 10% or more drug deaths, was considered an excessively toxic dosage. Animal body weights included the tumor weights. The primary efficacy end points are ΔT/ΔC, percent median regression, partial and complete regressions (PR and CR) and Tumor free survivors (TFS).

Changes in tumor volume for each treated (T) and control (C) are calculated for each tumor by subtracting the tumor volume on the day of first treatment (staging day) from the tumor volume on the specified observation day. The median ΔT is calculated for the treated group and the median ΔC is calculated for the control group. Then the ratio ΔT/ΔC is calculated and expressed as a percentage:

$$\%\ \Delta T/\Delta C = \frac{\text{median}(Tt - T0)}{\text{median}(t - C0)} \times 100$$

The dose is considered as therapeutically active when ΔT/ΔC is lower than 40% and very active when ΔT/ΔC is lower than 10%. If ΔT/ΔC is lower than 0, the dose is considered as highly active and the percentage of regression is dated (ref 1):

% tumor regression: is defined as the % of tumor volume decrease in the treated group at a specified observation day compared to its volume on the first day of first treatment.

At a specific time point and for each animal, % regression is calculated. The median % regression is then calculated for the group.

$$\%\ \text{regression (at } t) = \frac{volume_{t0} - volume_{t}}{volume_{t0}} \times 100$$

Partial regression (PR): Regressions are defined as partial if the tumor volume decreases to 50% of the tumor volume at the start of treatment.

Complete regression (CR): Complete regression is achieved when tumor volume=0 mm$^3$ (CR is considered when tumor volume cannot be recorded).

TFS: Tumor free is defined as the animals with undetectable tumors at the end of the study (>100 days post last treatment)

Results

The antitumor effect of hu2H11-PEG4-NHAc-DM4-conjugate and hu2H11R35R74-PEG4-NHAc-DM4 was evaluated at 2 dose levels against a measurable primary colon tumor, CR-LRB-004P, strongly expressing target, S.C. implanted in female SCID mice. Control group was left untreated. Doses were expressed in milligram of protein per kilogram. hu2H11R35R74-PEG4-NHAc-DM4 was administered at 40 and 10 mg/kg, by an intravenous (IV) bolus injection, on day 15. To give equivalent dose of DM4, hu2H11-PEG4-NHAc-DM4 was administered at 44 and 11 mg/kg.

As shown on Table V, using a single administration schedule in CR-LRB-004P tumor, hu2H11R35R74-PEG4-NHAc-DM4 was active at 40 and 10 mg/kg with a ΔT/ΔC of 28 and 39% respectively while hu2H11-PEG4-NHAc-DM4 was active only at 44 mg/kg with a ΔT/ΔC of 26%. At 10 mg/kg, hu2H11-PEG4-NHAc-DM4 was not active in this model.

From these results, hu2H11R35R74-PEG4-NHAc-DM4-conjugate at lower dose exhibited a better activity than hu2H11-PEG4-NHAc-DM4 conjugate.

Example 8

Impact of the DAR on the Anti-Tumor Activity of hu2H11R35R74-PEG4-NHAc-DM4 Against Prostatic Adenocarcinoma PC-3 in SCID Female Mice The effect of the DAR on the antitumor activity of antibody drug conjugate hu2H11R35R74-PEG4-NHAc-DM4 was evaluated comparing two low effective doses at six different Drug antibody ratios (DAR) on Prostatic PC-3 tumors S.C. implanted in female SCID. Control group was left untreated. Doses were expressed in milligram of protein per kilogram. DAR was determined by an UV method. hu2H11R35R74-PEG4-NHAc-DM4 was administered at 10 and 5 mg/kg with DARs at 3.4, 4.4, 5.9, 6.2, 7.4 and 8.4, respectively, by an intravenous (IV) bolus injection, on day 16.

Materials and Methods

For the evaluation of anti-tumor activity of conjugates, animals were weighed daily and tumors were measured 2 times weekly by caliper. Tumor weights were calculated using the formula mass (mg)=[length (mm)×width (mm)$^2$]/2. Antitumor activity evaluation was done at the highest non toxic dose (HNTD).

A dosage producing a 20% body weight loss (bwl) at nadir (mean of group) or 10% or more drug deaths, was considered an excessively toxic dosage. Animal body weights included the tumor weights. The primary efficacy end points are ΔT/ΔC, percent median regression, partial and complete regressions (PR and CR) and Tumor free survivors (TFS).

Changes in tumor volume for each treated (T) and control (C) are calculated for each tumor by subtracting the tumor volume on the day of first treatment (staging day) from the tumor volume on the specified observation day. The median ΔT is calculated for the treated group and the median ΔC is calculated for the control group. Then the ratio ΔT/ΔC is calculated and expressed as a percentage:

$$\%\ \Delta T/\Delta C = \frac{\text{median}(Tt - T0)}{\text{median}(t - C0)} \times 100$$

The dose is considered as therapeutically active when ΔT/ΔC is lower than 40% and very active when ΔT/ΔC is lower than 10%. If ΔT/ΔC is lower than 0, the dose is considered as highly active and the percentage of regression is dated (ref 1):

% tumor regression: is defined as the % of tumor volume decrease in the treated group at a specified observation day compared to its volume on the first day of first treatment.

At a specific time point and for each animal, % regression is calculated. The median % regression is then calculated for the group.

$$\%\ \text{regression (at } t) = \frac{volume_{t0} - volume_t}{volume_{t0}} \times 100$$

Partial regression (PR): Regressions are defined as partial if the tumor volume decreases to 50% of the tumor volume at the start of treatment.

Complete regression (CR): Complete regression is achieved when tumor volume=0 $mm^3$ (CR is considered when tumor volume cannot be recorded).

TFS: Tumor free is defined as the animals with undetectable tumors at the end of the study (>100 days post last treatment)

Results

As illustrated in table VI using a single administration schedule, hu2H11R35R74-PEG4-NHAc-DM4 at 10 mg/kg showed an activity from a DAR of 4.4 to the higher DAR of 8.4.

At 5 mg/kg, hu2H11R35R74-PEG4-NHAc-DM4 showed an activity from a DAR of 5.9 to the higher DAR of 8.4.

In conclusion, the DAR has an effect on the tumor activity of hu2H11R35R74-PEG4-NHAc-DM4 and one can deduce from these results that the optimal DAR of hu2H11R35R74-PEG4-NHAc-DM4 is at least equal to 5.9.

Example 9

Impact of the DAR on the PK Parameters of hu2H11R35R74-PEG4-NHAc-DM4

The pharmacokinetic properties of hu2H11R35R74-PEG4-NHAc-DM4 at different drug-antibody ratio (DAR) were evaluated in male CD-1 mice after a single intravenous administration of 20 mg/kg of conjugate. Plasma levels of conjugates were measured to establish basic single dose pharmacokinetic parameters under standard conditions. PK parameters were compared to those of the naked parental antibody. The plasma concentrations of conjugates and their antibody component (total antibody, a sum of conjugated antibody and any de-conjugated antibody) were measured by specific ELISA techniques.

Results (see FIGS. 9A and 9B) show a reverse correlation between the DAR values and the exposure to the total antibody components with AUC 0-inf values of 83,000,000, 61,000,000, 48,000,000, 46,000,000, 41,000,000 and 27,000,000 ng·h/mL for DAR of 0, 3.4, 4.3, 5.9, 6.6 and 7.4, respectively.

Similarly there is a reverse correlation between the DAR values and the exposure to the conjugate with AUC 0-inf values of 39,000,000, 30,000,000, 27,000,000, 29,000,000 and 20,000,000 ng·h/mL for DAR of 3.4, 4.3, 5.9, 6.6 and 7.4, respectively.

There is a perfect correlation between the DAR values and the elimination of the antibody component with Cl values of 0.00024, 0.00033, 0.00042, 0.00043, 0.00049 and 0.00074 L/h/kg for DAR 0, 3.4, 4.3, 5.9, 6.6 and 7.4, respectively.

Similarly there is almost a perfect correlation between the DAR values and the elimination of the conjugate with Cl values of 0.00051, 0.00066, 0.00075, 0.00069, 0.00099 L/h/kg for DAR 3.4, 4.3, 5.9, 6.6 and 7.4, respectively.

In conclusion, the DAR has an impact on the PK parameters with a decreased exposure and an increased elimination when the DAR increases.

According to results from efficacy and PK evaluation, the optimal DAR will be included between 5.9 and 7.4.

Example 10

Evaluation of hu2H11R35R74-PEG4-NHAc-DM4 Against Prostatic Adenocarcinoma PC-3 in SCID Female Mice The antitumor effect of antibody drug conjugate hu2H11R35R74-PEG4-NHAc-DM4 was evaluated at 8 dose levels against measurable prostatic PC-3 tumor, strongly expressing target, S.C. implanted in female SCID mice. Control group was left untreated. Doses are expressed in milligram of protein per kilogram.

They were administered at 160, 120, 80, 40, 20, 10, 5 and 2.5 mg/kg, by an intravenous (IV) bolus injection, on day 17.

Materials and Methods

For the evaluation of anti-tumor activity of conjugates, animals were weighed daily and tumors were measured 2 times weekly by caliper. Tumor weights were calculated using the formula mass (mg)=[length (mm)×width $(mm)^2$]/2. Antitumor activity evaluation was done at the highest non toxic dose (HNTD).

A dosage producing a 20% body weight loss (bwl) at nadir (mean of group) or 10% or more drug deaths, was considered an excessively toxic dosage. Animal body weights included the tumor weights. The primary efficacy end points are ΔT/ΔC, percent median regression, partial and complete regressions (PR and CR) and Tumor free survivors (TFS).

Changes in tumor volume for each treated (T) and control (C) are calculated for each tumor by subtracting the tumor volume on the day of first treatment (staging day) from the tumor volume on the specified observation day. The median ΔT is calculated for the treated group and the median ΔC is calculated for the control group. Then the ratio ΔT/ΔC is calculated and expressed as a percentage:

$$\%\ \Delta T/\Delta C = \frac{\text{median}(Tt - T0)}{\text{median}(t - C0)} \times 100$$

The dose is considered as therapeutically active when ΔT/ΔC is lower than 40% and very active when ΔT/ΔC is lower than 10%. If ΔT/ΔC is lower than 0, the dose is considered as highly active and the percentage of regression is dated (ref 1):

% tumor regression: is defined as the % of tumor volume decrease in the treated group at a specified observation day compared to its volume on the first day of first treatment.

At a specific time point and for each animal, % regression is calculated. The median % regression is then calculated for the group.

$$\% \text{ regression (at } t) = \frac{volume_{t0} - volume_{t}}{volume_{t0}} \times 100$$

Partial regression (PR): Regressions are defined as partial if the tumor volume decreases to 50% of the tumor volume at the start of treatment.

Complete regression (CR): Complete regression is achieved when tumor volume=0 $mm^3$ (CR is considered when tumor volume cannot be recorded).

TFS: Tumor free is defined as the animals with undetectable tumors at the end of the study (>100 days post last treatment)

Results

Using a single administration schedule, the highest dose of conjugate tested (160 mg/kg) was found to be toxic, inducing body weight loss and drug-related deaths.

As illustrated on table VIII at the HNTD (120 mg/kg) and other lowest doses, the compound was highly active. For all doses except for 2.5 mg/kg, hu2H11R35R74-PEG4-NHAc-DM4 induced partial regressions and for 120, 80 and 20 mg/kg, it induced complete regressions. In addition, the tumor model was cachexic, and the administration of the compound reduced the body weight loss at nadir in comparison with Control In conclusion, hu2H11R35R74-PEG4-NHAc-DM4 showed a high activity with a good dose-effect on Prostatic PC-3 tumor model.

Example 11

Mapping of the Epitope and Identification of the Paratope by Structure Determination of the Crystal Structure of the Extra-Cellular Domain of EphA2 Receptor in Complex with the Fab Fragment from Hu2h11-R35-R74 at 2.1 ÅResolution Material and Methods Initial crystallization trials were made on glycosylated extra-cellular domain of EphA2 receptor-Fc in complex with the Fab of hu2H11R35-74. Crystals were obtained only in presence of trypsin. These crystals were analyzed and peptide mapping showed that they contained the Fab, some portion of the N-terminal domain of extra-cellular domain of EphA2 and of the Fc. Another batch of complex was produced, this time using aglycosylated extra-cellular domain of EphA2 receptor with terminal His-tag, in complex with recombinant Fab fragment from hu2H11R34-R74-His. Both constructs of the EphA2 receptor provide the same structure of the complex between EphA2 receptor and hu2H11R34-R75.

Extra-cellular region of EphA2 receptor is made of 4 domains and has been shown to be very flexible: the LBD (Ligand Binding Domain), the CRD (Cystein-Rich Domain) and two Fibronectin Repeats, nFN3 and cFN3. The different domains were used as search models for molecular replacement calculation either alone or in combination; models of the variable and constant domains of the Fab were also produced and used, as well as a model of the Fc (pdb code 1IGT) to solve the crystal structure.

Various crystallization conditions were tested and a 2.1 Å dataset collected at the ESRF was used to solve the structure of the complex. It has enabled us to analyze the interface between the extra-cellular domain of EphA2 receptor and hu2H11R34-R74.

Even though the full length EphA2 extracellular region (25-534) was present initially, the crystals contain only the LBD and CRD domains of the protein (residues 25-325 or 327 depending on the crystal (here a sequential numbering is used).

Results

Epitope Mapping

FIG. 10: illustrates the mapping of the extra-cellular domain of EphA2 receptor epitope for hu2H11R34-R75 (epitope residues are defined as residues which contain atoms that lie within 4 Å from any atom of the CDR residues of hu2H11R34-R74Fab fragment).

The epitope of extra-cellular domain of EphA2 receptor when bound to Fab fragment of hu2H11R34-R74 is a conformational epitope that includes residues of the LBD domain Gly49, Lys50, Gly51, Asp53, Cys70, Asn71, Val72, Met73, Ser74, Gly75, Gln77, Phe108, Pro109, Gly110, Gly111, Ser113 and Ser114.

FIG. 11: shows residues from the extra-cellular domain of EphA2 receptor that are part of the epitope (represented in dark grey); residues in light grey are not visible in the crystal structures.

FIG. 12 A: represents the overall structure of the complex and FIG. 11B is a magnification of the part with the two mutations introduced in position 35 and 74.

Conjugation of hu2H11 occurs on surface lysine residues. Two of these were mutated into arginine. These two residues, heavy chain R74 and light chain R35 are depicted in FIG. 12B:

R74 lies in proximity of the interface, facing away from the extra-cellular domain of EphA2 receptor and about 10 Å from the nearest extra-cellular domain R35 is one of the paratope residues and it makes an H-bond with Asp53 from the extra-cellular domain of EphA2 receptor. A lysine reside would very likely make the same interactions with the antigen and its conjugation would clearly be detrimental for antibody binding.

Paratope Analysis

The interface between the extra-cellular domain of EphA2 receptor and hu2H11R35-R74 does not involve all CDR loop. As can be seen from FIG. 12, mainly the heavy chain CDRs are involved in binding. This suggests that changes in the CDRs of hu2H11, particularly in the light chain but not exclusively, can be introduced without adversely affect binding to the EphA2 receptor. Loop L3 of the light chain is not involved at all in the interface, while only one residue at the end of L1 (Arg35) interacts with the extra-cellular domain of EphA2. This implies that changes in loop L3 should not impact binding to EphA2 and that loop L1 should tolerate mutations/insertions of amino acid residues as long as they don't destabilize the conformation and orientation of Arg35 residue.

The paratope of hu2H11-R35-R74 for EphA2 receptor involves the following residues of the light chain: Arg35 of Loop L1, Tyr54, Arg58 and Asp60 of L2. It involves in the heavy chain the following residues: Thr30, Ala31, Tyr32 and Tyr33 of Loop H1, Asn52, Tyr54, Asn55 and Phe57 of H2 and Glu99, Phe100, Tyr101, Gly102, Tyr103 and Tyr105 of H3. A sequential numbering scheme is used for the light and heavy chains.

It might be possible to improve the affinity of the hu2H11-R35-R74 antibody for EphA2 receptor using the structural data and for instance by the approach described Clark et al (Protein Science (2006), 15:949-960) or Lippow et al (Nature Biotech (2007), 10:1171-76).

Loop H1: it might be possible to create additional interactions, for instance with Asp76, by judicious mutation of Thr H28.

Interactions between the light chain and Epha2 receptor do not involve many residues. Nevertheless, creating new interactions would probably require significant insertions in either loop L1 or L3.

Interactions between these loops and EphA2 receptor occur via rather large or long residues: any change in this environment might result in loss of binding affinity.

This X-ray structure highlights residues from the CDRs that can be mutated, that should not impact binding to EphA2.

In the following descriptions, residues from the paratope should not be modified, unless so specified to preserve the binding to the EphA2 receptor. It also understood that mutations in the CDRs should not affect the conformation and orientation of the residues from the paratope to preserve binding to the EphA2 receptor. Residue numbering is sequential and does not follow Kabbat conventions as used in Al-Lazikani ((1997) J. Mol. Biol. 273, 927-948). "X" represents "any residue", while "-" indicates that no modification should be made at this position.

In the CDR L1 (SEQ ID °4) except D 33 and R35 there is no restriction on sequence provided length of the loop is conserved and it adopts canonical structure L1-kappa4 as described in J. Mol. Biol. (1992) 227: 799-817, J. Mol. Biol. (1992) 227: 776-798 and in Al-Lazikani et al (cited supra). This means that torsion angles of peptide bonds fall within the accepted range defined in FIG. 5 of Al-Lazikani et al (cited supra).

Arg35 has been mutated to prevent conjugation on this residue. A Lys would nevertheless make the same interactions with EphA2 and hence it is predicted that parent hu2H11 antibody will make the same interaction with EphA2 receptor and engage the same epitope of EphA2 receptor.

An Asp is the preferred residue at position 33.

| Numbering | 26 | 27 | 28 | 29 | 30 | 31 | 32 | 33 | 34 | 35 | 36 | 37 |
|---|---|---|---|---|---|---|---|---|---|---|---|---|
| Initial sequence | S | Q | S | L | I | H | S | D | G | R | T | Y |
| Suggested mutations | X | X | X | X | X | X | X | D | X | R/K | X | X |

In the CDR L2 (SEQ ID No 5) both Leu could be replaced by the conservative substitution such as Ile. Val might be replaced by Ile (less favorable). The first Ser of the loop can be replaced by any residue, while the second might be replaced by another hydrophilic/charged reside. The Tyr residue (54) should not be changed.

| Numbering | 54 | 55 | 56 | 57 | 58 | 59 | 60 | 61 |
|---|---|---|---|---|---|---|---|---|
| Initial sequence | Y | L | V | S | R | L | D | S |
| Suggested mutations | — | L/I | V/i | X | — | L/I | — | S/T/D/N/E/Q |

In the CDR L3 (SEQ ID No 6) there is no restriction on sequence nor length of the loop as long as it adopts canonical structure L3-kappa1 as defined in Al-Lazikani et al (cited supra).

| Numbering | 94 | 95 | 96 | 97 | 98 | 99 | 100 | 101 | 102 |
|---|---|---|---|---|---|---|---|---|---|
| Initial sequence | W | Q | G | S | H | F | P | R | T |
| Suggested mutations | X | X | X | X | X | X | X | X | X |

Around the CDR H1 (SEQ ID No 1) GYTFTAYY) the first Thr of the loop (Thr 28) is a potential position for affinity maturation.

| Numbering | 26 | 27 | 28 | 29 | 30 | 31 | 32 | 33 |
|---|---|---|---|---|---|---|---|---|
| Initial sequence | G | Y | T | F | T | A | Y | Y |
| Suggested mutations | — | — | Special | — | — | — | — | — |

In the CDR H2 (SEQ ID No 2) the Phe and Tyr can be replaced by any aromatic residue (F/Y/W).

| Numbering | 52 | 53 | 54 | 55 | 56 | 57 |
|---|---|---|---|---|---|---|
| Initial sequence | N | P | Y | N | G | F |
| Suggested mutations | — | — | Y/F/W | — | — | F/Y/W |

As for the CDR H3 (EFYGYRYFDV) no change should be made to this loop.

| Numbering | 99 | 100 | 101 | 102 | 103 | 104 | 105 | 106 | 107 | 108 |
|---|---|---|---|---|---|---|---|---|---|---|
| Initial sequence | E | F | Y | G | Y | R | Y | F | D | V |
| Suggested mutations | — | — | — | — | — | — | — | — | — | — |

Ephrin Binding Site

The hu2H11 antibody shows functional activity: it inhibits ephrin-A1 binding and ephrin-A1 induced phosphorylation of EphA2. The structure of the LBD and CRD domains of the EphA2 receptor in complex with ephrinA1 has been published (PDB code 3 MBW). When superimposing this structure on that of EphA2 in complex with the Fab fragment of hu2H11R35R74, it clearly appears that the light chain of the Fab fragment of 2H11R35R74 overlaps with the binding area of ephrin-A1 on EphA2 and hence confirms the competitive nature of the hu2H11 antibody.

Example 12

Inhibition of Growth of EphA2 Expressing Tumor Cells by Humanized 2H11R35R74-DM4 Conjugates MDA-MB231 cells in exponential phase of growth were trypsinized and resuspended in culture medium (DMEM/F12 Gibco #21331; 10% SVF Gibco #10500-056; 2 nM Glutamine Gibco #). Cell suspension was distributed in 96-well Cytostar culture plates (GE Healthcare Europe, #RPNQ0163) in complete serum-containing media at a density of 5000 cells/well After coating for 4 hours, serial dilutions of conjugates were added to triplicate wells at concentrations ranging between $10^{-7}$ and $10^{-12}$ M. Cells were cultured at 37° C./5% CO2 in the presence of the antibody-cytotoxic compound conjugates for 3 days. The 4th day, 10 μl of a solution of 14C thymidine (0.1 μCi/well (Perkin Elmer #NEC56825000) was added to each well. The uptake of 14C thymidine was measured 96 hours after the experiment has been started with a microbeta radioactive counter (Perkin Elmer). Cell-free reagent blanks were substracted from the test well readings and the data were plotted as surviving fractions obtained by dividing readings of the conjugate-treated cells by the average of readings from control wells of vehicle-treated cells. In some experiments, the naked antibody (2H11 or 2H11R35R74) was added to the wells at a concentration of 1 μM at the beginning of the experiment, and inhibition of proliferation was measured as previously described.

Results

Results reported in table IX suggest that all 2H11R35R74 DM4 conjugates tested are as potent as the hu2H11R35R74-Peg-4-AcNH-DM4 in inhibiting the growth of MDA-MB231 cells.

Example 13

Evaluation of Different Linkers on the Anti-Tumor Activity of 2h11-DM4 Conjugates Against Colon Adenocarcinoma Lovo in SCID Female Mice Materials and Methods For the evaluation of anti-tumor activity of conjugates, animals were weighed daily and tumors were measured 2 times weekly by caliper. Tumor weights were calculated using the formula mass (mg)=[length (mm)×width (mm)$^2$]/2. Antitumor activity evaluation was done at the highest non toxic dose (HNTD).

A dosage producing a 20% body weight loss (bwl) at nadir (mean of group) or 10% or more drug deaths, was considered an excessively toxic dosage. Animal body weights included the tumor weights. The primary efficacy end points are ΔT/ΔC, percent median regression, partial and complete regressions (PR and CR) and Tumor free survivors (TFS).

Changes in tumor volume for each treated (T) and control (C) are calculated for each tumor by subtracting the tumor volume on the day of first treatment (staging day) from the tumor volume on the specified observation day. The median ΔT is calculated for the treated group and the median ΔC is calculated for the control group. Then the ratio ΔT/ΔC is calculated and expressed as a percentage:

$$\% \ \Delta T / \Delta C = \frac{\text{median}(Tt - T0)}{\text{median}(t - C0)} \times 100$$

The dose is considered as therapeutically active when ΔT/ΔC is lower than 40% and very active when ΔT/ΔC is lower than 10%. If ΔT/ΔC is lower than 0, the dose is considered as highly active and the percentage of regression is dated (ref 1):

% tumor regression: is defined as the % of tumor volume decrease in the treated group at a specified observation day compared to its volume on the first day of first treatment.

At a specific time point and for each animal, % regression is calculated. The median % regression is then calculated for the group.

$$\% \text{ regression (at } t) = \frac{volume_{t0} - volume_t}{volume_{t0}} \times 100$$

Partial regression (PR): Regressions are defined as partial if the tumor volume decreases to 50% of the tumor volume at the start of treatment.

Complete regression (CR): Complete regression is achieved when tumor volume=0 mm$^3$ (CR is considered when tumor volume cannot be recorded).

TFS: Tumor free is defined as the animals with undetectable tumors at the end of the study (>100 days post last treatment)

Results

The antitumor activity of antibody drug 2h11-DM4 conjugates with different non cleavable linkers hu2H11-R35R74-PEG4-AcNH-DM4, hu2H11-R35R74-PEG8-AcNH-DM4, hu2H11-R35R74-PEG4-AcNMe-DM4, hu2H11-R35R74-PEG4-Allyl-DM4 and hu2H11-R35R74-Acetyl-DM4 was evaluated comparing the same dose of 600 μg of DM4/kg on Colon Lovo tumors S.C. implanted in female SCID. Control group was left untreated. Doses were expressed in microgram of DM4 per kilogram. The conjugates were administered by an intravenous (IV) bolus injection, on day 14.

As illustrated in Table X using a single administration schedule, all five conjugate exhibited the same high activity on Lovo tumor model with a ΔT/ΔC<0 and the same impact on the body weight loss (−13.3% in the control group versus −9.5% to 11.2% for treated groups). The hu2H11-R35R74-PEG4-AcNH-DM4 exhibited the best efficacy with a tumor regression of 82% and 1 CR compared to tumor regressions of 72%, 69%, 41% and 33% without CR for hu2H11-R35R74-PEG4-AcNMe-DM4, hu2H11-R35R74-Acetyl-DM4, hu2H11-R35R74-PEG4-Allyl-DM4 and hu2H11-R35R74-PEG8-AcNH-DM4, respectively.

Tables

TABLE I

Biacore analysis of the binding of hu2H11R35R74 and conjugates thereof to EphA2
Binding to huEphA2-mFc (133RU)/Biacore kinetic data

| huEphA2 antibody | D/A | $K_a$ ($K_{on}$) ($M^{-1}s^{-1}$) | $K_d$ ($K_{off}$) ($s^{-1}$) | $K_A$ ($M^{-1}$) | $K_D$ (M) | STDEV | Ratio |
|---|---|---|---|---|---|---|---|
| hu2H11 | 0 | 3.71E+06 | 1.10E−03 | 3.39E+09 | 2.98E−10 | 3.61E−11 | 1.0 |
| hu2H11R35R74 | 0 | 5.25E+06 | 1.15E−03 | 4.59E+09 | 2.18E−10 | 1.13E−11 | 0.7 |
| hu2H11R35R74- | 5.6 | 4.35E+06 | 1.15E−03 | 3.80E+09 | 2.63E−10 | *** | 0.9 |

TABLE I-continued

Biacore analysis of the binding of hu2H11R35R74 and conjugates thereof to EphA2
Binding to huEphA2-mFc (133RU)/Biacore kinetic data

| huEphA2 antibody | D/A | $K_a$ ($K_{on}$) ($M^{-1}s^{-1}$) | $K_d$ ($K_{off}$) ($s^{-1}$) | $K_A$ ($M^{-1}$) | $K_D$ (M) | STDEV | Ratio |
|---|---|---|---|---|---|---|---|
| PEG4-NHAc-DM4 | | | | | | | |
| hu2H11R35R74-PEG4-NHAc-DM4 | 6.3 | 4.21E+06 | 1.19E−03 | 3.55E+09 | 2.82E−10 | *** | 0.9 |
| hu2H11R35R74-PEG4-NHAc-DM4 | 7.4 | 4.47E+06 | 1.23E−03 | 3.64E+09 | 2.75E−10 | *** | 0.9 |
| hu2H11R35R74-PEG4-NHAc-DM4 | 8.4 | 4.15E+06 | 1.11E−03 | 3.76E+09 | 2.66E−10 | *** | 0.9 |
| hu2H11R35R74-PEG4-NHAc-DM4 | 9.3 | 3.08E+06 | 1.29E−03 | 2.38E+09 | 4.21E−10 | *** | 1.4 |
| hu2H11-PEG4-NHAc-DM4 | 7.5 | 1.49E+06 | 2.42E−03 | 6.16E+08 | 1.62E−09 | *** | 5.4 |

TABLE II

Cytotoxic activity of hu2H11R35R74-PEG4-Mal-DM4 on Lovo cells

| Conjugate | DAR | $IC_{50}$ (M) |
|---|---|---|
| hu2H11-PEG4-Mal-DM4 | 6.99 | 1.22E-10 |
| hu2H11R35R74-PEG4-Mal-DM4 | 6.70 | 7.96E-11 |
| hu2H11R35R74-PEG4-Mal-DM4 | 7.00 | 1.16E-11 |

TABLE III

Cytotoxicity of hu2H11R35R74 and conjugates thereof on MDA MB231 cells and SKMEL-28 cells

| 2H11 ADC | MDA-MB231 IC50 (nM) | MDA-MB231 + naked 2H11 IC50 (nM) | Ratio IC50s | SKMEL28 IC50 (nM) |
|---|---|---|---|---|
| hu2H11-SPDB-DM4 DAR:3.93 | 1.1 | 8.1 | 7 | 8.4 |
| hu2H11R35R74-SPDB-DM4 DAR:3.97 | 1.2 | 11.5 | 9 | 13.1 |
| hu2H11R35R74-PEG4-Mal-DM4 DAR:6.1 | 0.1 | 25.1 | 228 | 51 |
| hu2H11-PEG4-NHAc-DM4 DAR = 5.3 | 0.2 | 27.4 | 114 | 26 |
| hu2H11R35R74-PEG4-NHAc-DM4 DAR = 5.5 | 0.06 | 80.8 | 1346 | 104.4 |

TABLE IV

Pharmacokinetic parameters of conjugates following a single intravenous administration of 20 mg/kg of hu2H11-SPDB-DM4 and hu2H11R35R74-PEG4-NHAc-DM4 in HGS buffer to CD-1 mice.
Intravenous administration

| Compound (DAR) | Detection | C0 [ng/mL] | AUC(0-672 h) [ng · h/mL] | Tlast [hour] | AUC(0-inf) [ng · h/mL] | Extrap [%] | T½ [hour] | CI [L/h/kg] | VdSS [L/kg] |
|---|---|---|---|---|---|---|---|---|---|
| hu2H11R35R74-PEG4-NHAc-DM4 DAR = 5.5 | Total | 530,000 | 69,000,000 | 672 | 73,000,000 | 4.6 | 190 | 0.00027 | 0.068 |
| | Conjugate | 600,000 | 54,000,000 | 672 | 56,000,000 | 3.5 | 150 | 0.00036 | 0.069 |
| hu2H11-SPDB-DM4 DAR = 3.9 | Total | 270,000 | 45,000,000 | 672 | 47,000,000 | 3.2 | 160 | 0.00043 | 0.095 |
| | Conjugate | 360,000 | 28,000,000 | 672 | 28,000,000 | 0.29 | 87 | 0.00070 | 0.080 |

Values are determined from the mean plasma concentrations

TABLE V

Evaluation of the anti-tumor activity of hu2H11-PEG4-NHAc-DM4-conjugate and hu2H11R35R74-PEG4-NHAc-DM4-conjugate against advanced human colon tumor in SCID female mice.

| Agent | Route/ Dosage in mL/kg per injection | Schedule in days | Dosage in mg/kg protein per injection (mg of DM4) | Drug death (Day of death) | Average bwc in % per mouse at nadir (day of nadir) | Median ΔT/ΔC in % day 21 if <0 (% regression) | Regressions PR | Regressions CR | Tumor free survivors day 30 | Bio-statistic p value[a] Day 21 | Comments |
|---|---|---|---|---|---|---|---|---|---|---|---|
| hu2H11R35R74-PEG4-NHAc-DM4 DAR = 5.9 | IV 16 mL/kg | 15 | 40 (1.6) | 0/6 | −14.7 (25) | 28 | 0/6 | 0/6 | 0/6 | 0.011 | Active |
| | | | 10 (0.4) | 0/6 | −18.2 (25) | 39 | 0/6 | 0/6 | 0/6 | 0.0174 | Active |

TABLE V-continued

Evaluation of the anti-tumor activity of hu2H11-PEG4-NHAc-DM4-conjugate and hu2H11R35R74-PEG4-NHAc-DM4-conjugate against advanced human colon tumor in SCID female mice.

| Agent | Route/ Dosage in mL/kg per injection | Sched-ule in days | Dosage in mg/kg protein per injection (mg of DM4) | Drug death (Day of death) | Average bwc in % per mouse at nadir (day of nadir) | Median ΔT/ΔC in % day 21 if <0 (% regression) | Regressions PR | Regressions CR | Tumor free survivors day 30 | Bio-statistic p value$^a$ Day 21 | Comments |
|---|---|---|---|---|---|---|---|---|---|---|---|
| hu2H11-PEG4- | IV | 15 | 44 (1.6) | 0/6 | −13.6 (25) | 26 | 0/6 | 0/6 | 0/6 | 0.0008 | Active |
| NHAc-DM4 | 16 mL/kg | | 11 (0.4) | 0/6 | −15.8 (25) | 76 | 0/6 | 0/6 | 0/6 | NS | Inactive |
| DAR = 5.3 | | | | | | | | | | | |
| Control | — | — | — | 0/8 | −14.7 (27) | — | 0/8 | 0/8 | 0/8 | | |

TABLE VI

Evaluation of the anti-tumor activity of hu2H11R35R74-PEG4-NHAc-DM4 conjugate at different DAR against advanced human prostatic adenocarcinoma PC-3 SCID female mice

| Agent (batch) | Route/ Dosage in ml/kg per injection | Sched-ule in days | Dosage in mg/kg per injection (total dose) | Drug death (Day of death) | Average bwc in % per mouse at nadir (day of nadir) | Median ΔT/ΔC in % day 27 if <0 (% regression) | Regressions PR | Regressions CR | TFS day 34 | Bio-statistic p value$^a$ | Comments |
|---|---|---|---|---|---|---|---|---|---|---|---|
| hu2H11R35R74- | IV | 16 | 10 | 0/8 | −3.4(23) | 20 | 0/8 | 0/8 | 0/8 | NS | Active |
| PEG4-NHAc-DM4 | 16 mL/kg | | 5 | 0/8 | −11.9(30) | 52 | 0/8 | 0/8 | 0/8 | NS | Inactive |
| D/A = 3.4 | | | | | | | | | | | |
| hu2H11R35R74- | IV | 16 | 10 | 0/8 | −4.4(17) | <0(6.8) | 1/8 | 0/8 | 0/8 | 0.0020 | Highly Active |
| PEG4-NHAc-DM4 | 16 mL/kg | | 5 | 0/8 | −4.5(25) | 40 | 0/8 | 0/8 | 0/8 | NS | Inactive |
| D/A = 4.4 | | | | | | | | | | | |
| hu2H11R35R74- | IV | 16 | 10 | 0/8 | −5.3(17) | <0(42.8) | 5/8 | 0/8 | 0/8 | <0.0001 | Highly Active |
| PEG4-NHAc-DM4 | 16 mL/kg | | 5 | 0/8 | −9.3(34) | 3 | 5/8 | 1/8 | 0/8 | 0.0013 | Very Active |
| D/A = 5.9 | | | | | | | | | | | |
| hu2H11R35R74- | IV | 16 | 10 | 0/8 | −5.4(17) | <0(13.4) | 2/8 | 0/8 | 0/8 | <0.0001 | Highly Active |
| PEG4-NHAc-DM4 | 16 mL/kg | | 5 | 0/8 | −8.0(34) | 10 | 2/8 | 0/8 | 0/8 | 0.0043 | Very Active |
| D/A = 6.2 | | | | | | | | | | | |
| hu2H11R35R74- | IV | 16 | 10 | 0/8 | −5.0(17) | <0(66) | 6/8 | 0/8 | 0/8 | <0.0001 | Highly Active |
| PEG4-NHAc-DM4 | 16 mL/kg | | 5 | 0/8 | −6.3(17) | <0(35.5) | 4/8 | 0/8 | 0/8 | <0.0001 | Highly Active |
| D/A = 7.4 | | | | | | | | | | | |
| hu2H11R35R74- | IV | 16 | 10 | 0/8 | −6.3(17) | <0(59.6) | 7/8 | 2/8 | 0/8 | <0.0001 | Highly Active |
| PEG4-NHAc-DM4 | 16 mL/kg | | 5 | 0/8 | −15.6(34) | 8 | 2/8 | 0/8 | 0/8 | 0.0014 | Very Active |
| D/A = 8.4 | | | | | | | | | | | |
| Control | | | | 0/10 | −19.6(27) | 100 | 0/10 | 0/10 | 0/10 | | |

TABLE VIII

Evaluation of the anti-tumor activity of hu2H11R35R74-PEG4-NHAc-DM4 conjugate against advanced human prostatic adenocarcinoma PC-3 SCID female mice.

| Agent (batch) | Route/ Dosage in ml/kg per injection | Sched-ule in days | Dosage in mg/kg per injection (total dose) | Drug death (Day of death) | Average bwc in % per mouse at nadir (day of nadir) | Median ΔT/ΔC in % (day) | Regressions PR | Regressions CR | TFS day 49 | Bio-statistic p value$^a$ D26 | Bio-statistic p value$^a$ D31 | Comments |
|---|---|---|---|---|---|---|---|---|---|---|---|---|
| hu2H11R35R74- | IV | 17 | 160.0 | 1/5(24) | −21.0 (26) | — | — | — | — | | | Toxic |
| PEG4-NHAc-DM4 | 25 mL/kg | | 120.0 | 0/5 | −14.4 (24) | <0 (31) | 5/5 | 1/5 | 0/5 | | <0.0001 | HNTD |
| DAR = 5.9 | | | | | | | | | | | | Highly active |
| | IV | 17 | 80.0 | 0/5 | −10.3 (24) | <0 (31) | 5/5 | 2/5 | 0/5 | | <0.0001 | Highly active |
| | 16 mL/kg | | 40.0 | 0/6 | −6.9 (20) | <0 (31) | 6/6 | 0/6 | 0/6 | | <0.0001 | Highly active |
| | | | 20.0 | 0/6 | −3.7 (49) | <0 (31) | 6/6 | 1/6 | 0/6 | | <0.0001 | Highly active |
| | | | 10.0 | 0/6 | −10.9 (35) | 19 (26) | 1/6 | 0/6 | 0/6 | 0.0002 | | Active |
| | | | 5.0 | 0/6 | −2.8 (33) | 3 (26) | 1/6 | 0/6 | 0/6 | <0.0001 | | Very active |
| | | | 2.5 | 0/6 | −9.4 (33) | 5 (26) | 0/6 | 0/6 | 0/6 | <0.0001 | | Very Active |
| Control | — | — | — | 0/8 | −29.1 (35) | 100 | 1/8 | 0/8 | 0/8 | | | — |

TABLE IX

Cytotoxicity of hu2H11R35R74 and hu2H11R35R74 DM4 conjugates on MDA MB231 cells

| | | IC50 (pM) | | |
|---|---|---|---|---|
| Conjugate | DAR | ADC alone | + naked hu2H11R35R74 | ratio |
| hu2H11-R35R74-PEG4-AcNH-DM4 | 5.9 | 147 | 29731 | 202 |
| hu2H11-R35R74-PEG8-AcNH-DM4 | 4.9 | 400 | 24955 | 62 |
| hu2H11-R35R74-PEG4-Allyl-DM4 | 5.3 | 161 | 7820 | 49 |
| hu2H11-R35R74-PEG4-AcNMe-DM4 | 5.4 | 217 | 36400 | 168 |
| hu2H11-R35R74-Acetyl-DM4 | 6.5 | 185 | 19514 | 105 |

TABLE X

Evaluation of the anti-tumor activity of hu2H11-R35R74-DM4 conjugate with different non cleavable linkers against advanced human colon adenocarcinoma Lovo SCID female mice.

| Agent | Dosage in mL/kg per injection | Dosage in μgof DM4/kg per injection | Schedule in days | Drug death (Day of death) | Average bwc in % per mouse at nadir (day of nadir) | Median ΔT/ΔC in % day 26 | % of regression Day 26 ( median ) | Regressions PR | CR | Comments |
|---|---|---|---|---|---|---|---|---|---|---|
| hu2H11-R35R74-PEG4-AcNH-DM4 | 16 ml/kg | 600 | 14 | 0/6 | −9.5 (23) | <0 | 82 | 5/6 | 1/6 | Highly Active |
| hu2H11-R35R74-PEG8-AcNH-DM4 | 16 ml/kg | 600 | 14 | 0/6 | −11.2 (32) | <0 | 33 | 2/6 | 0/6 | Highly Active |
| hu2H11-R35R74-PEG4-AcNMe-DM4 | 16 ml/kg | 600 | 14 | 0/6 | −8.5 (23) | <0 | 72 | 6/6 | 0/6 | Highly Active |
| hu2H11-R35R74-PEG4-Allyl-DM4 | 16 ml/kg | 600 | 14 | 0/6 | −10.6 (23) | <0 | 41 | 2/6 | 0/6 | Highly Active |
| hu2H11-R35R74-Acetyl-DM4 | 16 ml/kg | 600 | 14 | 0/6 | −10.8 (25) | <0 | 69 | 6/6 | 0/6 | Highly Active |
| Control | — | — | — | 0/10 | −13.3 (30) | — | — | — | — | |

The invention claimed is:

1. An antibody or an epitope-binding fragment thereof that specifically binds to an EphA2 receptor comprising at least one heavy chain and at least one light chain, wherein said heavy chain comprises three sequential complementarity-determining regions comprising the amino acid sequences of SEQ ID NOS: 1, 2, and 3, and wherein said light chain comprises three sequential complementarity-determining regions comprising the amino acid sequences of SEQ ID NOS: 4, 5, and 6.

2. An antibody or an epitope-binding fragment thereof according to claim 1, wherein said monoclonal antibody or epitope-binding fragment thereof is a humanized or resurfaced antibody or epitope-binding fragment thereof.

3. An antibody or an epitope-binding fragment thereof according to claim 1, wherein said heavy chain comprises the amino acid sequence of SEQ ID NO: 12 and wherein said light chain comprises the amino acid sequence, of SEQ ID NO: 14.

4. A conjugate of an antibody or an epitope-binding fragment according to claim 3, wherein said conjugate comprises a cytotoxic agent chosen between:

a) the maytansinoid of formula (XIII):
(XIII)
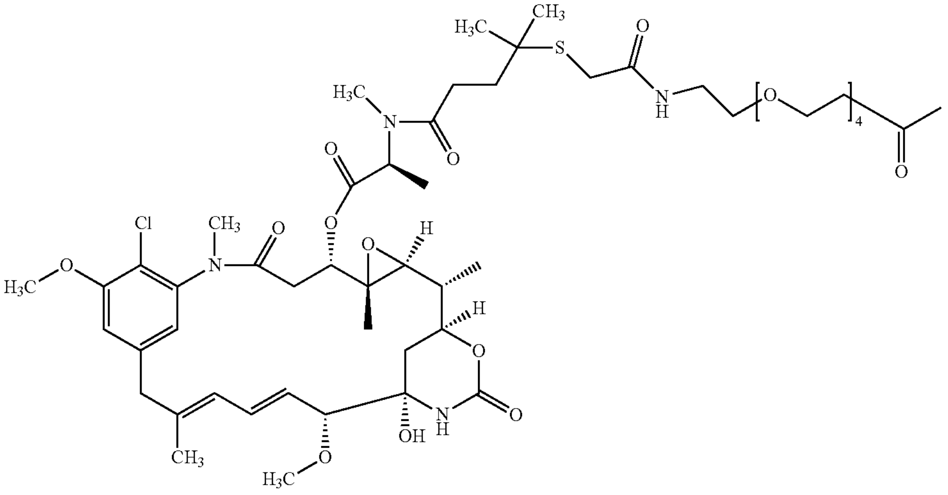
b) the maytansinoid of formula (XIV):
(XIV)
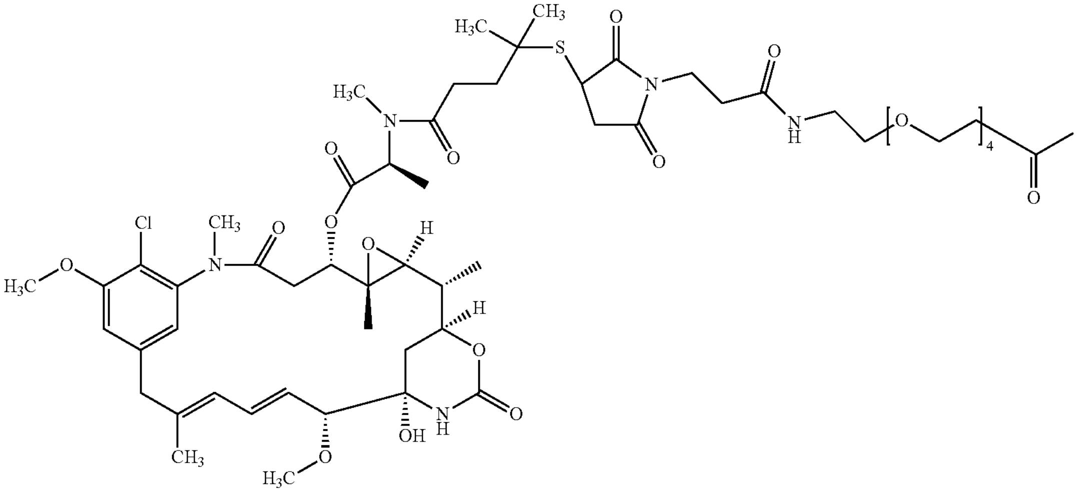
c) the maytansinoid of formula (XXIV):
(XXIV)
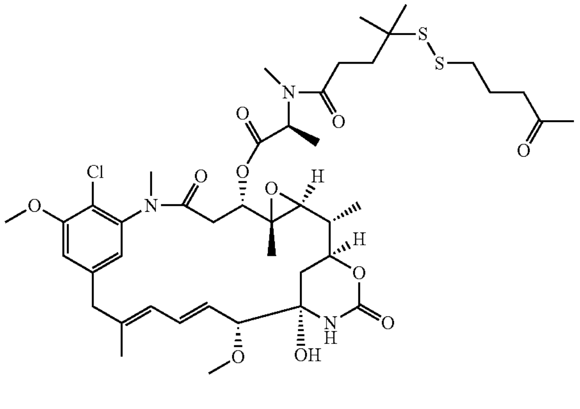

d) the maytansinoid of formula (XXV):
(XXV)
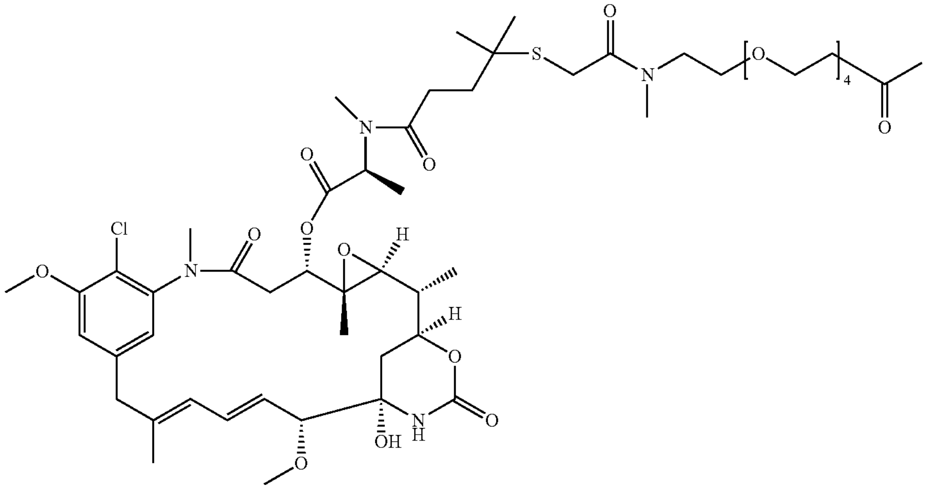
e) the maytansinoid of formula (XXVI):
(XXVI)
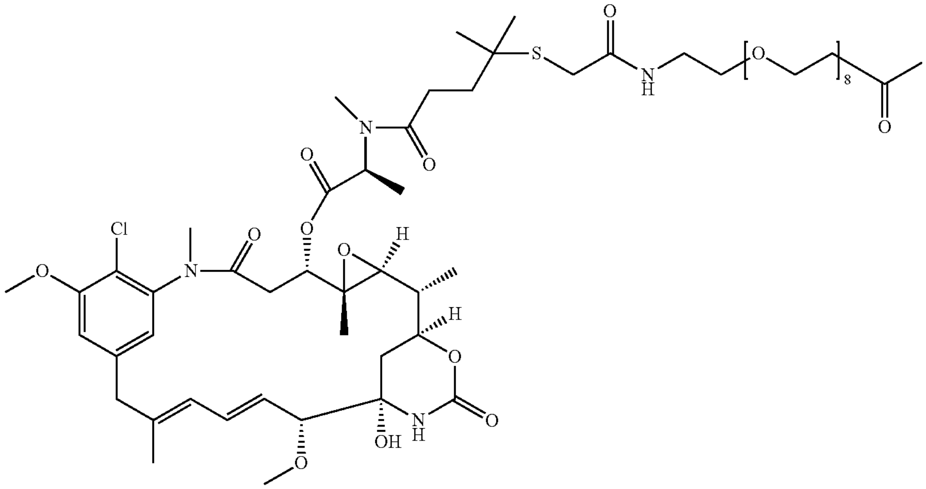
f) the maytansinoid of formula (XXVII):
(XXVII)
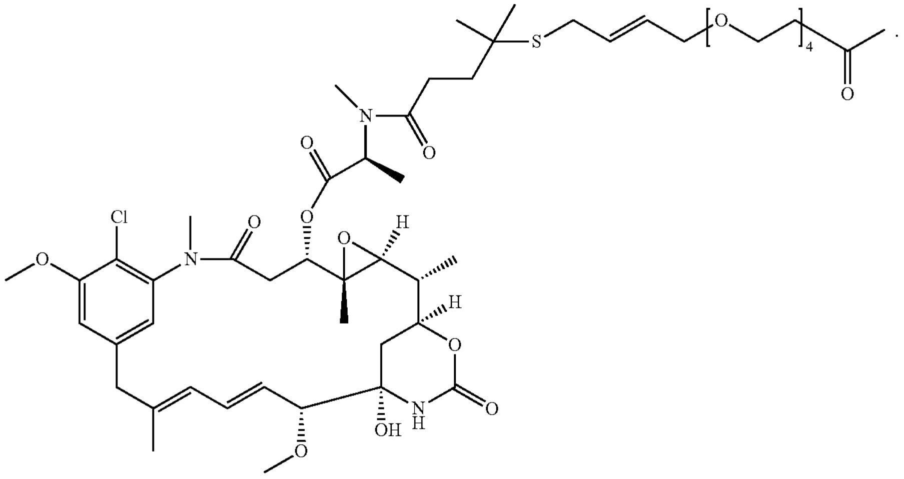

5. A conjugate according to claim 4, wherein said cytotoxic agent is covalently bound to the antibody.

6. A conjugate according to claim 5, wherein the cytotoxic agent is the maytansinoid of formula (XIII).

7. A pharmaceutical composition containing an antibody or epitope-binding fragment thereof according to claim 3, or a conjugate according to claim 6, and a pharmaceutically acceptable carrier or excipient.

8. A conjugate according to claim 6 having an average DAR above 4, the DAR being measured with a UV spectrophotometer and determined by the following equation $$DAR=C_D/C_A$$

With:

$C_D=[(\epsilon_{A280}\times A_{252})-(\epsilon_{A252}\times A_{280})]/[(\epsilon_{D252}\times\epsilon_{A280})-(\epsilon_{A252}\times\epsilon_{D280})]$ $C_A=[A_{280}-(C_D\times\epsilon_{D280})]/\epsilon_{A280}$ $\epsilon_{D252}=26{,}159\ M^{-1}cm^{-1}$ $\epsilon_{D280}=5{,}180\ M^{-1}cm^{-1}$ $\epsilon_{A280}=224{,}000\ M^{-1}cm^{-1}$ $\epsilon_{A252}=82{,}880\ M^{-1}cm^{-1}$ $A_{252}$ and $A_{280}$ being the absorbances of the conjugate measured on the UV spectrophotometer at respectively 252 and 280 nm.

9. A conjugate according to claim 8 having an average DAR comprised between 4 and 10.

10. A conjugate according to claim 9 having an average DAR comprised between 5.9 and 7.5.

11. An article of manufacture comprising:

a) a packaging material b) an antibody or epitope-binding fragment thereof according to claim 3, or a conjugate according to claim 10, and c) a label or package insert contained within said packaging material indicting that said antibody or epitope-binding fragment thereof is effective for treating cancer.

12. An antibody or an epitope-binding fragment thereof according to claim 3, wherein the paratope of said monoclonal antibody or epitope-binding fragment thereof comprises in the light chain: Arg35 of Loop L1, Tyr54, Arg58 and Asp60 of L2.

13. An antibody or an epitope-binding fragment thereof according to claim 3 wherein the paratope of said monoclonal antibody or epitope-binding fragment thereof comprises in the heavy chain: Thr30, Ala31, Tyr32 and Tyr33 of Loop H1, Asn52, Tyr54, Asn55 and Phe57 of H2 and Glu99, Phe100, Tyr101, Gly102, Tyr103 and Tyr105 of H3.

14. An antibody or an epitope-binding fragment thereof according to claim 3, wherein said monoclonal antibody or epitope-binding fragment thereof comprises mutation at the position: Thr H28.

15. An antibody or an epitope-binding fragment thereof according to claim 3, wherein said monoclonal antibody or epitope-binding fragment thereof comprises mutation at one of few of the following positions on the light chain: 35, 26 to 31, 34 to 37, 55, 56, 57, 59 and 94 to 102.

16. An antibody or an epitope-binding fragment thereof according to claim 3, wherein said monoclonal antibody or epitope-binding fragment thereof comprises mutation at one of few of the following positions on the heavy chain: 28, 54 and 57.

17. An antibody or an epitope-binding fragment thereof according to claim 3, which specifically binds to an epitope of human EphA2 receptor comprising residues Gly49, Lys50, Gly51, Asp53, Cys70, Asn71, Val72, Met73, Ser74, Gly75, Gln77, Phe108, Pro109, Gly110, Gly111, Ser113 and Ser114 of the LBD from the extra-cellular domain of EphA2 receptor, or a conservatively substituted form thereof.

18. An antibody or an epitope-binding fragment thereof according to claim 1, wherein said heavy chain comprises the amino acid sequence SEQ ID NO: 18, and wherein said light chain comprises the amino acid sequence SEQ ID NO: 16.

19. A method for preparing a conjugate comprising the steps of:

(i) bringing into contact an optionally-buffered aqueous solution of a cell-binding agent with a solution of a cytotoxic compound;

(ii) then optionally separating the conjugate which was formed in (i) from the unreacted reagents and any aggregate which may be present in the solution;

wherein the cell-binding agent is an antibody according to claim 3, and a cytotoxic agent chosen between:

the compound of formula (XVII):

(XVII)

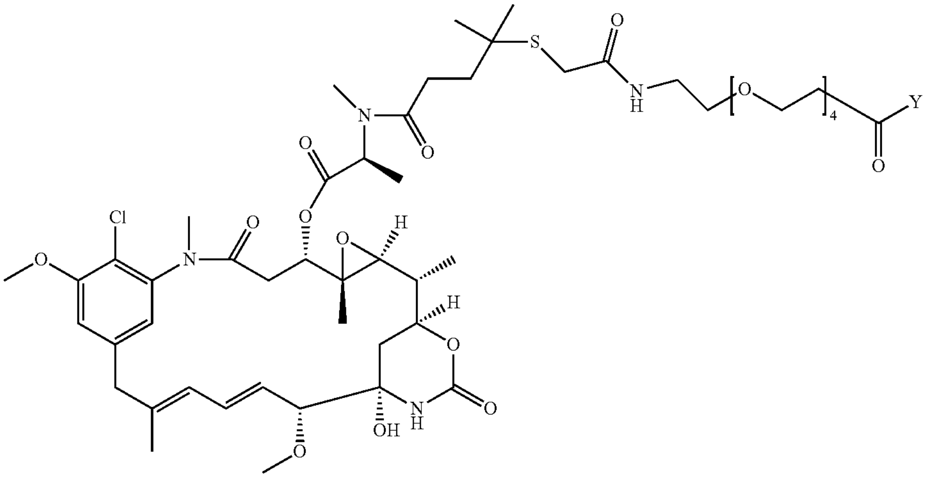

wherein Y is N-succinimidyloxy, N-sulfosuccinimidyloxy, N-phthalimidyloxy, N-sulfophthalimidyloxy, 2-nitrophenyloxy, 4-nitrophenyloxy, 2,4-dinitrophenyloxy, 3-sulfonyl-4-nitrophenyloxy, 3-carboxy-4-nitrophenyloxy, imidazolyl, or halogen atom; and the compound of formula (XVIII):

(XVIII)

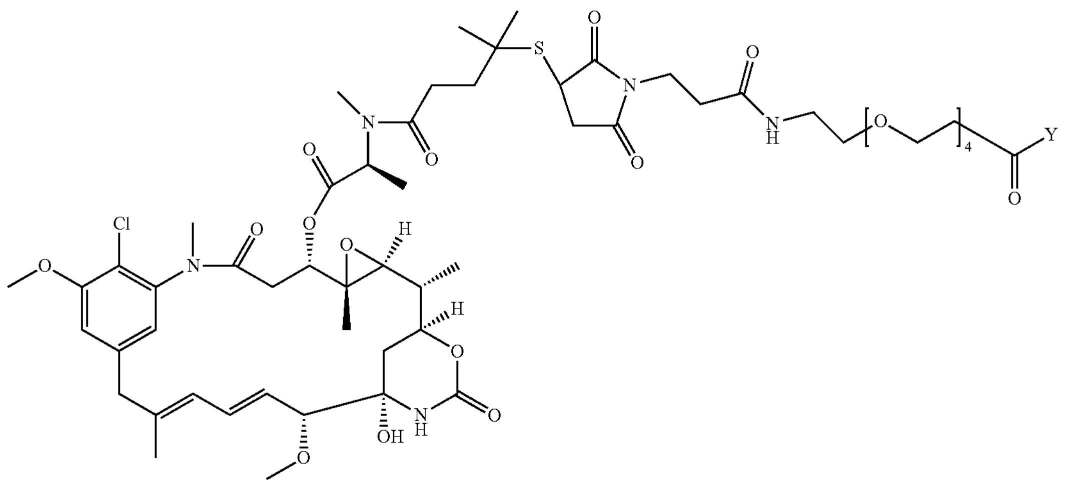

wherein Y is N-succinimidyloxy, N-sulfosuccinimidyloxy, N-phthalimidyloxy, N-sulfophthalimidyloxy, 2-nitrophenyloxy, 4-nitrophenyloxy, 2,4-dinitrophenyloxy, 3-sulfonyl-4-nitrophenyloxy, 3-carboxy-4-nitrophenyloxy, imidazolyl, or halogen atom.

20. A conjugate obtainable by the method of claim 19.

21. A conjugate according to claim 20, said conjugate having a structure chosen between the structures of the formula (XV):

(XV)

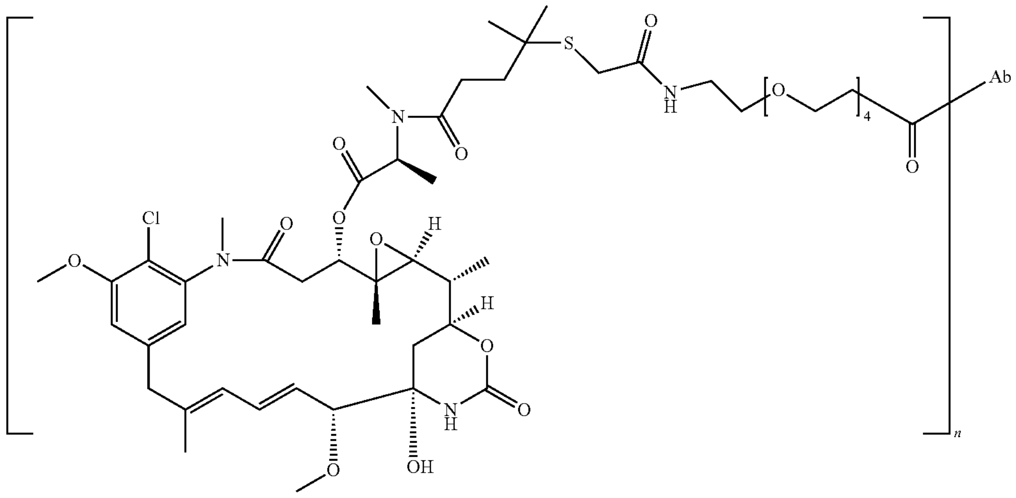

and of the formula (XVI):

(XVI)

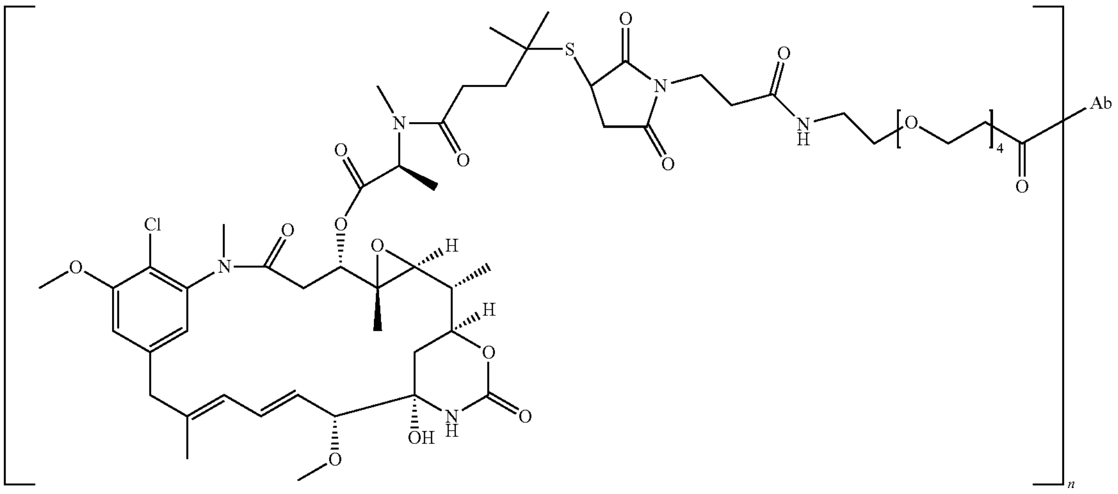

wherein Ab is an antibody according to claim 3 and n is an integer comprised between 1 and 15.

22. The antibody-drug conjugate of claim 21 wherein n is comprised between 4 and 7.

23. The antibody-drug conjugate of claim 22 having the structure of formula (XV).

24. A method for treating cancer comprising administering an antibody or epitope-binding fragment thereof according to claim 3, or a conjugate according to claim 6.

25. The method of claim 24 wherein the cancer is chosen between carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma.

* * * * *

SEQUENCE LISTING

<160> NUMBER OF SEQ ID NOS: 19

<210> SEQ ID NO 1
<211> LENGTH: 5
<212> TYPE: PRT
<213> ORGANISM: Homo sapiens

<400> SEQUENCE: 1

Ala Tyr Tyr Met His
1               5

<210> SEQ ID NO 2
<211> LENGTH: 17
<212> TYPE: PRT
<213> ORGANISM: Mus musculus

<400> SEQUENCE: 2

Leu Val Asn Pro Tyr Asn Gly Phe Ser Ser Tyr Asn Gln Lys Phe Gln
1               5                   10                  15

Gly

<210> SEQ ID NO 3
<211> LENGTH: 10
<212> TYPE: PRT
<213> ORGANISM: Mus musculus

<400> SEQUENCE: 3

Glu Phe Tyr Gly Tyr Arg Tyr Phe Asp Val

```
1               5                   10


<210> SEQ ID NO 4
<211> LENGTH: 16
<212> TYPE: PRT
<213> ORGANISM: Mus musculus

<400> SEQUENCE: 4

Lys Ser Ser Gln Ser Leu Ile His Ser Asp Gly Arg Thr Tyr Leu Asn
1               5                   10                  15


<210> SEQ ID NO 5
<211> LENGTH: 7
<212> TYPE: PRT
<213> ORGANISM: Mus musculus

<400> SEQUENCE: 5

Leu Val Ser Arg Leu Asp Ser
1               5


<210> SEQ ID NO 6
<211> LENGTH: 9
<212> TYPE: PRT
<213> ORGANISM: Mus musculus

<400> SEQUENCE: 6

Trp Gln Gly Ser His Phe Pro Arg Thr
1               5


<210> SEQ ID NO 7
<211> LENGTH: 357
<212> TYPE: DNA
<213> ORGANISM: Mus musculus
<220> FEATURE:
<221> NAME/KEY: CDS
<222> LOCATION: (1)..(357)

<400> SEQUENCE: 7

gag gtc cag ctg caa cag tct gga cct gag ctg gtg aag cct ggg gct       48
Glu Val Gln Leu Gln Gln Ser Gly Pro Glu Leu Val Lys Pro Gly Ala
1               5                   10                  15

tca gtg aag att tcc tgc aag gct tct ggt tac tca ttc act gcc tac       96
Ser Val Lys Ile Ser Cys Lys Ala Ser Gly Tyr Ser Phe Thr Ala Tyr
            20                  25                  30

tac atg cac tgg gtg aag caa agt cat gta aag agt ctt gag tgg att      144
Tyr Met His Trp Val Lys Gln Ser His Val Lys Ser Leu Glu Trp Ile
        35                  40                  45

gga ctt gtt aat cct tac aat ggt ttt agt agc tac aac cag aat ttc      192
Gly Leu Val Asn Pro Tyr Asn Gly Phe Ser Ser Tyr Asn Gln Asn Phe
    50                  55                  60

gag gac aag gcc agc ttg act gta gat aga ttc tcc agc acc gcc tac      240
Glu Asp Lys Ala Ser Leu Thr Val Asp Arg Phe Ser Ser Thr Ala Tyr
65                  70                  75                  80

atg gaa ctc cac agc ctg aca tct gag gac tct gca gtc tat tac tgt      288
Met Glu Leu His Ser Leu Thr Ser Glu Asp Ser Ala Val Tyr Tyr Cys
                85                  90                  95

gca aga gaa ttc tac ggc tac cgg tac ttc gat gtc tgg ggc gca ggg      336
Ala Arg Glu Phe Tyr Gly Tyr Arg Tyr Phe Asp Val Trp Gly Ala Gly
            100                 105                 110

acc gcg gtc acc gtc tcc tca                                          357
Thr Ala Val Thr Val Ser Ser
        115


<210> SEQ ID NO 8
```

<211> LENGTH: 119
<212> TYPE: PRT
<213> ORGANISM: Mus musculus

<400> SEQUENCE: 8

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ala Tyr
            20                  25                  30

Tyr Met His Trp Val Lys Gln Ser His Val Lys Ser Leu Glu Trp Ile
        35                  40                  45

Gly Leu Val Asn Pro Tyr Asn Gly Phe Ser Ser Tyr Asn Gln Asn Phe
    50                  55                  60

Glu Asp Lys Ala Ser Leu Thr Val Asp Arg Phe Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Glu Phe Tyr Gly Tyr Arg Tyr Phe Asp Val Trp Gly Ala Gly
            100                 105                 110

Thr Ala Val Thr Val Ser Ser
        115
```

<210> SEQ ID NO 9
<211> LENGTH: 339
<212> TYPE: DNA
<213> ORGANISM: Mus musculus
<220> FEATURE:
<221> NAME/KEY: CDS
<222> LOCATION: (1)..(339)

<400> SEQUENCE: 9

```
gat gtt gtg atg acc cag act cca ctc act ttg tcg gtt acc att gga       48
Asp Val Val Met Thr Gln Thr Pro Leu Thr Leu Ser Val Thr Ile Gly
1               5                   10                  15

caa cca gcc tcc atc tct tgc aag tca agt cag agc ctc ata cat agt       96
Gln Pro Ala Ser Ile Ser Cys Lys Ser Ser Gln Ser Leu Ile His Ser
            20                  25                  30

gat gga aga aca tat ttg aat tgg ttg tta cag agg cca ggc cag tct      144
Asp Gly Arg Thr Tyr Leu Asn Trp Leu Leu Gln Arg Pro Gly Gln Ser
        35                  40                  45

cca aag cgc cta att tat ctg gtg tct aga ctg gac tct gga gtc cct      192
Pro Lys Arg Leu Ile Tyr Leu Val Ser Arg Leu Asp Ser Gly Val Pro
    50                  55                  60

gac agg ttc act ggc agt gga tca ggg aca gat ttc aca ctg aaa atc      240
Asp Arg Phe Thr Gly Ser Gly Ser Gly Thr Asp Phe Thr Leu Lys Ile
65                  70                  75                  80

agc aga gtg gag gct gag gat ttg gga gtt tat tat tgc tgg caa ggt      288
Ser Arg Val Glu Ala Glu Asp Leu Gly Val Tyr Tyr Cys Trp Gln Gly
                85                  90                  95

tca cat ttt cct cgg acg ttc ggt gga ggc acc aag ctg gaa atc aaa      336
Ser His Phe Pro Arg Thr Phe Gly Gly Gly Thr Lys Leu Glu Ile Lys
            100                 105                 110

cgg                                                                  339
Arg
```

<210> SEQ ID NO 10
<211> LENGTH: 113
<212> TYPE: PRT
<213> ORGANISM: Mus musculus

<400> SEQUENCE: 10

Asp Val Val Met Thr Gln Thr Pro Leu Thr Leu Ser Val Thr Ile Gly
1 5 10 15

Gln Pro Ala Ser Ile Ser Cys Lys Ser Ser Gln Ser Leu Ile His Ser
20 25 30

Asp Gly Arg Thr Tyr Leu Asn Trp Leu Leu Gln Arg Pro Gly Gln Ser
35 40 45

Pro Lys Arg Leu Ile Tyr Leu Val Ser Arg Leu Asp Ser Gly Val Pro
50 55 60

Asp Arg Phe Thr Gly Ser Gly Ser Gly Thr Asp Phe Thr Leu Lys Ile
65 70 75 80

Ser Arg Val Glu Ala Glu Asp Leu Gly Val Tyr Tyr Cys Trp Gln Gly
85 90 95

Ser His Phe Pro Arg Thr Phe Gly Gly Gly Thr Lys Leu Glu Ile Lys
100 105 110

Arg

<210> SEQ ID NO 11
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 11 cag gtg caa ctg gtg caa tcc ggt gcc gag gtc gtc aaa ccc gga gca 48
Gln Val Gln Leu Val Gln Ser Gly Ala Glu Val Val Lys Pro Gly Ala
1 5 10 15 tct gtg aag ata tcc tgt aag gcc tcc ggc tac act ttt aca gcc tac 96
Ser Val Lys Ile Ser Cys Lys Ala Ser Gly Tyr Thr Phe Thr Ala Tyr
20 25 30 tat atg cat tgg gtt aaa cag agt ccc gtg cag tcc ctg gaa tgg atc 144
Tyr Met His Trp Val Lys Gln Ser Pro Val Gln Ser Leu Glu Trp Ile
35 40 45 ggc ttg gtg aac cct tat aac gga ttc tca agt tac aat caa aag ttt 192
Gly Leu Val Asn Pro Tyr Asn Gly Phe Ser Ser Tyr Asn Gln Lys Phe
50 55 60 cag ggc aag gct tcc ctg act gta gac aga tct agt tcc aca gcc tac 240
Gln Gly Lys Ala Ser Leu Thr Val Asp Arg Ser Ser Ser Thr Ala Tyr
65 70 75 80 atg gag ctc cat tca ctg aca tca gaa gac agc gcc gta tac tat tgc 288
Met Glu Leu His Ser Leu Thr Ser Glu Asp Ser Ala Val Tyr Tyr Cys
85 90 95 gca cgt gag ttc tac ggc tat aga tac ttt gac gtc tgg ggc caa ggc 336
Ala Arg Glu Phe Tyr Gly Tyr Arg Tyr Phe Asp Val Trp Gly Gln Gly
100 105 110 aca gcc gtc aca gtg agc tct 357
Thr Ala Val Thr Val Ser Ser
115

<210> SEQ ID NO 12
<211> LENGTH: 119
<212> TYPE: PRT
<213> ORGANISM: Homo sapiens

<400> SEQUENCE: 12

Gln Val Gln Leu Val Gln Ser Gly Ala Glu Val Val Lys Pro Gly Ala
1 5 10 15

Ser Val Lys Ile Ser Cys Lys Ala Ser Gly Tyr Thr Phe Thr Ala Tyr
20 25 30

```
Tyr Met His Trp Val Lys Gln Ser Pro Val Gln Ser Leu Glu Trp Ile
        35                  40                  45

Gly Leu Val Asn Pro Tyr Asn Gly Phe Ser Ser Tyr Asn Gln Lys Phe
    50                  55                  60

Gln Gly Lys Ala Ser Leu Thr Val Asp Arg Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Glu Phe Tyr Gly Tyr Arg Tyr Phe Asp Val Trp Gly Gln Gly
            100                 105                 110

Thr Ala Val Thr Val Ser Ser
        115


<210> SEQ ID NO 13
<211> LENGTH: 336
<212> TYPE: DNA
<213> ORGANISM: Homo sapiens
<220> FEATURE:
<221> NAME/KEY: CDS
<222> LOCATION: (1)..(336)

<400> SEQUENCE: 13

gac gtc gtg atg aca caa acc cct ctg tcc ctg agc gtc act ctg gga       48
Asp Val Val Met Thr Gln Thr Pro Leu Ser Leu Ser Val Thr Leu Gly
1               5                   10                  15

caa ccc gct tcc att agc tgc aaa tca tca caa tct ctc atc cac tca       96
Gln Pro Ala Ser Ile Ser Cys Lys Ser Ser Gln Ser Leu Ile His Ser
            20                  25                  30

gac ggc cgt acg tac ctc aat tgg ctg ctg cag aga cca gga cag tcc      144
Asp Gly Arg Thr Tyr Leu Asn Trp Leu Leu Gln Arg Pro Gly Gln Ser
        35                  40                  45

cct aaa agg ctt atc tac ctg gtc tct cgt ttg gac tct ggt gta cca      192
Pro Lys Arg Leu Ile Tyr Leu Val Ser Arg Leu Asp Ser Gly Val Pro
    50                  55                  60

gac cgg ttt act ggt tcc ggg gcc gga acc gat ttc act ctg aag att      240
Asp Arg Phe Thr Gly Ser Gly Ala Gly Thr Asp Phe Thr Leu Lys Ile
65                  70                  75                  80

tcc agg gtg gaa gct gaa gat ctc gga gtg tat tat tgc tgg cag ggc      288
Ser Arg Val Glu Ala Glu Asp Leu Gly Val Tyr Tyr Cys Trp Gln Gly
                85                  90                  95

agc cat ttc ccc cgt act ttt ggt ggg ggt acc aaa ttg gaa att aag      336
Ser His Phe Pro Arg Thr Phe Gly Gly Gly Thr Lys Leu Glu Ile Lys
            100                 105                 110


<210> SEQ ID NO 14
<211> LENGTH: 112
<212> TYPE: PRT
<213> ORGANISM: Homo sapiens

<400> SEQUENCE: 14

Asp Val Val Met Thr Gln Thr Pro Leu Ser Leu Ser Val Thr Leu Gly
1               5                   10                  15

Gln Pro Ala Ser Ile Ser Cys Lys Ser Ser Gln Ser Leu Ile His Ser
            20                  25                  30

Asp Gly Arg Thr Tyr Leu Asn Trp Leu Leu Gln Arg Pro Gly Gln Ser
        35                  40                  45

Pro Lys Arg Leu Ile Tyr Leu Val Ser Arg Leu Asp Ser Gly Val Pro
    50                  55                  60

Asp Arg Phe Thr Gly Ser Gly Ala Gly Thr Asp Phe Thr Leu Lys Ile
65                  70                  75                  80
```

```
Ser Arg Val Glu Ala Glu Asp Leu Gly Val Tyr Tyr Cys Trp Gln Gly
                85                  90                  95

Ser His Phe Pro Arg Thr Phe Gly Gly Gly Thr Lys Leu Glu Ile Lys
            100                 105                 110


<210> SEQ ID NO 15
<211> LENGTH: 717
<212> TYPE: DNA
<213> ORGANISM: Homo sapiens
<220> FEATURE:
<221> NAME/KEY: CDS
<222> LOCATION: (1)..(717)

<400> SEQUENCE: 15

atg gga tgg tct tgc atc atc ctg ttt ctc gtg gct act gcc acc gga       48
Met Gly Trp Ser Cys Ile Ile Leu Phe Leu Val Ala Thr Ala Thr Gly
1               5                   10                  15

gtg cac agt gac gtc gtg atg aca caa acc cct ctg tcc ctg agc gtc       96
Val His Ser Asp Val Val Met Thr Gln Thr Pro Leu Ser Leu Ser Val
            20                  25                  30

act ctg gga caa ccc gct tcc att agc tgc aaa tca tca caa tct ctc      144
Thr Leu Gly Gln Pro Ala Ser Ile Ser Cys Lys Ser Ser Gln Ser Leu
        35                  40                  45

atc cac tca gac ggc cgt acg tac ctc aat tgg ctg ctg cag aga cca      192
Ile His Ser Asp Gly Arg Thr Tyr Leu Asn Trp Leu Leu Gln Arg Pro
    50                  55                  60

gga cag tcc cct aaa agg ctt atc tac ctg gtc tct cgt ttg gac tct      240
Gly Gln Ser Pro Lys Arg Leu Ile Tyr Leu Val Ser Arg Leu Asp Ser
65                  70                  75                  80

ggt gta cca gac cgg ttt act ggt tcc ggg gcc gga acc gat ttc act      288
Gly Val Pro Asp Arg Phe Thr Gly Ser Gly Ala Gly Thr Asp Phe Thr
                85                  90                  95

ctg aag att tcc agg gtg gaa gct gaa gat ctc gga gtg tat tat tgc      336
Leu Lys Ile Ser Arg Val Glu Ala Glu Asp Leu Gly Val Tyr Tyr Cys
            100                 105                 110

tgg cag ggc agc cat ttc ccc cgt act ttt ggt ggg ggt acc aaa ttg      384
Trp Gln Gly Ser His Phe Pro Arg Thr Phe Gly Gly Gly Thr Lys Leu
        115                 120                 125

gaa att aag cgt acg gtg gct gca cca tct gtc ttc atc ttc ccg cca      432
Glu Ile Lys Arg Thr Val Ala Ala Pro Ser Val Phe Ile Phe Pro Pro
    130                 135                 140

tct gat gag cag ttg aaa tct gga act gcc tct gtt gtg tgc ctg ctg      480
Ser Asp Glu Gln Leu Lys Ser Gly Thr Ala Ser Val Val Cys Leu Leu
145                 150                 155                 160

aat aac ttc tat ccc aga gag gcc aaa gta cag tgg aag gtg gat aac      528
Asn Asn Phe Tyr Pro Arg Glu Ala Lys Val Gln Trp Lys Val Asp Asn
                165                 170                 175

gcc ctc caa tcg ggt aac tcc cag gag agt gtc aca gag cag gac agc      576
Ala Leu Gln Ser Gly Asn Ser Gln Glu Ser Val Thr Glu Gln Asp Ser
            180                 185                 190

aag gac agc acc tac agc ctc agc agc acc ctg acg ctg agc aaa gca      624
Lys Asp Ser Thr Tyr Ser Leu Ser Ser Thr Leu Thr Leu Ser Lys Ala
        195                 200                 205

gac tac gag aaa cac aaa gtc tac gcc tgc gaa gtc acc cat cag ggc      672
Asp Tyr Glu Lys His Lys Val Tyr Ala Cys Glu Val Thr His Gln Gly
    210                 215                 220

ctg agc tcg ccc gtc aca aag agc ttc aac agg gga gag tgt tag          717
Leu Ser Ser Pro Val Thr Lys Ser Phe Asn Arg Gly Glu Cys
225                 230                 235


<210> SEQ ID NO 16
<211> LENGTH: 238
```

<212> TYPE: PRT
<213> ORGANISM: Homo sapiens

<400> SEQUENCE: 16

```
Met Gly Trp Ser Cys Ile Ile Leu Phe Leu Val Ala Thr Ala Thr Gly
1               5                   10                  15

Val His Ser Asp Val Val Met Thr Gln Thr Pro Leu Ser Leu Ser Val
            20                  25                  30

Thr Leu Gly Gln Pro Ala Ser Ile Ser Cys Lys Ser Ser Gln Ser Leu
        35                  40                  45

Ile His Ser Asp Gly Arg Thr Tyr Leu Asn Trp Leu Leu Gln Arg Pro
    50                  55                  60

Gly Gln Ser Pro Lys Arg Leu Ile Tyr Leu Val Ser Arg Leu Asp Ser
65                  70                  75                  80

Gly Val Pro Asp Arg Phe Thr Gly Ser Gly Ala Gly Thr Asp Phe Thr
                85                  90                  95

Leu Lys Ile Ser Arg Val Glu Ala Glu Asp Leu Gly Val Tyr Tyr Cys
            100                 105                 110

Trp Gln Gly Ser His Phe Pro Arg Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 17
<211> LENGTH: 1404
<212> TYPE: DNA
<213> ORGANISM: Homo sapiens
<220> FEATURE:
<221> NAME/KEY: CDS
<222> LOCATION: (1)..(1404)

<400> SEQUENCE: 17

```
atg gga tgg tcc tgt att att ctg ttt ctc gtg gct aca gcc aca ggc       48
Met Gly Trp Ser Cys Ile Ile Leu Phe Leu Val Ala Thr Ala Thr Gly
1               5                   10                  15

gtt cat agt cag gtg caa ctg gtg caa tcc ggt gcc gag gtc gtc aaa       96
Val His Ser Gln Val Gln Leu Val Gln Ser Gly Ala Glu Val Val Lys
            20                  25                  30

ccc gga gca tct gtg aag ata tcc tgt aag gcc tcc ggc tac act ttt      144
Pro Gly Ala Ser Val Lys Ile Ser Cys Lys Ala Ser Gly Tyr Thr Phe
        35                  40                  45

aca gcc tac tat atg cat tgg gtt aaa cag agt ccc gtg cag tcc ctg      192
Thr Ala Tyr Tyr Met His Trp Val Lys Gln Ser Pro Val Gln Ser Leu
    50                  55                  60

gaa tgg atc ggc ttg gtg aac cct tat aac gga ttc tca agt tac aat      240
Glu Trp Ile Gly Leu Val Asn Pro Tyr Asn Gly Phe Ser Ser Tyr Asn
65                  70                  75                  80
```

-continued

```
caa aag ttt cag ggc aag gct tcc ctg act gta gac aga tct agt tcc      288
Gln Lys Phe Gln Gly Lys Ala Ser Leu Thr Val Asp Arg Ser Ser Ser
                85                  90                  95

aca gcc tac atg gag ctc cat tca ctg aca tca gaa gac agc gcc gta      336
Thr Ala Tyr Met Glu Leu His Ser Leu Thr Ser Glu Asp Ser Ala Val
            100                 105                 110

tac tat tgc gca cgt gag ttc tac ggc tat aga tac ttt gac gtc tgg      384
Tyr Tyr Cys Ala Arg Glu Phe Tyr Gly Tyr Arg Tyr Phe Asp Val Trp
        115                 120                 125

ggc caa ggc aca gcc gtc aca gtg agc tct gct tcc act aag ggc cca      432
Gly Gln Gly Thr Ala Val Thr Val Ser Ser Ala Ser Thr Lys Gly Pro
    130                 135                 140

tcg gtc ttc ccc ctg gca ccc tcc tcc aag agc acc tct ggg ggc aca      480
Ser Val Phe Pro Leu Ala Pro Ser Ser Lys Ser Thr Ser Gly Gly Thr
145                 150                 155                 160

gcg gcc ctg ggc tgc ctg gtc aag gac tac ttc ccc gaa ccg gtg acg      528
Ala Ala Leu Gly Cys Leu Val Lys Asp Tyr Phe Pro Glu Pro Val Thr
                165                 170                 175

gtg tcg tgg aac tca ggc gcc ctg acc agc ggc gtg cac acc ttc ccg      576
Val Ser Trp Asn Ser Gly Ala Leu Thr Ser Gly Val His Thr Phe Pro
            180                 185                 190

gct gtc cta cag tcc tca gga ctc tac tcc ctc agc agc gtg gtg acc      624
Ala Val Leu Gln Ser Ser Gly Leu Tyr Ser Leu Ser Ser Val Val Thr
        195                 200                 205

gtg ccc tcc agc agc ttg ggc acc cag acc tac atc tgc aac gtg aat      672
Val Pro Ser Ser Ser Leu Gly Thr Gln Thr Tyr Ile Cys Asn Val Asn
    210                 215                 220

cac aag ccc agc aac acc aag gtg gac aag aaa gtt gag ccc aaa tct      720
His Lys Pro Ser Asn Thr Lys Val Asp Lys Lys Val Glu Pro Lys Ser
225                 230                 235                 240

tgt gac aaa act cac aca tgc cca ccg tgc cca gca cct gaa ctc ctg      768
Cys Asp Lys Thr His Thr Cys Pro Pro Cys Pro Ala Pro Glu Leu Leu
                245                 250                 255

ggg gga ccg tca gtc ttc ctc ttc ccc cca aaa ccc aag gac acc ctc      816
Gly Gly Pro Ser Val Phe Leu Phe Pro Pro Lys Pro Lys Asp Thr Leu
            260                 265                 270

atg atc tcc cgg acc cct gag gtc aca tgc gtg gtg gtg gac gtg agc      864
Met Ile Ser Arg Thr Pro Glu Val Thr Cys Val Val Val Asp Val Ser
        275                 280                 285

cac gaa gac cct gag gtc aag ttc aac tgg tac gtg gac ggc gtg gag      912
His Glu Asp Pro Glu Val Lys Phe Asn Trp Tyr Val Asp Gly Val Glu
    290                 295                 300

gtg cat aat gcc aag aca aag ccg cgg gag gag cag tac aac agc acg      960
Val His Asn Ala Lys Thr Lys Pro Arg Glu Glu Gln Tyr Asn Ser Thr
305                 310                 315                 320

tac cgt gtg gtc agc gtc ctc acc gtc ctg cac cag gac tgg ctg aat     1008
Tyr Arg Val Val Ser Val Leu Thr Val Leu His Gln Asp Trp Leu Asn
                325                 330                 335

ggc aag gag tac aag tgc aag gtc tcc aac aaa gcc ctc cca gcc ccc     1056
Gly Lys Glu Tyr Lys Cys Lys Val Ser Asn Lys Ala Leu Pro Ala Pro
            340                 345                 350

atc gag aaa acc atc tcc aaa gcc aaa ggg cag ccc cga gaa cca cag     1104
Ile Glu Lys Thr Ile Ser Lys Ala Lys Gly Gln Pro Arg Glu Pro Gln
        355                 360                 365

gtg tac acc ctg ccc cca tcc cgg gat gag ctg acc aag aac cag gtc     1152
Val Tyr Thr Leu Pro Pro Ser Arg Asp Glu Leu Thr Lys Asn Gln Val
    370                 375                 380

agc ctg acc tgc ctg gtc aaa ggc ttc tat ccc agc gac atc gcc gtg     1200
Ser Leu Thr Cys Leu Val Lys Gly Phe Tyr Pro Ser Asp Ile Ala Val
385                 390                 395                 400
```

```
gag tgg gag agc aat ggg cag ccg gag aac aac tac aag acc acg cct      1248
Glu Trp Glu Ser Asn Gly Gln Pro Glu Asn Asn Tyr Lys Thr Thr Pro
                405                 410                 415

ccc gtg ctg gac tcc gac ggc tcc ttc ttc ctc tac agc aag ctc acc      1296
Pro Val Leu Asp Ser Asp Gly Ser Phe Phe Leu Tyr Ser Lys Leu Thr
            420                 425                 430

gtg gac aag agc agg tgg cag cag ggg aac gtc ttc tca tgc tcc gtg      1344
Val Asp Lys Ser Arg Trp Gln Gln Gly Asn Val Phe Ser Cys Ser Val
        435                 440                 445

atg cat gag gct ctg cac aac cac tac acg cag aag agc ctc tcc ctg      1392
Met His Glu Ala Leu His Asn His Tyr Thr Gln Lys Ser Leu Ser Leu
    450                 455                 460

tct ccg ggt tga                                                      1404
Ser Pro Gly
465


<210> SEQ ID NO 18
<211> LENGTH: 467
<212> TYPE: PRT
<213> ORGANISM: Homo sapiens

<400> SEQUENCE: 18

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Val Lys
            20                  25                  30

Pro Gly Ala Ser Val Lys Ile Ser Cys Lys Ala Ser Gly Tyr Thr Phe
        35                  40                  45

Thr Ala Tyr Tyr Met His Trp Val Lys Gln Ser Pro Val Gln Ser Leu
    50                  55                  60

Glu Trp Ile Gly Leu Val Asn Pro Tyr Asn Gly Phe Ser Ser Tyr Asn
65                  70                  75                  80

Gln Lys Phe Gln Gly Lys Ala Ser Leu Thr Val Asp Arg Ser Ser Ser
                85                  90                  95

Thr Ala Tyr Met Glu Leu His Ser Leu Thr Ser Glu Asp Ser Ala Val
            100                 105                 110

Tyr Tyr Cys Ala Arg Glu Phe Tyr Gly Tyr Arg Tyr Phe Asp Val Trp
        115                 120                 125

Gly Gln Gly Thr Ala Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270
```

```
Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly
465
```

<210> SEQ ID NO 19
<211> LENGTH: 510
<212> TYPE: PRT
<213> ORGANISM: Homo sapiens

<400> SEQUENCE: 19

```
Gln Gly Lys Glu Val Val Leu Leu Asp Phe Ala Ala Ala Gly Gly Glu
1               5                   10                  15

Leu Gly Trp Leu Thr His Pro Tyr Gly Lys Gly Trp Asp Leu Met Gln
            20                  25                  30

Asn Ile Met Asn Asp Met Pro Ile Tyr Met Tyr Ser Val Cys Asn Val
        35                  40                  45

Met Ser Gly Asp Gln Asp Asn Trp Leu Arg Thr Asn Trp Val Tyr Arg
    50                  55                  60

Gly Glu Ala Glu Arg Ile Phe Ile Glu Leu Lys Phe Thr Val Arg Asp
65                  70                  75                  80

Cys Asn Ser Phe Pro Gly Gly Ala Ser Ser Cys Lys Glu Thr Phe Asn
                85                  90                  95

Leu Tyr Tyr Ala Glu Ser Asp Leu Asp Tyr Gly Thr Asn Phe Gln Lys
            100                 105                 110

Arg Leu Phe Thr Lys Ile Asp Thr Ile Ala Pro Asp Glu Ile Thr Val
        115                 120                 125

Ser Ser Asp Phe Glu Ala Arg His Val Lys Leu Asn Val Glu Glu Arg
    130                 135                 140

Ser Val Gly Pro Leu Thr Arg Lys Gly Phe Tyr Leu Ala Phe Gln Asp
145                 150                 155                 160

Ile Gly Ala Cys Val Ala Leu Leu Ser Val Arg Val Tyr Tyr Lys Lys
                165                 170                 175
```

-continued

```
Cys Pro Glu Leu Leu Gln Gly Leu Ala His Phe Pro Glu Thr Ile Ala
            180                 185                 190

Gly Ser Asp Ala Pro Ser Leu Ala Thr Val Ala Gly Thr Cys Val Asp
        195                 200                 205

His Ala Val Val Pro Pro Gly Gly Glu Glu Pro Arg Met His Cys Ala
    210                 215                 220

Val Asp Gly Glu Trp Leu Val Pro Ile Gly Gln Cys Leu Cys Gln Ala
225                 230                 235                 240

Gly Tyr Glu Lys Val Glu Asp Ala Cys Gln Ala Cys Ser Pro Gly Phe
                245                 250                 255

Phe Lys Phe Glu Ala Ser Glu Ser Pro Cys Leu Glu Cys Pro Glu His
            260                 265                 270

Thr Leu Pro Ser Pro Glu Gly Ala Thr Ser Cys Glu Cys Glu Glu Gly
        275                 280                 285

Phe Phe Arg Ala Pro Gln Asp Pro Ala Ser Met Pro Cys Thr Arg Pro
    290                 295                 300

Pro Ser Ala Pro His Tyr Leu Thr Ala Val Gly Met Gly Ala Lys Val
305                 310                 315                 320

Glu Leu Arg Trp Thr Pro Pro Gln Asp Ser Gly Gly Arg Glu Asp Ile
                325                 330                 335

Val Tyr Ser Val Thr Cys Glu Gln Cys Trp Pro Glu Ser Gly Glu Cys
            340                 345                 350

Gly Pro Cys Glu Ala Ser Val Arg Tyr Ser Glu Pro Pro His Gly Leu
        355                 360                 365

Thr Arg Thr Ser Val Thr Val Ser Asp Leu Glu Pro His Met Asn Tyr
    370                 375                 380

Thr Phe Thr Val Glu Ala Arg Asn Gly Val Ser Gly Leu Val Thr Ser
385                 390                 395                 400

Arg Ser Phe Arg Thr Ala Ser Val Ser Ile Asn Gln Thr Glu Pro Pro
                405                 410                 415

Lys Val Arg Leu Glu Gly Arg Ser Thr Thr Ser Leu Ser Val Ser Trp
            420                 425                 430

Ser Ile Pro Pro Pro Gln Gln Ser Arg Val Trp Lys Tyr Glu Val Thr
        435                 440                 445

Tyr Arg Lys Lys Gly Asp Ser Asn Ser Tyr Asn Val Arg Arg Thr Glu
    450                 455                 460

Gly Phe Ser Val Thr Leu Asp Asp Leu Ala Pro Asp Thr Thr Tyr Leu
465                 470                 475                 480

Val Gln Val Gln Ala Leu Thr Gln Glu Gly Gln Gly Ala Gly Ser Lys
                485                 490                 495

Val His Glu Phe Gln Thr Leu Ser Pro Glu Gly Ser Gly Asn
            500                 505                 510
```